(12) United States Patent
Mack et al.

(10) Patent No.: US 7,435,589 B2
(45) Date of Patent: Oct. 14, 2008

(54) METHODS OF DIAGNOSIS OF OVARIAN CANCER, COMPOSITIONS AND METHODS OF SCREENING FOR MODULATORS OF OVARIAN CANCER

(75) Inventors: David H. Mack, Menlo Park, CA (US); Kurt C. Gish, Piedmont, CA (US)

(73) Assignee: PDL Biopharma, Inc., Redwood City, CA (US)

(*) Notice: Subject to any disclaimer, the term of this patent is extended or adjusted under 35 U.S.C. 154(b) by 0 days.

(21) Appl. No.: 11/625,458

(22) Filed: Jan. 22, 2007

(65) Prior Publication Data

US 2007/0154928 A1     Jul. 5, 2007

Related U.S. Application Data

(63) Continuation of application No. 10/173,999, filed on Jun. 17, 2002, now Pat. No. 7,189,507.

(60) Provisional application No. 60/372,246, filed on Apr. 12, 2002, provisional application No. 60/350,666, filed on Nov. 13, 2001, provisional application No. 60/315,287, filed on Aug. 27, 2001, provisional application No. 60/299,234, filed on Jun. 18, 2001.

(51) Int. Cl.
| | |
|---|---|
| C12N 5/00 | (2006.01) |
| C12N 1/20 | (2006.01) |
| C12N 15/00 | (2006.01) |
| C12N 15/12 | (2006.01) |
| C12Q 1/68 | (2006.01) |
| C07H 21/04 | (2006.01) |

(52) U.S. Cl. .................. 435/325; 435/6; 435/252.3; 435/320.1; 536/23.5

(58) Field of Classification Search .................. None
See application file for complete search history.

(56) References Cited

OTHER PUBLICATIONS

McDonald et al, Biochem. Biophys. Res. Comm. 247: 266 (1998).*

* cited by examiner

Primary Examiner—James Martinell
(74) Attorney, Agent, or Firm—Howrey LLP; Adam K. Whiting

(57) ABSTRACT

Described herein are genes whose expression are up-regulated or down-regulated in ovarian cancer. Related methods and compositions that can be used for diagnosis and treatment of ovarian cancer are disclosed. Also described herein are methods that can be used to identify modulators of ovarian cancer.

18 Claims, No Drawings

METHODS OF DIAGNOSIS OF OVARIAN CANCER, COMPOSITIONS AND METHODS OF SCREENING FOR MODULATORS OF OVARIAN CANCER

CROSS-REFERENCES TO RELATED APPLICATIONS

This application is a continuation of U.S. Ser. No. 10/173,999, filed Jun. 17, 2002, now U.S. Pat. No. 7,189,507 which is incorporated herein by reference, and which claims priority from U.S. provisional applications U.S. Ser. No. 60/299,234, filed Jun. 18, 2001; U.S. Ser. No. 60/315,287, filed Aug. 27, 2001; U.S. Ser. No. 60/350,666, filed Nov. 13, 2001; and U.S. Ser. No. 60/372,246, filed Apr. 12, 2002, each of which is incorporated herein by reference for all purposes.

FIELD OF THE INVENTION

The invention relates to the identification of nucleic acid and protein expression profiles and nucleic acids, products, and antibodies thereto that are involved in ovarian cancer; and to the use of such expression profiles and compositions in the diagnosis, prognosis, and therapy of ovarian cancer. The invention further relates to methods for identifying and using agents and/or targets that inhibit ovarian cancer.

BACKGROUND OF THE INVENTION

Ovarian cancer is the sixth most common cancer in women, accounting for 6% of all female cancers. It ranks fifth as the cause of cancer death in women. The American Cancer Society predicts that there will be about 23,100 new cases of ovarian cancer in this country in the year 2000 and about 14,000 women will die of the disease. Because many ovarian cancers cannot be detected early in their development, they account for a disproportionate number of fatal cancers, being responsible for almost half the deaths from cancer of the female genital tract; more deaths than any other reproductive organ cancer.

Most patients with epithelial ovarian cancer, the predominant form, are asymptomatic in early-stage disease and usually present with stage III or IV disease. Their five-year survival is less than 25%, with lower survival among African-American women. The minority of patients discovered with early-stage disease have a five-year survival rate of 80%-90%. See, Parker, et. al. (1997) "Cancer Statistics, 1997" CA Cancer J. Clin. 47:5-27.

In the absence of a family history of ovarian cancer, lifetime risk of ovarian cancer is 1/70. Risk factors include familial cancer syndromes (risk of up to 82% by age 70 in women with hereditary breast/ovarian syndrome); family history (1.4% lifetime risk with no affected relatives, 5% with one affected relative, 7% with two affected relatives; Kerlikowske, et al. (1992) Obstet. Gynecol. 80:700-707); nulliparity; advancing age; obesity; personal history of breast, endometrial, or colorectal cancer; fewer pregnancies; or older age (>35 years) at first pregnancy. However, 95% of all ovarian cancers occur in women without risk factors. Use of hormonal contraceptives, oophorectomy, and tubal sterilization reduce risk of ovarian cancer (Kerlikowske, et al. (1992) Obstet. Gynecol. 80:700-707; Grimes (1992) Am J. Obstet. Gynecol. 166:1950-1954; Hankinson, et. al. (1993) JAMA 270:2813-2818); however, even bilateral oophorectomy may not be completely effective in preventing ovarian cancer.

Treatment of ovarian cancer consists largely of surgical oophorectomy, anti-hormone therapy, and/or chemotherapy. Although many ovarian cancer patients are effectively treated, the current therapies can all induce serious side effects which diminish quality of life. Deciding on a particular course of treatment is typically based on a variety of prognostic parameters and markers (Fitzgibbons, et al. (2000) Arch. Pathol. Lab. Med. 124:966-978; Hamilton and Piccart (2000) Ann. Oncol. 11:647-663), including genetic predisposition markers BRCA-1 and BRCA-2 (Robson (2000) J. Clin. Oncol. 18:113sup-118sup).

The identification of novel therapeutic targets and diagnostic markers is essential for improving the current treatment of ovarian cancer patients. Recent advances in molecular medicine have increased the interest in tumor-specific cell surface antigens that could serve as targets for various immunotherapeutic or small molecule strategies. Antigens suitable for immunotherapeutic strategies should be highly expressed in cancer tissues and ideally not expressed in normal adult tissues. Expression in tissues that are dispensable for life, however, may be tolerated. Examples of such antigens include Her2/neu and the B-cell antigen CD20. Humanized monoclonal antibodies directed to Her2/neu (HERCEPTIN®/trastuzumab) are currently in use for the treatment of metastatic breast cancer. Ross and Fletcher (1998) Stem Cells 16:413-428. Similarly, anti-CD20 monoclonal antibodies (RITUXIN®/rituximab) are used to effectively treat non-Hodgkin's lymphoma. Maloney, et al. (1997) Blood 90:2188-2195; Leget and Czuczman (1998) Curr. Opin. Oncol. 10:548-551.

Potential immunotherapeutic targets have been identified for ovarian cancer. One such target is polymorphic epithelial mucin (MUC1). MUC1 is a transmembrane protein, present at the apical surface of glandular epithelial cells. It is often overexpressed in ovarian cancer, and typically exhibits an altered glycosylation pattern, resulting in an antigenically distinct molecule, and is in early clinical trials as a vaccine target. Gilewski, et al. (2000) Clin. Cancer Res. 6:1693-1701; Scholl, et al. (2000) J. Immunother. 23:570-580. The tumor-expressed protein is often cleaved into the circulation, where it is detectable as the tumor marker, CA 15-3. See, e.g., Bon, et al. (1997) Clin. Chem. 43:585-593. However, many patients have tumors that express neither HER2 nor MUC-1; therefore, it is clear that other targets need to be identified to manage localized and metastatic disease.

Mutations in both BRCA1 and BRCA2 are associated with increased susceptibility to ovarian cancer. Mutations in BRCA1 occur in approximately 5 percent (95 percent confidence interval, 3 to 8 percent) of women in whom ovarian cancer is diagnosed before the age of 70 years. See Stratton, et al. (1997) N.E.J. Med. 336:1125-1130. And, in BRCA1 gene carriers, the risk for developing ovarian cancer is 0.63. See Easton (1995) Am. J. Hum. Genet. 56:267-xxx; and Elit (2001) Can. Fam. Physician 47:778-84.

Other biochemical markers such as CA125 have been reported to be associated with ovarian cancer, but they are not absolute indicators of disease. Although roughly 85% of women with clinically apparent ovarian cancer have increased levels of CA125, CA125 is also increased during the first trimester of pregnancy, during menstruation, in the presence of non-cancerous illnesses, and in cancers of other sites.

While industry and academia have identified novel gene sequences, there has not been an equal effort exerted to identify the function of these novel sequences. The elucidation of a role for novel proteins and compounds in disease states for identification of therapeutic targets and diagnostic markers is essential for improving the current treatment of ovarian cancer patients. Accordingly, provided herein are molecular targets for therapeutic intervention in ovarian and other cancers. Additionally, provided herein are methods that can be used in diagnosis and prognosis of ovarian cancer. Further provided are methods that can be used to screen candidate bioactive agents for the ability to modulate ovarian cancer.

SUMMARY OF THE INVENTION

The present invention therefore provides nucleotide sequences of genes that are up- and down-regulated in ovarian cancer cells. Such genes are useful for diagnostic purposes, and also as targets for screening for therapeutic compounds that modulate ovarian cancer, such as hormones or antibodies. The methods of detecting nucleic acids of the invention or their encoded proteins can be used for many purposes, e.g., early detection of ovarian cancers, monitoring and early detection of relapse following treatment, monitoring response to therapy, selecting patients for postoperative chemotherapy or radiation therapy, selecting therapy, determining tumor prognosis, treatment, or response to treatment (of primary or metastatic tumors), and early detection of precancerous lesions. Other aspects of the invention will become apparent to the skilled artisan by the following description of the invention.

In one aspect, the present invention provides a method of detecting an ovarian cancer-associated transcript in a cell from a patient, the method comprising contacting a biological sample from the patient with a polynucleotide that selectively hybridizes to a sequence at least 80% identical to a sequence as shown in Table 20.

In one embodiment, the present invention provides a method of determining the level of an ovarian cancer associated transcript in a cell from a patient.

In one embodiment, the present invention provides a method of detecting an ovarian cancer-associated transcript in a cell from a patient, the method comprising contacting a biological sample from the patient with a polynucleotide that selectively hybridizes to a sequence at least 80% identical to a sequence as shown in Table 20.

In one embodiment, the polynucleotide selectively hybridizes to a sequence at least 95% identical to a sequence as shown in Table 20.

In one embodiment, the biological sample is a tissue sample. In another embodiment, the biological sample comprises isolated nucleic acids, e.g., mRNA.

In one embodiment, the polynucleotide is labeled, e.g., with a fluorescent label.

In one embodiment, the polynucleotide is immobilized on a solid surface.

In one embodiment, the patient is undergoing a therapeutic regimen to treat ovarian cancer. In another embodiment, the patient is suspected of having metastatic ovarian cancer.

In one embodiment, the patient is a human.

In one embodiment, the ovarian cancer associated transcript is mRNA.

In one embodiment, the method further comprises the step of amplifying nucleic acids before the step of contacting the biological sample with the polynucleotide.

In another aspect, the present invention provides a method of monitoring the efficacy of a therapeutic treatment of ovarian cancer, the method comprising the steps of: (i) providing a biological sample from a patient undergoing the therapeutic treatment; and (ii) determining the level of an ovarian cancer-associated transcript in the biological sample by contacting the biological sample with a polynucleotide that selectively hybridizes to a sequence at least 80% identical to a sequence as shown in Table 20, thereby monitoring the efficacy of the therapy. In a further embodiment, the patient has metastatic ovarian cancer. In a further embodiment, the patient has a drug resistant form of ovarian cancer.

In one embodiment, the method further comprises the step of: (iii) comparing the level of the ovarian cancer-associated transcript to a level of the ovarian cancer-associated transcript in a biological sample from the patient prior to, or earlier in, the therapeutic treatment.

Additionally, provided herein is a method of evaluating the effect of a candidate ovarian cancer drug comprising administering the drug to a patient and removing a cell sample from the patient. The expression profile of the cell is then determined. This method may further comprise comparing the expression profile to an expression profile of a healthy individual. In a preferred embodiment, said expression profile includes a gene of Table 19A.

In one aspect, the present invention provides an isolated nucleic acid molecule consisting of a polynucleotide sequence as shown in Table 20.

In one embodiment, an expression vector or cell comprises the isolated nucleic acid.

In one aspect, the present invention provides an isolated polypeptide which is encoded by a nucleic acid molecule having polynucleotide sequence as shown in Table 20.

In another aspect, the present invention provides an antibody that specifically binds to an isolated polypeptide which is encoded by a nucleic acid molecule having polynucleotide sequence as shown in Table 20.

In one embodiment, the antibody is conjugated to an effector component, e.g., a fluorescent label, a radioisotope or a cytotoxic chemical.

In one embodiment, the antibody is an antibody fragment. In another embodiment, the antibody is humanized.

In one aspect, the present invention provides a method of detecting an ovarian cancer cell in a biological sample from a patient, the method comprising contacting the biological sample with an antibody as described herein.

In another aspect, the present invention provides a method of detecting antibodies specific to ovarian cancer in a patient, the method comprising contacting a biological sample from the patient with a polypeptide encoded by a nucleic acid comprising a sequence from Table 20.

In another aspect, the present invention provides a method for identifying a compound that modulates an ovarian cancer-associated polypeptide, the method comprising the steps of: (i) contacting the compound with an ovarian cancer-associated polypeptide, the polypeptide encoded by a polynucleotide that selectively hybridizes to a sequence at least 80% identical to a sequence as shown in Table 20; and (ii) determining the functional effect of the compound upon the polypeptide.

In one embodiment, the functional effect is a physical effect, an enzymatic effect, or a chemical effect.

In one embodiment, the polypeptide is expressed in a eukaryotic host cell or cell membrane. In another embodiment, the polypeptide is recombinant.

In one embodiment, the functional effect is determined by measuring ligand binding to the polypeptide.

In another aspect, the present invention provides a method of inhibiting proliferation of an ovarian cancer-associated cell to treat ovarian cancer in a patient, the method comprising the step of administering to the subject a therapeutically effective amount of a compound identified as described herein.

In one embodiment, the compound is an antibody.

In another aspect, the present invention provides a drug screening assay comprising the steps of: (i) administering a test compound to a mammal having ovarian cancer or to a cell sample isolated from; (ii) comparing the level of gene expression of a polynucleotide that selectively hybridizes to a sequence at least 80% identical to a sequence as shown in Table 20 in a treated cell or mammal with the level of gene expression of the polynucleotide in a control cell sample or mammal, wherein a test compound that modulates the level of expression of the polynucleotide is a candidate for the treatment of ovarian cancer.

In one embodiment, the control is a mammal with ovarian cancer or a cell sample that has not been treated with the test compound. In another embodiment, the control is a normal cell or mammal, or is non-malignant tissue.

In one embodiment, the test compound is administered in varying amounts or concentrations. In another embodiment, the test compound is administered for varying time periods.

In another embodiment, the comparison can occur after addition or removal of the drug candidate.

In one embodiment, the levels of a plurality of polynucleotides that selectively hybridize to a sequence at least 80% identical to a sequence as shown in Table 20 are individually compared to their respective levels in a control cell sample or mammal. In a preferred embodiment the plurality of polynucleotides is from three to ten.

In another aspect, the present invention provides a method for treating a mammal having ovarian cancer comprising administering a compound identified by the assay described herein.

In another aspect, the present invention provides a pharmaceutical composition for treating a mammal having ovarian cancer, the composition comprising a compound identified by the assay described herein and a physiologically acceptable excipient.

In one aspect, the present invention provides a method of screening drug candidates by providing a cell expressing a gene that is up- and down-regulated as in an ovarian cancer. In one embodiment, a gene is selected from Table 19A. The method further includes adding a drug candidate to the cell and determining the effect of the drug candidate on the expression of the expression profile gene.

In one embodiment, the method of screening drug candidates includes comparing the level of expression in the absence of the drug candidate to the level of expression in the presence of the drug candidate, wherein the concentration of the drug candidate can vary when present, and wherein the comparison can occur after addition or removal of the drug candidate. In a preferred embodiment, the cell expresses at least two expression profile genes. The profile genes may show an increase or decrease.

Also provided is a method of evaluating the effect of a candidate ovarian cancer drug comprising administering the drug to a transgenic animal expressing or over-expressing the ovarian cancer modulatory protein, or an animal lacking the ovarian cancer modulatory protein, for example as a result of a gene knockout.

Moreover, provided herein is a biochip comprising one or more nucleic acid segments of Table 20, wherein the biochip comprises fewer than 1000 nucleic acid probes. Preferably, at least two nucleic acid segments are included. More preferably, at least three nucleic acid segments are included.

Furthermore, a method of diagnosing a disorder associated with ovarian cancer is provided. The method comprises determining the expression of a gene of Table 19A in a first tissue type of a first individual, and comparing the distribution to the expression of the gene from a second normal tissue type from the first individual or a second unaffected individual. A difference in the expression indicates that the first individual has a disorder associated with ovarian cancer.

In a further embodiment, the biochip also includes a polynucleotide sequence of a gene that is not up- and down-regulated in ovarian cancer.

In one embodiment a method for screening for a bioactive agent capable of interfering with the binding of an ovarian cancer modulating protein (ovarian cancer modulatory protein) or a fragment thereof and an antibody which binds to said ovarian cancer modulatory protein or fragment thereof. In a preferred embodiment, the method comprises combining an ovarian cancer modulatory protein or fragment thereof, a candidate bioactive agent and an antibody which binds to said ovarian cancer modulatory protein or fragment thereof. The method further includes determining the binding of said ovarian cancer modulatory protein or fragment thereof and said antibody. Wherein there is a change in binding, an agent is identified as an interfering agent. The interfering agent can be an agonist or an antagonist. Preferably, the agent inhibits ovarian cancer.

Also provided herein are methods of eliciting an immune response in an individual. In one embodiment a method provided herein comprises administering to an individual a composition comprising an ovarian cancer modulating protein, or a fragment thereof. In another embodiment, the protein is encoded by a nucleic acid selected from those of Table 20.

Further provided herein are compositions capable of eliciting an immune response in an individual. In one embodiment, a composition provided herein comprises an ovarian cancer modulating protein, preferably encoded by a nucleic acid of Table 20 or a fragment thereof, and a pharmaceutically acceptable carrier. In another embodiment, said composition comprises a nucleic acid comprising a sequence encoding an ovarian cancer modulating protein, preferably selected from the nucleic acids of Table 20, and a pharmaceutically acceptable carrier.

Also provided are methods of neutralizing the effect of an ovarian cancer protein, or a fragment thereof, comprising contacting an agent specific for said protein with said protein in an amount sufficient to effect neutralization. In another embodiment, the protein is encoded by a nucleic acid selected from those of Table 20.

In another aspect of the invention, a method of treating an individual for ovarian cancer is provided. In one embodiment, the method comprises administering to said individual an inhibitor of an ovarian cancer modulating protein. In another embodiment, the method comprises administering to a patient having ovarian cancer an antibody to an ovarian cancer modulating protein conjugated to a therapeutic moiety. Such a therapeutic moiety can be a cytotoxic agent or a radioisotope.

DETAILED DESCRIPTION OF THE INVENTION

In accordance with the objects outlined above, the present invention provides novel methods for diagnosis and prognosis evaluation for ovarian cancer (OC), including metastatic ovarian cancer, as well as methods for screening for compositions which modulate ovarian cancer. Also provided are methods for treating ovarian cancer and related conditions, e.g., ovarian carcinoma (e.g., epithelial (including malignant serous tumors, malignant mucinous tumors, and malignant endometrioid tumors), germ cell (including teratomas, choriocarcinomas, polyembryomas, embryonal carcinoma, endodermal sinus tumor, dysgerminoma, and gonadoblastoma), and stromal carcinomas (e.g., granulosal stromal cell tumors)), fallopian tube carcinoma, and peritoneal carcinoma.

Table 19A provides unigene cluster identification numbers for the nucleotide sequence of genes that exhibit increased or decreased expression in ovarian cancer samples. Table 19A also provides an exemplar accession number that provides a nucleotide sequence that is part of the unigene cluster.

Definitions

The term "ovarian cancer protein" or "ovarian cancer polynucleotide" or "ovarian cancer-associated transcript" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, preferably 91%, 92%, 93%, 94%, 95%, 96%, 97%, 98%, or 99% or greater nucleotide sequence identity, preferably over a region of over a region of at least about 25, 50, 100, 200, 500, 1000, or more nucleotides, to a nucleotide sequence of or associated with a gene of Table 19A; (2) bind to antibodies, e.g., polyclonal antibodies, raised against an immunogen comprising an amino acid sequence encoded by a nucleotide sequence of or associated with a gene of Table 19A, and conservatively modified variants thereof; (3) specifically hybridize under stringent hybridization conditions to a nucleic acid sequence, or the complement thereof of Table 19A and conservatively modified variants thereof; or (4) have an amino acid sequence that has greater than about 60% amino acid sequence identity, 65%, 70%, 75%, 80%, 85%, 90%, preferably 91%, 92%, 93%, 94%, 95%, 96%, 97%, 98%, or 99% or greater amino sequence identity, preferably over a region of over a region of at least about 25, 50, 100, 200, 500, 1000, or more amino acid, to an amino acid sequence encoded by a nucleotide sequence of or associated with a gene of Table 19A. A polynucleotide or polypeptide sequence is typically from a mammal including, but not limited to, primate, e.g., human; rodent, e.g., rat, mouse, hamster; cow, pig, horse, sheep, or other mammal. An "ovarian cancer polypeptide" and an "ovarian cancer polynucleotide," include both naturally occurring or recombinant forms.

A "full length" ovarian cancer protein or nucleic acid refers to an ovarian cancer polypeptide or polynucleotide sequence, or a variant thereof, that contains all of the elements normally contained in one or more naturally occurring, wild type ovarian cancer polynucleotide or polypeptide sequences. The "full length" may be prior to, or after, various stages of post-translation processing or splicing, including alternative splicing.

"Biological sample" as used herein is a sample of biological tissue or fluid that contains nucleic acids or polypeptides, e.g., of an ovarian cancer protein, polynucleotide or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish. Livestock and domestic animals are of particular interest.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1981) *Adv. Appl. Math.* 2:482-489, by the homology alignment algorithm of Needleman and Wunsch (1970) *J. Mol. Biol.* 48:443-453, by the search for similarity method of Pearson and Lipman (1988) *Proc. Nat'l. Acad. Sci. USA* 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel, et al. (eds. 1995 and supplements) *Current Protocols in Molecular Biology* Lippincott.

Preferred examples of algorithms that are suitable for determining percent sequence identity and sequence similarity include the BLAST and BLAST 2.0 algorithms, which are described in Altschul, et al. (1977) *Nuc. Acids Res.* 25:3389-3402 and Altschul, et al. (1990) *J. Mol. Biol.* 215:403-410. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Nat'l Acad. Sci. USA* 89:10915-919) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Nat'l Acad. Sci. USA* 90:5873-5887). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells, such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. In certain contexts each codon in a nucleic acid (except AUG, which is ordinarily the only codon for methionine, and TGG, which is ordinarily the only codon for tryptophan) can be modified to yield a functionally identical molecule. Accordingly, a silent variation of a nucleic acid which encodes a polypeptide is implicit in a described sequence with respect to the expression product, but not necessarily with respect to actual probe sequences.

As to amino acid sequences, one of skill will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton (1984) *Proteins* Freeman).

Macromolecular structures such as polypeptide structures can be described in terms of various levels of organization. For a general discussion of this organization, see, e.g., Alberts, et al. (2001) *Molecular Biology of the Cell* (4th ed.) Garland Pub.; and Cantor and Schimmel (1980) *Biophysical Chemistry Part I: The Conformation of Biological Macromolecules* Freeman. "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the non-covalent association of independent tertiary units. Anisotropic terms are also known as energy terms.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50, or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have at least one different linkage, e.g., phosphoramidate, phosphorothioate, phosphorodithioate, or O-methylphosphoroamidite linkages (see Eckstein (1992) *Oligonucleotides and Analogues: A Practical Approach* Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7 of Sanghvi and Cook (eds. 1994) *Carbohydrate Modifications in Antisense Research* ASC Symposium Series 580. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, e.g., phosphoramidate (Beaucage, et al. (1993) *Tetrahedron* 49:1925-1963 and references therein; Letsinger (1970) *J. Org. Chem.* 35:3800-3803; Sprinzl, et al. (1977) *Eur. J. Biochem.* 81:579-589; Letsinger, et al. (1986) *Nucl. Acids Res.* 14:3487-499; Sawai, et al. (1984) *Chem. Lett.* 805, Letsinger, et al. (1988) *J. Am. Chem. Soc.* 110:4470-4471; and Pauwels, et al. (1986), *Chemica Scripta* 26:141-149), phosphorothioate (Mag, et al. (1991) *Nucl. Acids Res.* 19:1437-441; and U.S. Pat. No. 5,644,048), phosphorodithioate (Brill, et al. (1989) *J. Am. Chem. Soc.* 111:2321-2322), O-methylphosphoroamidite linkages (see Eckstein (1992) *Oligonucleotides and Analogues: A Practical Approach* Oxford Univ. Press), and peptide nucleic acid backbones and linkages (see Egholm (1992) *J. Am. Chem. Soc.* 114:1895-897; Meier, et al. (1992) *Angew. Chem. Int. Ed. Engl.* 31:1008-1010; Nielsen (1993) *Nature*, 365:566-568; Carlsson, et al. (1996) *Nature* 380:207, each of which is incorporated by reference). Other analog nucleic acids include those with positive backbones (Denpcy, et al. (1995) *Proc. Nat'l Acad. Sci. USA* 92:6097-101; non-ionic backbones (U.S. Pat. Nos. 5,386,023, 5,637,684, 5,602,240, 5,216,141 and 4,469,863; Kiedrowski, et al. (1991) *Angew. Chem. Intl. Ed. English* 30:423-426; Letsinger, et al. (1988) *J. Am. Chem. Soc.* 110: 4470-4471; Jung, et al. (1994) *Nucleoside and Nucleotide* 13:1597; Chapters 2 and 3, in Sanghvi and Cook (eds. 1994) *Carbohydrate Modifications in Antisense Research* ASC Symposium Series 580; Mesmaeker, et al. (1994) *Bioorganic and Medicinal Chem. Lett.* 4:395-398; Jeffs, et al. (1994) *J. Biomolecular NMR* 34:17-xx; Horn, et al. (1996) *Tetrahedron Lett.* 37:743-xxx) and non-ribose backbones, including those described in U.S. Pat. Nos. 5,235,033 and 5,034,506, and Chapters 6 and 7, in Sanghvi and Cook (eds. 1994) *Carbohydrate Modifications in Antisense Research* ASC Symposium Series 580. Nucleic acids containing one or more carbocyclic sugars are also included within one definition of nucleic acids (see Jenkins, et al. (1995) *Chem. Soc. Rev.* pp 169-176). Several nucleic acid analogs are described in Rawls (p. 35 Jun. 2, 1997) *C&E News*. Each of these references is hereby expressly incorporated by reference.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched base pairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the ovarian cancer nucleic acids, proteins and antibodies at any position. Any method known in the art for conjugating the antibody to the label may be employed, including those methods described by Hunter, et al. (1962) *Nature* 144:945-xxx; David, et al. (1974) *Biochemistry* 13:1014-1021; Pain, et al. (1981) *J. Immunol. Meth.* 40:219-230; and Nygren (1982) *J. Histochem. and Cytochem.* 30:407-412.

An "effector" or "effector moiety" or "effector component" is a molecule that is bound (or linked, or conjugated), either covalently, through a linker or a chemical bond, or non-covalently, through ionic, van der Waals, electrostatic, or hydrogen bonds, to an antibody. The "effector" can be a variety of molecules including, e.g., detection moieties including radioactive compounds, fluorescent compounds, an enzyme or substrate, tags such as epitope tags, a toxin; activatable moieties, a chemotherapeutic agent; a lipase; an antibiotic; or a radioisotope emitting "hard" e.g., beta radiation.

A "labeled nucleic acid probe or oligonucleotide" is one that is bound, either covalently, through a linker or a chemical bond, or non-covalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is a nucleic acid capable of binding to a target nucleic acid of complementary sequence through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. Probes may bind target sequences lacking complete complementarity with the probe sequence depending upon the stringency of the hybridization conditions. The probes are preferably directly labeled, e.g., with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, e.g., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, e.g., wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in "Overview of principles of hybridization and the strategy of nucleic acid assays" in Tijssen (1993) *Hybridization with Nucleic Probes* (*Laboratory Techniques in Biochemistry and Molecular Biology*) (vol. 24) Elsevier. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

Nucleic acids that do not hybridize to each other under stringent conditions are still substantially identical if the polypeptides which they encode are substantially identical.

This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Alternative hybridization and wash conditions can be utilized to provide conditions of similar stringency. Additional guidelines for determining hybridization parameters are provided, e.g., Ausubel, et al. (ed. 1991 and supplements) *Current Protocols in Molecular Biology* Lippincott.

The phrase "functional effects" in the context of assays for testing compounds that modulate activity of an ovarian cancer protein includes the determination of a parameter that is indirectly or directly under the influence of the ovarian cancer protein or nucleic acid, e.g., a functional, physical, physiological, or chemical effect, such as the ability to decrease ovarian cancer. It includes ligand binding activity; cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of ovarian cancer cells. "Functional effects" include in vitro, in vivo, and ex vivo activities.

By "determining the functional effect" is meant assaying for a compound that increases or decreases a parameter that is indirectly or directly under the influence of an ovarian cancer protein sequence, e.g., functional, enzymatic, physical, physiological, and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the ovarian cancer protein; measuring binding activity or binding assays, e.g., binding to antibodies or other ligands, and measuring cellular proliferation. Determination of the functional effect of a compound on ovarian cancer can also be performed using ovarian cancer assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of ovarian cancer cells. The functional effects can be evaluated by means known to those skilled in the art, e.g., microscopy for quantitative or qualitative measures of alterations in morphological features, measurement of changes in RNA or protein levels for ovarian cancer-associated sequences, measurement of RNA stability, or identification of downstream or reporter gene expression (CAT, luciferase, β-gal, GFP, and the like), e.g., via chemiluminescence, fluorescence, colorimetric reactions, antibody binding, inducible markers, and ligand binding assays.

"Inhibitors", "activators", and "modulators" of ovarian cancer polynucleotide and polypeptide sequences are used to refer to activating, inhibitory, or modulating molecules or compounds identified using in vitro and in vivo assays of ovarian cancer polynucleotide and polypeptide sequences. Inhibitors are compounds that, e.g., bind to, partially or totally block activity, decrease, prevent, delay activation, inactivate, desensitize, or down regulate the activity or expression of ovarian cancer proteins, e.g., antagonists. Antisense or inhibitory nucleic acids may inhibit expression and subsequent function of the protein. "Activators" are compounds that increase, open, activate, facilitate, enhance activation, sensitize, agonize, or up regulate ovarian cancer protein activity. Inhibitors, activators, or modulators also include genetically modified versions of ovarian cancer proteins, e.g., versions with altered activity, as well as naturally occurring and synthetic ligands, antagonists, agonists, antibodies, small chemical molecules, and the like. Assays for inhibitors and activators include, e.g., expressing the ovarian cancer protein in vitro, in cells, or cell membranes, applying putative modulator compounds, and then determining the functional effects on activity, as described above. Activators and inhibitors of ovarian cancer can also be identified by incubating ovarian cancer cells with the test compound and determining increases or decreases in the expression of one or more ovarian cancer proteins, e.g., 1, 2, 3, 4, 5, 10, 15, 20, 25, 30, 40, 50, or more ovarian cancer proteins, such as ovarian cancer proteins encoded by the sequences set out in Table 19A.

Samples or assays comprising ovarian cancer proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of a polypeptide is achieved when the activity value relative to the control is about 80%, preferably 50%, more preferably 25% or less. Activation of an ovarian cancer polypeptide is achieved when the activity value relative to the control (untreated with activators) is 110%, more preferably 150%, more preferably 200-500% (e.g., 2-5 fold higher relative to the control), more preferably 1000-3000% higher.

The phrase "changes in cell growth" refers to a change in cell growth and proliferation characteristics in vitro or in vivo, e.g., cell viability, formation of foci, anchorage independence, semi-solid or soft agar growth, change in contact inhibition or density limitation of growth, loss of growth factor or serum requirements, change in cell morphology, gain or loss of immortalization, gain or loss of tumor specific markers, ability to form or suppress tumors when injected into suitable animal hosts, and/or immortalization of the cell. See, e.g., pp. 231-241 in Freshney (1994) *Culture of Animal Cells: A Manual of Basic Technique* (3d ed.) Wiley-Liss.

"Tumor cell" refers to pre-cancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is typically associated with phenotypic changes, such as immortalization of cells, aberrant growth control, non-morphological changes, and/or malignancy. See, Freshney (1994) *Culture of Animal Cells*.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, the antigen-binding region of an antibody or its functional equivalent will be most critical in specificity and affinity of binding. See, e.g., Paul (ed. 1999) *Fundamental Immunology* (4th ed.) Raven.

An exemplary immunoglobulin (antibody) structural unit comprises a tetramer. Each tetramer is composed of two identical pairs of polypeptide chains, each pair having one "light"

(about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. See Paul (ed. 1999) *Fundamental Immunology* (4th ed.) Raven. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries. See, e.g., McCafferty, et al. (1990) *Nature* 348:552-554.

For preparation of antibodies, e.g., recombinant, monoclonal, or polyclonal antibodies, many techniques known in the art can be used (see, e.g., Kohler and Milstein (1975) *Nature* 256:495-497; Kozbor, et al. (1983) *Immunology Today* 4:72; Cole, et al., pp. 77-96 in Reisfeld and Sell (1985) *Monoclonal Antibodies and Cancer Therapy* Liss; Coligan (1991) *Current Protocols in Immunology* Lippincott; Harlow and Lane (1988) *Antibodies: A Laboratory Manual* CSH Press; and Goding (1986) *Monoclonal Antibodies: Principles and Practice* (2d ed.) Academic Press. Techniques for the production of single chain antibodies (U.S. Pat. No. 4,946, 778) can be adapted to produce antibodies to polypeptides of this invention. Transgenic mice, or other organisms, e.g., other mammals, may be used to express humanized antibodies. Alternatively, phage display technology can be used to identify antibodies and heteromeric Fab fragments that specifically bind to selected antigens. See, e.g., McCafferty, et al. (1990) *Nature* 348:552-554; and Marks, et al. (1992) *Biotechnology* 10:779-783.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Identification of Ovarian Cancer-associated Sequences

In one aspect, the expression levels of genes are determined in different patient samples for which diagnosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is characteristic of the state of the cell. That is, normal tissue (e.g., normal ovarian or other tissue) may be distinguished from cancerous or metastatic cancerous tissue of the ovarian, or ovarian cancer tissue or metastatic ovarian cancerous tissue can be compared with tissue samples of ovarian and other tissues from surviving cancer patients. By comparing expression profiles of tissue in known different ovarian cancer states, information regarding which genes are important (including both up- and down-regulation of genes) in each of these states is obtained. Molecular profiling may distinguish subtypes of a currently collective disease designation, e.g., different forms of a cancer.

The identification of sequences that are differentially expressed in ovarian cancer versus non-ovarian cancer tissue allows the use of this information in a number of ways. For example, a particular treatment regime may be evaluated: does a chemotherapeutic drug act to down-regulate ovarian cancer, and thus tumor growth or recurrence, in a particular patient. Alternatively, does existing treatment induce expression of a target. Similarly, diagnosis and treatment outcomes may be done or confirmed by comparing patient samples with the known expression profiles. Metastatic tissue can also be analyzed to determine the stage of ovarian cancer in the tissue or origin of the primary tumor. Furthermore, these gene expression profiles (or individual genes) allow screening of drug candidates with an eye to mimicking or altering a particular expression profile; e.g., screening can be done for drugs that suppress the ovarian cancer expression profile. This may be done by making biochips comprising sets of the important ovarian cancer genes, which can then be used in these screens. These methods can also be based on evaluating protein expression; that is, protein expression levels of the ovarian cancer proteins can be evaluated for diagnostic purposes or to screen candidate agents. In addition, the ovarian cancer nucleic acid sequences can be administered for gene therapy purposes, including the administration of antisense or RNAi nucleic acids, or the ovarian cancer proteins (including antibodies and other modulators thereof) administered as therapeutic drugs.

Thus the present invention provides nucleic acid and protein sequences that are differentially expressed in ovarian cancer relative to normal tissues and/or non-malignant tissues, herein termed "ovarian cancer sequences." As outlined below, ovarian cancer sequences include those that are up-regulated (e.g., expressed at a higher level) in ovarian cancer, as well as those that are down-regulated (e.g., expressed at a lower level). In a preferred embodiment, the ovarian cancer sequences are from humans; however, as will be appreciated by those in the art, ovarian cancer sequences from other organisms may be useful in animal models of disease and drug evaluation; thus, other ovarian cancer sequences are provided, from vertebrates, including mammals, including rodents (rats, mice, hamsters, guinea pigs, etc.), primates, farm animals (including sheep, goats, pigs, cows, horses, etc.) and pets (e.g., dogs, cats, etc.). Ovarian cancer sequences, e.g., counterpart genes, from other organisms may be obtained using the techniques outlined below.

Ovarian cancer sequences can include both nucleic acid and amino acid sequences. Ovarian cancer nucleic acid sequences are useful in a variety of applications, including diagnostic applications, which will detect naturally occurring nucleic acids. Screening applications; e.g., biochips comprising nucleic acid probes or PCR microtiter plates with selected probes to the ovarian cancer sequences, are also provided.

An ovarian cancer sequence can be initially identified by substantial nucleic acid and/or amino acid sequence homology to the ovarian cancer sequences outlined herein. Such homology can be based upon the overall nucleic acid or amino acid sequence, and is generally determined as outlined below, using either homology programs or hybridization conditions.

For identifying ovarian cancer-associated sequences, the ovarian cancer screen typically includes comparing genes identified in different tissues, e.g., normal and cancerous tissues, or tumor tissue samples from patients who have metastatic disease vs. non metastatic tissue. Other suitable tissue comparisons include comparing ovarian cancer samples with metastatic cancer samples from other cancers, such as lung, ovarian, gastrointestinal cancers, etc. Samples of different stages of ovarian cancer, e.g., survivor tissue, drug resistant states, and tissue undergoing metastasis, are applied to biochips comprising nucleic acid probes. The samples are first microdissected, if applicable, and treated for the preparation of mRNA. Suitable biochips are commercially available, e.g., from Affymetrix. Gene expression profiles as described herein are generated and the data analyzed.

In one embodiment, the genes showing changes in expression as between normal and disease states are compared to genes expressed in other normal tissues, preferably normal ovarian, but also including, and not limited to, lung, heart, brain, liver, ovarian, kidney, muscle, colon, small intestine, large intestine, spleen, bone, and/or placenta. In a preferred embodiment, those genes identified during the ovarian cancer screen that are expressed in any significant amount in other tissues are removed from the profile, although in some embodiments, expression in non-essential tissues may be tolerated. That is, when screening for drugs, it is usually preferable that the target be disease specific, to minimize possible side effects by interaction with target present in other organs.

In a preferred embodiment, ovarian cancer sequences are those that are up-regulated in ovarian cancer; that is, the expression of these genes is higher in the ovarian cancer tissue as compared to non-cancerous tissue. "Up-regulation" as used herein often means at least about a two-fold change, preferably at least about a three fold change, with at least about five-fold or higher being preferred. Other embodiments are directed to sequences up regulated in non-malignant conditions relative to normal.

Unigene cluster identification numbers and accession numbers herein refer to the GenBank sequence database and the sequences of the accession numbers are hereby expressly incorporated by reference. GenBank is known in the art, see, e.g., Benson, et al. (1998) *Nucl. Acids Res.* 26:1-7; and www.ncbi.nlm.nih.gov. Sequences are also available in other databases, e.g., European Molecular Biology Laboratory (EMBL) and DNA Database of Japan (DDBJ). In some situations, the sequences may be derived from assembly of available sequences or be predicted from genomic DNA using exon prediction algorithms, e.g., FGENESH. See Salamov and Solovyev (2000) *Genome Res.* 10:516-522. In other situations, sequences have been derived from cloning and sequencing of isolated nucleic acids.

In another preferred embodiment, ovarian cancer sequences are those that are down-regulated in ovarian cancer; that is, the expression of these genes is lower in ovarian cancer tissue as compared to non-cancerous tissue. "Down-regulation" as used herein often means at least about a two-fold change, preferably at least about a three-fold change, with at least about five-fold or higher being preferred.

Informatics

The ability to identify genes that are over or under expressed in ovarian cancer can additionally provide high-resolution, high-sensitivity datasets which can be used in the areas of diagnostics, therapeutics, drug development, pharmacogenetics, protein structure, biosensor development, and other related areas. Expression profiles can be used in diagnostic or prognostic evaluation of patients with ovarian cancer. Subcellular toxicological information can be generated to better direct drug structure and activity correlation (see Anderson (Jun. 11-12, 1998) *Pharmaceutical Proteomics: Targets, Mechanism, and Function*, paper presented at the IBC Proteomics conference, Coronado, Calif.) or in a biological sensor device to predict the likely toxicological effect of chemical exposures and likely tolerable exposure thresholds (see U.S. Pat. No. 5,811,231). Similar advantages accrue from datasets relevant to other biomolecules and bioactive agents (e.g., nucleic acids, saccharides, lipids, drugs, and the like).

Thus, in another embodiment, the present invention provides a database that includes at least one set of assay data.

The data contained in the database is acquired, e.g., using array analysis either singly or in a library format. The database can be in a form in which data can be maintained and transmitted, but is preferably an electronic database, and can be maintained on any electronic device allowing for the storage of and access to the database, such as a personal computer, but is preferably distributed on a wide area network, such as the World Wide Web.

The focus of the present section on databases that include peptide sequence data is for clarity of illustration only. It will be apparent to those of skill in the art that similar databases can be assembled for any assay data acquired using an assay of the invention.

The compositions and methods for identifying and/or quantitating the relative and/or absolute abundance of a variety of molecular and macromolecular species from a biological sample undergoing ovarian cancer, e.g., the identification of ovarian cancer-associated sequences described herein, provide an abundance of information which can be correlated with pathological conditions, predisposition to disease, drug testing, therapeutic monitoring, gene-disease causal linkages, identification of correlates of immunity and physiological status, and outcome data, among others. Although data generated from the assays of the invention is suited for manual review and analysis, in a preferred embodiment, data processing using high-speed computers is utilized.

An array of methods for indexing and retrieving biomolecular information is known in the art. For example, U.S. Pat. Nos. 6,023,659 and 5,966,712 disclose a relational database system for storing biomolecular sequence information in a manner that allows sequences to be catalogued and searched according to one or more protein function hierarchies. U.S. Pat. No. 5,953,727 discloses a relational database having sequence records containing information in a format that allows a collection of partial-length DNA sequences to be catalogued and searched according to association with one or more sequencing projects for obtaining full-length sequences from the collection of partial length sequences. U.S. Pat. No. 5,706,498 discloses a gene database retrieval system for making a retrieval of a gene sequence similar to a sequence data item in a gene database based on the degree of similarity between a key sequence and a target sequence. U.S. Pat. No. 5,538,897 discloses a method using mass spectroscopy fragmentation patterns of peptides to identify amino acid sequences in computer databases by comparison of predicted mass spectra with experimentally-derived mass spectra using a closeness-of-fit measure. U.S. Pat. No. 5,926,818 discloses a multi-dimensional database comprising a functionality for multi-dimensional data analysis described as on-line analytical processing (OLAP), which entails the consolidation of projected and actual data according to more than one consolidation path or dimension. U.S. Pat. No. 5,295,261 reports a hybrid database structure in which the fields of each database record are divided into two classes, navigational and informational data, with navigational fields stored in a hierarchical topological map which can be viewed as a tree structure or as the merger of two or more such tree structures.

Fundamentals of bioinformatics are provided, e.g., in Mount, et al. (2001) *Bioinformatics: Sequence and Genome Analysis* CSH Press, NY; Durbin, et al. (eds. 1999) *Biological Sequence Analysis: Probabilistic Models of Proteins and Nucleic Acids* Cambridge Univ. Press; Baxevanis and Oeullette (eds. 1998) *Bioinformatics: A Practical Guide to the Analysis of Genes and Proteins* (2d ed.) Wiley-Liss; Rashidi and Buehler (1999) *Bioinformatics: Basic Applications in Biological Science and Medicine* CRC Press; Setubal, et al. (eds 1997) *Introduction to Computational Molecular Biology* Brooks/Cole; Misener and Krawetz (eds. 2000) *Bioinformatics: Methods and Protocols* Humana Press; Higgins and Taylor (eds. 2000) *Bioinformatics: Sequence, Structure, and Databanks: A Practical Approach* Oxford Univ. Press; Brown (2001) *Bioinformatics: A Biologist's Guide to Bio-* computing and the Internet Eaton Pub.; Han and Kamber (2000) *Data Mining: Concepts and Techniques* Kaufmann Pub.; and Waterman (1995) *Introduction to Computational Biology: Maps, Sequences, and Genomes* Chap and Hall.

The present invention provides a computer database comprising a computer and software for storing in computer-retrievable form assay data records cross-tabulated, e.g., with data specifying the source of the target-containing sample from which each sequence specificity record was obtained.

In an exemplary embodiment, at least one of the sources of target-containing sample is from a control tissue sample known to be free of pathological disorders. In a variation, at least one of the sources is a known pathological tissue specimen, e.g., a neoplastic lesion or another tissue specimen to be analyzed for ovarian cancer. In another variation, assay records cross-tabulate one or more of the following parameters for a target species in a sample: (1) a unique identification code, which can include, e.g., a target molecular structure and/or characteristic separation coordinate (e.g., electrophoretic or genomic position coordinates); (2) sample source; and (3) absolute and/or relative quantity of target species present in the sample.

The invention also provides for the storage and retrieval of a collection of target data in a computer data storage apparatus, which can include magnetic disks, optical disks, magneto-optical disks, DRAM, SRAM, SGRAM, SDRAM, RDRAM, DDR RAM, magnetic bubble memory devices, and other data storage devices, including CPU registers and on-CPU data storage arrays. Typically, the target data records are stored as a bit pattern in an array of magnetic domains on a magnetizable medium or as an array of charge states or transistor gate states, such as an array of cells in a DRAM device (e.g., each cell comprised of a transistor and a charge storage area, which may be on the transistor). In one embodiment, the invention provides such storage devices, and computer systems built therewith, comprising a bit pattern encoding a protein expression fingerprint record comprising unique identifiers for at least 10 target data records cross-tabulated with target source.

When the target is a peptide or nucleic acid, the invention preferably provides a method for identifying related peptide or nucleic acid sequences, comprising performing a computerized comparison between a peptide or nucleic acid sequence assay record stored in or retrieved from a computer storage device or database and at least one other sequence. The comparison can include a sequence analysis or comparison algorithm or computer program embodiment thereof (e.g., FASTA, TFASTA, GAP, BESTFIT) and/or the comparison may be of the relative amount of a peptide or nucleic acid sequence in a pool of sequences determined from a polypeptide or nucleic acid sample of a specimen.

The invention also preferably provides a magnetic disk, such as an IBM-compatible (DOS, Windows, Windows95/98/2000, Windows NT, OS/2) or other format (e.g., Linux, SunOS, Solaris, AIX, SCO Unix, VMS, MV, Macintosh, etc.) floppy diskette or hard (fixed, Winchester) disk drive, comprising a bit pattern encoding data from an assay of the invention in a file format suitable for retrieval and processing in a computerized sequence analysis, comparison, or relative quantitation method.

The invention also provides a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The invention also provides a method for transmitting assay data that includes generating an electronic signal on an electronic communications device, such as a modem, ISDN terminal adapter, DSL, cable modem, ATM switch, or the like, wherein the signal includes (in native or encrypted format) a bit pattern encoding data from an assay or a database comprising a plurality of assay results obtained by the method of the invention.

In a preferred embodiment, the invention provides a computer system for comparing a query target to a database containing an array of data structures, such as an assay result obtained by the method of the invention, and ranking database targets based on the degree of identity and gap weight to the target data. A central processor is preferably initialized to load and execute the computer program for alignment and/or comparison of the assay results. Data for a query target is entered into the central processor via an I/O device. Execution of the computer program results in the central processor retrieving the assay data from the data file, which comprises a binary description of an assay result.

The target data or record and the computer program can be transferred to secondary memory, which is typically random access memory (e.g., DRAM, SRAM, SGRAM, or SDRAM). Targets are ranked according to the degree of correspondence between a selected assay characteristic (e.g., binding to a selected affinity moiety) and the same characteristic of the query target and results are output via an I/O device. For example, a central processor can be a conventional computer (e.g., Intel Pentium, PowerPC, Alpha, PA-8000, SPARC, MIPS 4400, MIPS 10000, VAX, etc.); a program can be a commercial or public domain molecular biology software package (e.g., UWGCG Sequence Analysis Software, Darwin); a data file can be an optical or magnetic disk, a data server, a memory device (e.g., DRAM, SRAM, SGRAM, SDRAM, EPROM, bubble memory, flash memory, etc.); an I/O device can be a terminal comprising a video display and a keyboard, a modem, an ISDN terminal adapter, an Ethernet port, a punched card reader, a magnetic strip reader, or other suitable I/O device.

The invention also preferably provides the use of a computer system, e.g., which typically comprises one or more of: (1) a computer; (2) a stored bit pattern encoding a collection of peptide sequence specificity records obtained by methods of the inventions, which may be stored in the computer; (3) a comparison target, such as a query target; and (4) a program for alignment and comparison, typically with rank-ordering of comparison results on the basis of computed similarity values.

Characteristics of Ovarian Cancer-Associated Proteins

Ovarian cancer proteins of the present invention may be categorized as secreted proteins, transmembrane proteins, or intracellular proteins. In one embodiment, the ovarian cancer protein is an intracellular protein. Intracellular proteins may be found in the cytoplasm and/or in the nucleus. Intracellular proteins are involved in all aspects of cellular function and replication (including, e.g., signaling pathways); aberrant expression of such proteins often results in unregulated or disregulated cellular processes. See, e.g., Alberts, et al. (eds. 1994) *Molecular Biology of the Cell* (3d ed.) Garland. For example, many intracellular proteins have enzymatic activity such as protein kinase activity, protein phosphatase activity, protease activity, nucleotide cyclase activity, polymerase activity, and the like. Intracellular proteins can also serve as docking proteins that are involved in organizing complexes of proteins, or targeting proteins to various subcellular localizations, and are often involved in maintaining the structural integrity of organelles.

An increasingly appreciated concept in characterizing proteins is the presence in the proteins of one or more structural motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of amino acid sequence; thus, an analysis of the sequence of proteins may provide insight into both the enzymatic potential of the molecule and/or molecules with which the protein may associate. One useful database is Pfam (protein families), which is a large collection of multiple sequence alignments and hidden Markov models covering many common protein domains. Versions are available via the internet from Washington University in St. Louis, the Sanger Center in England, and the Karolinska Institute in Sweden. See, e.g., Bateman, et al. (2000) *Nuc. Acids Res.* 28:263-266; Sonnhammer, et al. (1997) *Proteins* 28:405-420; Bateman, et al. (1999) *Nuc. Acids Res.* 27:260-262; and Sonnhammer, et al. (1998) *Nuc. Acids Res.* 26:320-322.

In another preferred embodiment, the ovarian cancer sequences are transmembrane proteins. Transmembrane proteins are molecules that span a phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors such as G protein coupled receptors (GPCRs) are classified as "seven transmembrane domain" proteins, as they contain 7 membrane spanning regions. Characteristics of transmembrane domains include approximately 17 consecutive hydrophobic amino acids that may be followed by charged amino acids. Therefore, upon analysis of the amino acid sequence of a particular protein, the localization and number of transmembrane domains within the protein may be predicted (see, e.g., PSORT web site located at psort.nibb.ac.jp). Important transmembrane protein receptors include, but are not limited to the insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g., IL-1 receptor, IL-2 receptor, etc.

The extracellular domains of transmembrane proteins are diverse; however, conserved motifs are found repeatedly among various extracellular domains. Conserved structure and/or functions have been ascribed to different extracellular motifs. Many extracellular domains are involved in binding to other molecules. In one aspect, extracellular domains are found on receptors. Factors that bind the receptor domain include circulating ligands, which may be peptides, proteins, or small molecules such as adenosine and the like. For example, growth factors such as EGF, FGF, and PDGF are circulating growth factors that bind to their cognate receptors to initiate a variety of cellular responses. Other factors include cytokines, mitogenic factors, neurotrophic factors and the like. Extracellular domains also bind to cell-associated molecules, or may be processed or shed to the blood stream. In this respect, they can mediate cell-cell interactions. Cell-associated ligands can be tethered to the cell, e.g., via a glycosylphosphatidylinositol (GPI) anchor, or may themselves be transmembrane proteins. Extracellular domains also associate with the extracellular matrix and contribute to the maintenance of the cell structure.

Ovarian cancer proteins that are transmembrane are particularly preferred in the present invention as they are readily accessible targets for immunotherapeutics, as are described herein. In addition, as outlined below, transmembrane proteins can be also useful in imaging modalities. Antibodies may be used to label such readily accessible proteins in situ. Alternatively, antibodies can also label intracellular proteins, in which case samples are typically permeablized to provide access to intracellular proteins. In addition, some membrane proteins can be processed to release a soluble protein, or to expose a residual fragment. Released soluble proteins may be useful diagnostic markers, processed residual protein fragments may be useful ovarian markers of disease.

It will also be appreciated by those in the art that a transmembrane protein can be made soluble by removing transmembrane sequences, e.g., through recombinant methods. Furthermore, transmembrane proteins that have been made soluble can be made to be secreted through recombinant means by adding an appropriate signal sequence.

In another embodiment, the ovarian cancer proteins are secreted proteins; the secretion of which can be either constitutive or regulated. These proteins may have a signal peptide or signal sequence that targets the molecule to the secretory pathway. Secreted proteins are involved in numerous physiological events; e.g., if circulating, they often serve to transmit signals to various other cell types. The secreted protein may function in an autocrine manner (acting on the cell that secreted the factor), a paracrine manner (acting on cells in close proximity to the cell that secreted the factor), an endocrine manner (acting on cells at a distance, e.g., secretion into the blood stream), or exocrine (secretion, e.g., through a duct or to an adjacent epithelial surface as sweat glands, sebaceous glands, pancreatic ducts, lacrimal glands, mammary glands, wax producing glands of the ear, etc.). Thus, secreted molecules often find use in modulating or altering numerous aspects of physiology. Ovarian cancer proteins that are secreted proteins are particularly preferred as good diagnostic markers, e.g., for blood, plasma, serum, or stool tests. Those which are enzymes may be antibody or small molecule therapeutic targets. Others may be useful as vaccine targets, e.g., via CTL mechanisms, as protein or DNA vaccines.

Use of Ovarian Cancer Nucleic Acids

As described above, ovarian cancer sequence is initially identified by substantial nucleic acid and/or amino acid sequence homology or linkage to the ovarian cancer sequences outlined herein. Such homology can be based upon the overall nucleic acid or amino acid sequence, and is generally determined as outlined below, using either homology programs or hybridization conditions. Typically, linked sequences on a mRNA are found on the same molecule.

The ovarian cancer nucleic acid sequences of the invention, e.g., in Table 19A, can be fragments of larger genes, e.g., they are nucleic acid segments. "Genes" in this context includes coding regions, non-coding regions, and mixtures of coding and non-coding regions. Accordingly, as will be appreciated by those in the art, using the sequences provided herein, extended sequences, in either direction, of the ovarian cancer genes can be obtained, using techniques well known in the art for cloning either longer sequences or the full length sequences; see Ausubel, et al., supra. Much can be done by informatics and many sequences can be clustered to include multiple sequences corresponding to a single gene, e.g., systems such as UniGene (see, www.ncbi.nlm.nih.gov/UniGene).

Once the ovarian cancer nucleic acid is identified, it can be cloned and, if necessary, its constituent parts recombined to form the entire ovarian cancer nucleic acid coding regions or the entire mRNA sequence. Once isolated from its natural source, e.g., contained within a plasmid or other vector or excised as a linear nucleic acid segment, the recombinant ovarian cancer nucleic acid can be further-used as a probe to identify and isolate other ovarian cancer nucleic acids, e.g., extended coding regions. It can also be used as a "precursor" nucleic acid to make modified or variant ovarian cancer nucleic acids and proteins.

The ovarian cancer nucleic acids of the present invention are useful in several ways. In a first embodiment, nucleic acid probes to the ovarian cancer nucleic acids are made and attached to biochips to be used in screening and diagnostic methods, as outlined below, or for administration, e.g., for gene therapy, vaccine, RNAi, and/or antisense applications. Alternatively, the ovarian cancer nucleic acids that include coding regions of ovarian cancer proteins can be put into expression vectors for the expression of ovarian cancer proteins, again for screening purposes or for administration to a patient.

In a preferred embodiment, nucleic acid probes to ovarian cancer nucleic acids (both the nucleic acid sequences outlined in the figures and/or the complements thereof) are made. The nucleic acid probes attached to the biochip are designed to be substantially complementary to the ovarian cancer nucleic acids, e.g., the target sequence (either the target sequence of the sample or to other probe sequences, e.g., in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (e.g., have some sequence in common), or separate. In some cases, PCR primers may be used to amplify signal for higher sensitivity.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can typically be covalent or non-covalent. By "non-covalent binding" and grammatical equivalents herein is meant one or more of electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant a material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. See, e.g., WO0055627 Reusable Low Fluorescent Plastic Biochip.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, e.g., the biochip is derivatized with a chemical functional group including, but not limited to, amino groups, carboxyl groups, oxo groups and thiol groups, with amino groups being particularly preferred. Using these functional groups, the probes can be attached using functional groups on the probes. For example, nucleic acids containing amino groups can be attached to surfaces comprising amino groups, e.g., using linkers as are known in the art; e.g., homo-or hetero-bifunctional linkers as are well known (see 1994 Pierce Chemical Company catalog, technical section on cross-linkers, pages 155-200). In addition, in some cases, additional linkers, such as alkyl groups (including substituted and heteroalkyl groups) may be used.

In this embodiment, oligonucleotides are synthesized as is known in the art, and then attached to the surface of the solid support. As will be appreciated by those skilled in the art, either the 5' or 3' terminus may be attached to the solid support, or attachment may be via an internal nucleoside.

In another embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GeneChip™ technology.

Often, amplification-based assays are performed to measure the expression level of ovarian cancer-associated sequences. These assays are typically performed in conjunction with reverse transcription. In such assays, an ovarian cancer-associated nucleic acid sequence acts as a template in an amplification reaction (e.g., Polymerase Chain Reaction, or PCR). In a quantitative amplification, the amount of amplification product will be proportional to the amount of template in the original sample. Comparison to appropriate controls provides a measure of the amount of ovarian cancer-associated RNA. Methods of quantitative amplification are well known to those of skill in the art. Detailed protocols for quantitative PCR are available. See, e.g., Innis, et al. (1990) *PCR Protocols: A Guide to Methods and Applications* Academic Press.

In some embodiments, a TaqMan based assay is used to measure expression. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, e.g., literature provided by Perkin-Elmer, e.g., www2.perkin-elmer.com).

Other suitable amplification methods include, but are not limited to, ligase chain reaction (LCR; see Wu and Wallace (1989) *Genomics* 4:560-569; Landegren, et al. (1988) *Science* 241:1077-1980; and Barringer, et al. (1990) *Gene* 89:117-122), transcription amplification (Kwoh, et al. (1989) *Proc. Nat'l Acad. Sci. USA* 86:1173-1177), self-sustained sequence replication (Guatelli, et al. (1990) *Proc. Nat'l Acad. Sci. USA* 87:1874-1878), dot PCR, linker adapter PCR, etc.

Expression of Ovarian Cancer Proteins from Nucleic Acids

In a preferred embodiment, ovarian cancer nucleic acids, e.g., encoding ovarian cancer proteins are used to make a variety of expression vectors to express ovarian cancer proteins which can then be used in screening assays, as described below. Expression vectors and recombinant DNA technology are well known and are used to express proteins. See, e.g., Ausubel, supra; and Fernandez and Hoeffler (eds. 1999) *Gene Expression Systems* Academic Press. The expression vectors may be either self-replicating extrachromosomal vectors or vectors which integrate into a host genome. Generally, these expression vectors include transcriptional and translational regulatory nucleic acid operably linked to the nucleic acid encoding the ovarian cancer protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; a ribosome binding site is operably linked to a coding sequence if it is positioned so as to facilitate translation; and two sequences may be operably linked when they are physically part of the same polymer. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the ovarian cancer protein. Numerous types of appropriate expression vectors, and suitable regulatory sequences are known in the art for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences typically encode constitutive or inducible promoters. The promoters may be naturally occurring promoters or hybrid promoters. Hybrid promoters, which combine elements of more than one promoter, are also known in the art, and are useful in the present invention.

In addition, an expression vector may comprise additional elements. For example, the expression vector may have two replication systems, thus allowing it to be maintained in two organisms, e.g., in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are available. See, e.g., Fernandez and Hoeffler, supra.

In addition, in a preferred embodiment, the expression vector contains a selectable marker gene to allow the selection of transformed host cells. Selection genes are well known in the art and will vary with the host cell used.

The ovarian cancer proteins of the present invention are produced by culturing a host cell transformed with an expression vector containing nucleic acid encoding an ovarian cancer protein, under the appropriate conditions to induce or cause expression of the ovarian cancer protein. Conditions appropriate for ovarian cancer protein expression will vary with the choice of the expression vector and the host cell, and will be easily ascertained by one skilled in the art through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculovirus systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, *Neurospora*, BHK, CHO, COS, HeLa cells, HUVEC (human umbilical vein endothelial cells), THP1 cells (a macrophage cell line) and various other human cells and cell lines.

In a preferred embodiment, the ovarian cancer proteins are expressed in mammalian cells. Mammalian expression systems are also known in the art, and include retroviral and adenoviral systems. One expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. See, e.g., Fernandez and Hoeffler, supra. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, ovarian cancer proteins are expressed in bacterial systems. Bacterial expression systems are well known in the art. Promoters from bacteriophage may also be used and are known in the art. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the ovarian cancer protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin, and tetracycline. Selectable markers also include biosynthetic genes, such as those in the histidine, tryptophan, and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans,* among others. See Fernandez and Hoeffler, supra. The bacterial expression vectors are transformed into bacterial host cells using techniques well known in the art, such as calcium chloride treatment, electroporation, and others.

In one embodiment, ovarian cancer proteins are produced in insect cells. Expression vectors for the transformation of insect cells, and in particular, baculovirus-based expression vectors, are well known in the art.

In a preferred embodiment, an ovarian cancer protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.*

The ovarian cancer protein may also be made as a fusion protein, using techniques well known in the art. Thus, e.g., for the creation of monoclonal antibodies, if the desired epitope is small, the ovarian cancer protein may be fused to a carrier protein to form an immunogen. Alternatively, the ovarian cancer protein may be made as a fusion protein to increase expression, or for other reasons. For example, when the ovarian cancer protein is an ovarian cancer peptide, the nucleic acid encoding the peptide may be linked to other nucleic acid for expression purposes.

In a preferred embodiment, the ovarian cancer protein is purified or isolated after expression. Ovarian cancer proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the ovarian cancer protein may be purified using a standard anti-ovarian cancer protein antibody column. Ultrafiltration and diafiltration techniques, in conjunction with protein concentration, are also useful. For general guidance in suitable purification techniques, see Scopes (1982) *Protein Purification* Springer-Verlag. The degree of purification necessary will vary depending on the use of the ovarian cancer protein. In some instances no purification will be necessary.

Once expressed and purified if necessary, the ovarian cancer proteins and nucleic acids are useful in a number of applications. They may be used as immunoselection reagents, as vaccine reagents, as screening agents, etc.

Variants of Ovarian Cancer Proteins

In one embodiment, the ovarian cancer proteins are derivative or variant ovarian cancer proteins as compared to the wild-type sequence. That is, as outlined more fully below, the derivative ovarian cancer peptide will often contain at least one amino acid substitution, deletion or insertion, with amino acid substitutions being particularly preferred. The amino acid substitution, insertion, or deletion may occur at most any residue within the ovarian cancer peptide.

Also included within one embodiment of ovarian cancer proteins of the present invention are amino acid sequence variants. These variants typically fall into one or more of three classes: substitutional, insertional or deletional variants. These variants ordinarily are prepared by site specific mutagenesis of nucleotides in the DNA encoding the ovarian cancer protein, using cassette or PCR mutagenesis or other techniques well known in the art, to produce DNA encoding the variant, and thereafter expressing the DNA in recombinant cell culture as outlined above. However, variant ovarian cancer protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the ovarian cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed ovarian cancer variants screened for the optimal combination of desired activity. Techniques for making substitution mutations at predetermined sites in DNA having a known sequence are well known, e.g., M13 primer mutagenesis and PCR mutagenesis. Screening of the mutants is done using assays of ovarian cancer protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the ovarian cancer protein are desired, substitutions are generally made in accordance with the amino acid substitution relationships provided in the definition section.

The variants typically exhibit the same qualitative biological activity and will elicit the same immune response as the naturally-occurring analog, although variants also are selected to modify the characteristics of the ovarian cancer proteins as needed. Alternatively, the variant may be designed such that the biological activity of the ovarian cancer protein is altered. For example, glycosylation sites may be altered or removed.

Substantial changes in function or immunological identity are made by selecting substitutions that are less conservative than those described above. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., serine or threonine is substituted for (or by) a hydrophobic residue, e.g., leucine, isoleucine, phenylalanine, valine, or alanine; (b) a cysteine or proline is substituted for (or by) any other residue; (c) a residue having an electropositive side chain, e.g., lysine, arginine, or histidine, is substituted for (or by) an electronegative residue, e.g., glutamic or aspartic acid; (d) a residue having a bulky side chain, e.g., phenylalanine, is substituted for (or by) one not having a side chain, e.g., glycine; or (e) a proline residue is incorporated or substituted, which changes the degree of rotational freedom of the peptidyl bond.

Covalent modifications of ovarian cancer polypeptides are included within the scope of this invention. One type of covalent modification includes reacting targeted amino acid residues of an ovarian cancer polypeptide with an organic derivatizing agent that is capable of reacting with selected side chains or the N-or C-terminal residues of an ovarian cancer polypeptide. Derivatization with bifunctional agents is useful, for instance, for crosslinking ovarian cancer polypeptides to a water-insoluble support matrix or surface for use in the method for purifying anti-ovarian cancer polypeptide antibodies or screening assays, as is more fully described below. Commonly used crosslinking agents include, e.g., 1,1-bis(diazoacetyl)-2-phenylethane, glutaraldehyde, N-hydroxysuccinimide esters, e.g., esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio) propioimidate.

Other modifications include deamidation of glutamine and asparagine residues to the corresponding glutamic and aspartic acid residues, respectively, hydroxylation of proline and lysine, phosphorylation of hydroxyl groups of serine, threonine, or tyrosine residues, methylation of the amino groups of the lysine, arginine, and histidine side chains (e.g., pp. 79-86, Creighton (1983) *Proteins: Structure and Molecular Properties* Freeman), acetylation of the N-terminal amine, and amidation of a C-terminal carboxyl group.

Another type of covalent modification of the ovarian cancer polypeptide included within the scope of this invention comprises altering the native glycosylation pattern of the polypeptide. "Altering the native glycosylation pattern" is intended for purposes herein to mean deleting one or more carbohydrate moieties found in native sequence ovarian cancer polypeptide, and/or adding one or more glycosylation sites that are not present in the native sequence ovarian cancer polypeptide. Glycosylation patterns can be altered in many ways. For example the use of different cell types to express ovarian cancer-associated sequences can result in different glycosylation patterns.

Addition of glycosylation sites to ovarian cancer polypeptides may also be accomplished by altering the amino acid sequence thereof. The alteration may be made, e.g., by the addition of, or substitution by, one or more serine or threonine residues to the native sequence ovarian cancer polypeptide (for O-linked glycosylation sites). The ovarian cancer amino acid sequence may optionally be altered through changes at the DNA level, particularly by mutating the DNA encoding the ovarian cancer polypeptide at pre-selected bases such that codons are generated that will translate into the desired amino acids.

Another means of increasing the number of carbohydrate moieties on the ovarian cancer polypeptide is by chemical or enzymatic coupling of glycosides to the polypeptide. See, e.g., WO 87/05330, and pp. 259-306 in Aplin and Wriston (1981) *CRC Crit. Rev. Biochem*. CRC Press.

Removal of carbohydrate moieties present on the ovarian cancer polypeptide may be accomplished chemically or enzymatically or by mutational substitution of codons encoding for amino acid residues that serve as targets for glycosylation. Chemical deglycosylation techniques are applicable. See, e.g., Sojar and Bahl (1987) *Arch. Biochem. Biophys*. 259:52-57; and Edge, et al. (1981) *Anal. Biochem*. 118:131-137. Enzymatic cleavage of carbohydrate moieties on polypeptides can be achieved by the use of a variety of endo-and exo-glycosidases. See, e.g., Thotakura, et al. (1987) *Meth. Enzymol.*, 138:350-359.

Another type of covalent modification of ovarian cancer comprises linking the ovarian cancer polypeptide to one of a variety of non-proteinaceous polymers, e.g., polyethylene glycol, polypropylene glycol, or polyoxyalkylene. See, e.g., U.S. Pat. No. 4,640,835; 4,496,689; 4,301,144; 4,670,417; 4,791,192; or 4,179,337.

Ovarian cancer polypeptides of the present invention may also be modified in a way to form chimeric molecules, e.g., comprising an ovarian cancer polypeptide fused to another heterologous polypeptide or amino acid sequence. In one embodiment, such a chimeric molecule comprises a fusion of an ovarian cancer polypeptide with a tag polypeptide which provides an epitope to which an anti-tag antibody can selectively bind. The epitope tag is generally placed at the amino-or carboxyl-terminus of the ovarian cancer polypeptide. The presence of such epitope-tagged forms of an ovarian cancer polypeptide can be detected using an antibody against the tag polypeptide. Also, provision of the epitope tag enables the ovarian cancer polypeptide to be readily purified by affinity purification using an anti-tag antibody or another type of affinity matrix that binds to the epitope tag. In an alternative embodiment, the chimeric molecule may comprise a fusion of an ovarian cancer polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; His6 and metal chelation tags, the flu HA tag polypeptide and its antibody 12CA5 (Field, et al. (1988) *Mol. Cell. Biol*. 8:2159-2165); the c-myc tag and the 8F9, 3C7, 6E10, G4, B7, and 9E10 antibodies thereto (Evan, et al. (1985) *Mol. Cell. Biol*. 5:3610-3616); and the Herpes Simplex virus glycoprotein D (gD) tag and its antibody (Paborsky, et al. (1990) *Protein*

Engineering 3:547-553). Other tag polypeptides include, e.g., the Flag-peptide (Hopp, et al. (1988) BioTechnology 6:1204-1210); the KT3 epitope peptide (Martin, et al. (1992) Science 255:192-194); tubulin epitope peptide (Skinner, et al. (1991) J. Biol. Chem. 266:15163-15166); and the T7 gene 10 protein peptide tag (Lutz-Freyermuth et al. (1990) Proc. Nat'l Acad. Sci. USA 87:6393-6397).

Also included are other ovarian cancer proteins of the ovarian cancer family, and ovarian cancer proteins from other organisms, which are cloned and expressed as outlined below. Thus, probe or degenerate polymerase chain reaction (PCR) primer sequences may be used to find other related ovarian cancer proteins from humans or other organisms. As will be appreciated by those in the art, particularly useful probe and/or PCR primer sequences include the unique areas of the ovarian cancer nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art (e.g., Innis, PCR Protocols, supra).

Antibodies to Ovarian Cancer Proteins

In a preferred embodiment, when the ovarian cancer protein is to be used to generate antibodies, e.g., for immunotherapy or immunodiagnosis, the ovarian cancer protein should share at least one epitope or determinant with the full length protein. By "epitope" or "determinant" herein is typically meant a portion of a protein which will generate and/or bind an antibody or T-cell receptor in the context of MHC. Thus, in most instances, antibodies made to a smaller ovarian cancer protein will be able to bind to the full-length protein, particularly linear epitopes. In a preferred embodiment, the epitope is unique; that is, antibodies generated to a unique epitope show little or no cross-reactivity.

Methods of preparing polyclonal antibodies are known to the skilled artisan (e.g., Coligan, supra; and Harlow and Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of the figures or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein (1975) Nature 256:495-497. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of Table 19A or fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (e.g., pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for a protein encoded by a nucleic acid Table 1-20 or a fragment thereof, the other one is for any other antigen, and preferably for a cell-surface protein or receptor or receptor subunit, preferably one that is tumor specific. Alternatively, tetramer-type technology may create multivalent reagents.

In a preferred embodiment, the antibodies to ovarian cancer protein are capable of reducing or eliminating a biological function of an ovarian cancer protein, as is described below. That is, the addition of anti-ovarian cancer protein antibodies (either polyclonal or preferably monoclonal) to ovarian cancer tissue (or cells containing ovarian cancer) may reduce or eliminate the ovarian cancer. Generally, at least a 25% decrease in activity, growth, size or the like is preferred, with at least about 50% being particularly preferred and about a 95-100% decrease being especially preferred.

In a preferred embodiment the antibodies to the ovarian cancer proteins are humanized antibodies (e.g., Xenerex Biosciences; Medarex, Inc.; Abgenix, Inc.; Protein Design Labs, Inc.) Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin. Humanization can be essentially performed following the method of Winter and co-workers, e.g., by substituting rodent CDRs or CDR sequences for the corresponding sequences of a human antibody. See, e.g., Jones, et al. (1986) Nature 321:522-525; Riechmann, et al. (1988) Nature 332:323-329; Presta (1992) Curr. Op. Struct. Biol. 2:593-596; and Verhoeyen, et al. (1988) Science 239:1534-1536). Accordingly, such humanized antibodies are chimeric antibodies (U.S. Pat. No. 4,816, 567), wherein substantially less than an intact human variable domain has been substituted by the corresponding sequence from a non-human species.

Human antibodies can also be produced using various techniques known in the art, including phage display libraries (see, e.g., Hoogenboom and Winter (1991) *J. Mol. Biol.* 227: 381-388; and Marks, et al. (1991) *J. Mol. Biol.* 222:581-597) or human monoclonal antibodies (see, e.g., p. 77, Cole, et al. in Reisfeld and Sell (1985) *Monoclonal Antibodies and Cancer Therapy* Liss; and Boerner, et al. (1991) *J. Immunol.* 147:86-95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. See, e.g., U.S. Pat. Nos. 5,545,807; 5,545,806; 5,569,825; 5,625,126; 5,633,425; 5,661,016; Marks, et al. (1992) *Bio/Technology* 10:779-783; Lonberg, et al. (1994) *Nature* 368: 856-859; Morrison (1994) *Nature* 368:812-13; Neuberger (1996) *Nature Biotechnology* 14:826 commenting on Fishwild, et al. (1996) *Nature Biotechnology* 14:845-51; and Lonberg and Huszar (1995) *Intern. Rev. Immunol.* 13:65-93.

By immunotherapy is meant treatment of ovarian cancer, e.g., with an antibody raised against ovarian cancer proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. The antigen may be provided by injecting a polypeptide against which antibodies are desired to be raised into a recipient, or contacting the recipient with a nucleic acid capable of expressing the antigen and under conditions for expression of the antigen, leading to an immune response.

In a preferred embodiment the ovarian cancer proteins against which antibodies are raised are secreted proteins as described above. Without being bound by theory, antibodies used for treatment, bind and prevent the secreted protein from binding to its receptor, thereby inactivating the secreted ovarian cancer protein.

In another preferred embodiment, the ovarian cancer protein to which antibodies are raised is a transmembrane protein. Without being bound by theory, antibodies used for treatment, bind the extracellular domain of the ovarian cancer protein and prevent it from binding to other proteins, such as circulating ligands or cell-associated molecules. The antibody may cause down-regulation of the transmembrane ovarian cancer protein. As will be appreciated by one of ordinary skill in the art, the antibody may be a competitive, non-competitive or uncompetitive inhibitor of protein binding to the extracellular domain of the ovarian cancer protein. The antibody is also an antagonist of the ovarian cancer protein. Further, the antibody prevents activation of the transmembrane ovarian cancer protein. In one aspect, when the antibody prevents the binding of other molecules to the ovarian cancer protein, the antibody prevents growth of the cell. The antibody may also be used to target or sensitize the cell to cytotoxic agents, including, but not limited to TNF-α, TNF-β, IL-1, INF-γ, and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity or antigen-dependent cytotoxicity (ADCC). Thus, ovarian cancer is treated by administering to a patient antibodies directed against the transmembrane ovarian cancer protein. Antibody-labeling may activate a co-toxin, localize a toxin payload, or otherwise provide means to locally ablate cells.

In another preferred embodiment, the antibody is conjugated to an effector moiety. The effector moiety can be any number of molecules, including labeling moieties such as radioactive labels or fluorescent labels, or can be a therapeutic moiety. In one aspect the therapeutic moiety is a small molecule that modulates the activity of the ovarian cancer protein. In another aspect the therapeutic moiety modulates the activity of molecules associated with or in close proximity to the ovarian cancer protein. The therapeutic moiety may inhibit enzymatic activity such as protease or collagenase or protein kinase activity associated with ovarian cancer.

In a preferred embodiment, the therapeutic moiety can also be a cytotoxic agent. In this method, targeting the cytotoxic agent to ovarian cancer tissue or cells, results in a reduction in the number of afflicted cells, thereby reducing symptoms associated with ovarian cancer. Cytotoxic agents are numerous and varied and include, but are not limited to, cytotoxic drugs or toxins or active fragments of such toxins. Suitable toxins and their corresponding fragments include diphtheria A chain, exotoxin A chain, ricin A chain, abrin A chain, curcin, crotin, phenomycin, enomycin and the like. Cytotoxic agents also include radiochemicals made by conjugating radioisotopes to antibodies raised against ovarian cancer proteins, or binding of a radionuclide to a chelating agent that has been covalently attached to the antibody. Targeting the therapeutic moiety to transmembrane ovarian cancer proteins not only serves to increase the local concentration of therapeutic moiety in the ovarian cancer afflicted area, but also serves to reduce deleterious side effects that may be associated with the untargeted therapeutic moiety.

In another preferred embodiment, the ovarian cancer protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the ovarian cancer protein can be targeted within a cell, e.g., the nucleus, an antibody thereto contains a signal for that target localization, e.g., a nuclear localization signal.

The ovarian cancer antibodies of the invention specifically bind to ovarian cancer proteins. By "specifically bind" herein is meant that the antibodies bind to the protein with a $K_d$ of at least about 0.1 mM, more usually at least about 1 µM, preferably at least about 0.1 µM or better, and most preferably, 0.01 µM or better. Selectivity of binding is also important.

Detection of Ovarian Cancer Sequence for Diagnostic and Therapeutic Applications In one aspect, the RNA expression levels of genes are determined for different cellular states in the ovarian cancer phenotype. Expression levels of genes in normal tissue (e.g., not undergoing ovarian cancer) and in ovarian cancer tissue (and in some cases, for varying severities of ovarian cancer that relate to prognosis, as outlined below, or in non-malignant disease are evaluated to provide expression profiles. An expression profile of a particular cell state or point of development is essentially a "fingerprint" of the state of the cell. While two states may have any particular gene similarly expressed, the evaluation of a number of genes simultaneously allows the generation of a gene expression profile that is reflective of the state of the cell. By comparing expression profiles of cells in different states, information regarding which genes are important (including both up- and down-regulation of genes) in each of these states is obtained. Then, diagnosis may be performed or confirmed to determine whether a tissue sample has the gene expression profile of normal or cancerous tissue. This will provide for molecular diagnosis of related conditions.

"Differential expression," or grammatical equivalents as used herein, refers to qualitative or quantitative differences in the temporal and/or cellular gene expression patterns within and among cells and tissue. Thus, a differentially expressed gene can qualitatively have its expression altered, including an activation or inactivation, in, e.g., normal versus ovarian cancer tissue. Genes may be turned on or turned off in a particular state, relative to another state thus permitting comparison of two or more states. A qualitatively regulated gene will exhibit an expression pattern within a state or cell type which is detectable by standard techniques. Some genes will be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques as outlined below, such as by use of Affymetrix GeneChip™ expression arrays. See, e.g., Lockhart (1996) *Nature Biotechnology* 14:1675-1680. Other techniques include, but are not limited to, quantitative reverse transcriptase PCR, northern analysis, and RNase protection. As outlined above, preferably the change in expression (e.g., up-regulation or down-regulation) is at least about 50%, more preferably at least about 100%, more preferably at least about 150%, more preferably at least about 200%, with from 300 to at least 1000% being especially preferred.

Evaluation may be at the gene transcript, or the protein level. The amount of gene expression may be monitored using nucleic acid probes to the DNA or RNA equivalent of the gene transcript, and the quantification of gene expression levels, or, alternatively, the final gene product itself (protein) can be monitored, e.g., with antibodies to the ovarian cancer protein and standard immunoassays (ELISAs, etc.) or other techniques, including mass spectroscopy assays, 2D gel electrophoresis assays, etc. Proteins corresponding to ovarian cancer genes, e.g., those identified as being important in an ovarian cancer or disease phenotype, can be evaluated in an ovarian disease diagnostic test. In a preferred embodiment, gene expression monitoring is performed simultaneously on a number of genes. Multiple protein expression monitoring can be performed, or on an individual basis.

In this embodiment, the ovarian cancer nucleic acid probes are attached to biochips as outlined herein for the detection and quantification of ovarian cancer sequences in a particular sample. The assays are further described below in the example. PCR techniques can be used to provide greater sensitivity.

In a preferred embodiment nucleic acids encoding the ovarian cancer protein are detected. Although DNA or RNA encoding the ovarian cancer protein may be detected, of particular interest are methods wherein an mRNA encoding an ovarian cancer protein is detected. Probes to detect mRNA can be a nucleotide/deoxynucleotide probe that is complementary to and hybridizes with the mRNA and includes, but is not limited to, oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an ovarian cancer protein is detected by binding the digoxygenin with an anti-digoxygenin secondary antibody and developed with nitro blue tetrazolium and 5-bromo-4-chloro-3-indoyl phosphate.

In a preferred embodiment, various proteins from the three classes of proteins as described herein (secreted, transmembrane or intracellular proteins) are used in diagnostic assays. The ovarian cancer proteins, antibodies, nucleic acids, modified proteins and cells containing ovarian cancer sequences are used in diagnostic assays. This can be performed on an individual gene or corresponding polypeptide level. In a preferred embodiment, the expression profiles are used, preferably in conjunction with high throughput screening techniques to allow monitoring for expression profile genes and/or corresponding polypeptides.

As described and defined herein, ovarian cancer proteins, including intracellular, transmembrane, or secreted proteins, find use as prognostic or diagnostic markers of ovarian disease. Detection of these proteins in putative ovarian cancer tissue allows for detection, diagnosis, or prognosis of ovarian disease, and for selection of therapeutic strategy. In one embodiment, antibodies are used to detect ovarian cancer proteins. A preferred method separates proteins from a sample by electrophoresis on a gel (typically a denaturing and reducing protein gel, but may be another type of gel, including isoelectric focusing gels and the like). Following separation of proteins, the ovarian cancer protein is detected, e.g., by immunoblotting with antibodies raised against the ovarian cancer protein. Methods of immunoblotting are well known to those of ordinary skill in the art.

In another preferred method, antibodies to the ovarian cancer protein find use in in situ imaging techniques, e.g., in histology. See, e.g., Asai (ed. 1993) *Methods in Cell Biology: Antibodies in Cell Biology* (vol. 37) Academic Press. Cells are contacted with from one to many antibodies to the ovarian cancer protein(s). Following washing to remove non-specific antibody binding, the presence of the antibody or antibodies is detected. In one embodiment the antibody is detected by incubating with a secondary antibody that contains a detectable label. In another method the primary antibody to the ovarian cancer protein(s) contains a detectable label, e.g., an enzyme marker that can act on a substrate. In another preferred embodiment each one of multiple primary antibodies contains a distinct and detectable label. This method finds particular use in simultaneous screening for a plurality of ovarian cancer proteins. As will be appreciated by one of ordinary skill in the art, many other histological imaging techniques are also provided by the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing ovarian cancer from blood, serum, plasma, stool, and other samples. Such samples, therefore, are useful as samples to be probed or tested for the presence of ovarian cancer proteins. Antibodies can be used to detect an ovarian cancer protein by previously described immunoassay techniques including ELISA, immunoblotting (western blotting), immunoprecipitation, BIACORE technology, and the like. Conversely, the presence of antibodies may indicate an immune response against an endogenous ovarian cancer protein.

In a preferred embodiment, in situ hybridization of labeled ovarian cancer nucleic acid probes to tissue arrays is done. For example, arrays of tissue samples, including ovarian cancer tissue and/or normal tissue, are made. In situ hybridization (see, e.g., Ausubel, supra) is then performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

In a preferred embodiment, the ovarian cancer proteins, antibodies, nucleic acids, modified proteins and cells containing ovarian cancer sequences are used in prognosis assays. As above, gene expression profiles can be generated that correlate to ovarian cancer, clinical, pathological, or other information, in terms of long term prognosis. Again, this may be done on either a protein or gene level, with the use of a plurality of genes being preferred. As above, ovarian cancer probes may be attached to biochips for the detection and quantification of ovarian cancer sequences in a tissue or patient. The assays proceed as outlined above for diagnosis. PCR method may provide more sensitive and accurate quantification.

Assays for Therapeutic Compounds

In a preferred embodiment members of the proteins, nucleic acids, and antibodies as described herein are used in drug screening assays. The ovarian cancer proteins, antibodies, nucleic acids, modified proteins and cells containing ovarian cancer sequences are used in drug screening assays or by evaluating the effect of drug candidates on a "gene expression profile" or expression profile of polypeptides. In a preferred embodiment, the expression profiles are used, preferably in conjunction with high throughput screening techniques to allow monitoring for expression profile genes after treatment with a candidate agent. See, e.g., Zlokarnik, et al. (1998) Science 279:84-88; and Heid (1996) Genome Res. 6:986-994.

In a preferred embodiment, the ovarian cancer proteins, antibodies, nucleic acids, modified proteins and cells containing the native or modified ovarian cancer proteins are used in screening assays. That is, the present invention provides novel methods for screening for compositions which modulate the ovarian cancer phenotype or an identified physiological function of an ovarian cancer protein. As above, this can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent. See, e.g., Zlokarnik, supra.

Having identified the differentially expressed genes herein, a variety of assays may be executed. In a preferred embodiment, assays may be run on an individual gene or protein level. That is, having identified a particular gene as up regulated in ovarian cancer, test compounds can be screened for the ability to modulate gene expression or for binding to the ovarian cancer protein. "Modulation" thus includes both an increase and a decrease in gene expression. The preferred amount of modulation will depend on the original change of the gene expression in normal versus tissue undergoing ovarian cancer, with changes of at least 10%, preferably 50%, more preferably 100-300%, and in some embodiments 300-1000% or greater. Thus, if a gene exhibits a 4-fold increase in ovarian cancer tissue compared to normal tissue, a decrease of about four-fold is often desired; similarly, a 10-fold decrease in ovarian cancer tissue compared to normal tissue often provides a target value of a 10-fold increase in expression to be induced by the test compound.

The amount of gene expression may be monitored using nucleic acid probes and the quantification of gene expression levels, or, alternatively, the gene product itself can be monitored, e.g., through the use of antibodies to the ovarian cancer protein and standard immunoassays. Proteomics and separation techniques may also allow quantification of expression.

In a preferred embodiment, gene expression or protein monitoring of a number of entities, e.g., an expression profile, is monitored simultaneously. Such profiles will typically involve a plurality of those entities described herein.

In this embodiment, the ovarian cancer nucleic acid probes are attached to biochips as outlined herein for the detection and quantification of ovarian cancer sequences in a particular cell. Alternatively, PCR may be used. Thus, a series, e.g., of microtiter plate, may be used with dispensed primers in desired wells. A PCR reaction can then be performed and analyzed for each well.

Expression monitoring can be performed to identify compounds that modify the expression of one or more ovarian cancer-associated sequences, e.g., a polynucleotide sequence set out in Tables 1-20. Generally, in a preferred embodiment, a test modulator is added to the cells prior to analysis. Moreover, screens are also provided to identify agents that modulate ovarian cancer, modulate ovarian cancer proteins, bind to an ovarian cancer protein, or interfere with the binding of an ovarian cancer protein and an antibody or other binding partner.

The term "test compound" or "drug candidate" or "modulator" or grammatical equivalents as used herein describes any molecule, e.g., protein, oligopeptide, small organic molecule, polysaccharide, polynucleotide, etc., to be tested for the capacity to directly or indirectly alter the ovarian cancer phenotype or the expression of an ovarian cancer sequence, e.g., a nucleic acid or protein sequence. In preferred embodiments, modulators alter expression profiles, or expression profile nucleic acids or proteins provided herein. In one embodiment, the modulator suppresses an ovarian cancer phenotype, e.g., to a normal or non-malignant tissue fingerprint. In another embodiment, a modulator induced an ovarian cancer phenotype. Generally, a plurality of assay mixtures are run in parallel with different agent concentrations to obtain a differential response to the various concentrations. Typically, one of these concentrations serves as a negative control, e.g., at zero concentration or below the level of detection.

Drug candidates encompass numerous chemical classes, though typically they are organic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

In one aspect, a modulator will neutralize the effect of an ovarian cancer protein. By "neutralize" is meant that activity of a protein is inhibited or blocked and the consequent effect on the cell.

In certain embodiments, combinatorial libraries of potential modulators will be screened for an ability to bind to an ovarian cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

In one preferred embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (e.g., the number of amino acids in a polypeptide compound). Millions of chemical compounds can be synthesized through such combinatorial mixing of chemical building blocks. See, e.g., Gallop, et al. (1994) *J. Med. Chem.* 37:1233-1251.

Preparation and screening of combinatorial chemical libraries is well known to those of skill in the art. Such combinatorial chemical libraries include, but are not limited to, peptide libraries (see, e.g., U.S. Pat. No. 5,010,175; Furka (1991) *Pept. Prot. Res.* 37:487-493; and Houghton, et al. (1991) *Nature* 354:84-88), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs, et al. (1993) *Proc. Nat'l Acad. Sci. USA* 90:6909-913), vinylogous polypeptides (Hagihara, et al. (1992) *J. Amer. Chem. Soc.* 114:6568-570), non-peptidal peptidomimetics with a Beta-D-Glucose scaffolding (Hirschmann, et al. (1992) *J. Amer. Chem. Soc.* 114:9217-218), analogous organic syntheses of small compound libraries (Chen, et al. (1994) *J. Amer. Chem. Soc.* 116:2661-662), oligocarbamates (Cho, et al. (1993) *Science* 261:1303-305), and/or peptidyl phosphonates (Campbell, et al. (1994) *J. Org. Chem.* 59:658-xxx). See, generally, Gordon, et al. (1994) *J. Med. Chem.* 37:1385-401, nucleic acid libraries (see, e.g., Stratagene, Corp.), peptide nucleic acid libraries (see, e.g., U.S. Pat. No. 5,539,083), antibody libraries (see, e.g., Vaughn, et al. (1996) *Nature Biotechnology* 14:309-314; and PCT/US96/10287), carbohydrate libraries (see, e.g., Liang, et al. (1996) *Science* 274:1520-1522; and U.S. Pat. No. 5,593,853), and small organic molecule libraries (see, e.g., benzodiazepines, page 33, Baum (Jan. 18, 1993) *C&E News*; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514; and the like).

Devices for the preparation of combinatorial libraries are commercially available. See, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tripos, Inc., St. Louis, Mo.; ChemStar, Ltd, Moscow, RU; 3D Pharmaceuticals, Exton, Pa.; Martek Biosciences, Columbia, Md.; etc.).

The assays to identify modulators are amenable to high throughput screening. Preferred assays thus detect enhancement or inhibition of ovarian cancer gene transcription, inhibition or enhancement of polypeptide expression, and inhibition or enhancement of polypeptide activity.

High throughput assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins, U.S. Pat. No. 5,585,639 discloses high throughput screening methods for nucleic acid binding (e.g., in arrays), while U.S. Pat. Nos. 5,576,220 and 5,541,061 disclose high throughput methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

In one embodiment, modulators are proteins, often naturally occurring proteins or fragments of naturally occurring proteins. Thus, e.g., cellular extracts containing proteins, or random or directed digests of proteinaceous cellular extracts, may be used. In this way libraries of proteins may be made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes or ligands and receptors.

In a preferred embodiment, modulators are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

Modulators of ovarian cancer can also be nucleic acids, as defined above.

As described above generally for proteins, nucleic acid modulating agents may be naturally occurring nucleic acids, random nucleic acids, or "biased" random nucleic acids. For example, digests of procaryotic or eucaryotic genomes may be used as is outlined above for proteins.

In a preferred embodiment, the candidate compounds are organic chemical moieties, a wide variety of which are available in the literature.

After the candidate agent has been added and the cells allowed to incubate for some period of time, the sample containing a target sequence to be analyzed is added to the biochip. If required, the target sequence is prepared using known techniques. For example, the sample may be treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

In a preferred embodiment, the target sequence is labeled with, e.g., a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways. Components of the reaction may be added simultaneously, or sequentially, in different orders, with preferred embodiments outlined below. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors, anti-microbial agents, etc., may also be used as appropriate, depending on the sample preparation methods and purity of the target.

The assay data are analyzed to determine the expression levels, and changes in expression levels as between states, of individual genes, forming a gene expression profile.

Screens are performed to identify modulators of the ovarian cancer phenotype. In one embodiment, screening is performed to identify modulators that can induce or suppress a particular expression profile, thus preferably generating the associated phenotype. In another embodiment, e.g., for diagnostic applications, having identified differentially expressed genes important in a particular state, screens can be performed to identify modulators that alter expression of individual genes. In an another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition screens can be done for genes that are induced in response to a candidate agent. After identifying a modulator based upon its ability to suppress an ovarian cancer expression pattern leading to a normal expression pattern, or to modulate a single ovarian cancer gene expression profile so as to mimic the expression of the gene from normal tissue, a screen as described above can be performed to identify genes that are specifically modulated in response to the agent. Comparing expression profiles between normal tissue and agent treated ovarian cancer tissue reveals genes that are not expressed in normal tissue or ovarian cancer tissue, but are expressed in agent treated tissue. These agent-specific sequences can be identified and used by methods described herein for ovarian cancer genes or proteins. In particular these sequences and the proteins they encode find use in marking or identifying agent treated cells. In addition, antibodies can be raised against the agent induced proteins and used to target novel therapeutics to the treated ovarian cancer tissue sample.

Thus, in one embodiment, a test compound is administered to a population of ovarian cancer cells, that have an associated ovarian cancer expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (e.g., a peptide) may be put into a viral construct such as an adenoviral or retroviral construct, and added to the cell, such that expression of the peptide agent is accomplished, e.g., PCT US97/01019. Regulatable gene therapy systems can also be used.

Once the test compound has been administered to the cells, the cells can be washed if desired and are allowed to incubate under preferably physiological conditions for some period of time. The cells are then harvested and a new gene expression profile is generated, as outlined herein.

Thus, e.g., ovarian cancer or non-malignant tissue may be screened for agents that modulate, e.g., induce or suppress the ovarian cancer phenotype. A change in at least one gene, preferably many, of the expression profile indicates that the agent has an effect on ovarian cancer activity. By defining such a signature for the ovarian cancer phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular differentially expressed gene as important in a particular state, screening of modulators of either the expression of the gene or the gene product itself can be done. The gene products of differentially expressed genes are sometimes referred to herein as "ovarian cancer proteins" or a "ovarian cancer modulatory protein". The ovarian cancer modulatory protein may be a fragment, or alternatively, be the full length protein to the fragment encoded by the nucleic acids of the Tables. Preferably, the ovarian cancer modulatory protein is a fragment. In a preferred embodiment, the ovarian cancer amino acid sequence which is used to determine sequence identity or similarity is encoded by a nucleic acid of the Tables. In another embodiment, the sequences are naturally occurring allelic variants of a protein encoded by a nucleic acid of the Tables. In another embodiment, the sequences are sequence variants as further described herein.

Preferably, the ovarian cancer modulatory protein is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In another embodiment, the C-terminus of the fragment is kept as a free acid and the N-terminus is a free amine to aid in coupling, e.g., to cysteine. Or, the ovarian cancer proteins are conjugated to an immunogenic agent, e.g., to BSA.

Measurements of ovarian cancer polypeptide activity, or of ovarian cancer or the ovarian cancer phenotype can be performed using a variety of assays. For example, the effects of the test compounds upon the function of the ovarian cancer polypeptides can be measured by examining parameters described above. A suitable physiological change that affects activity can be used to assess the influence of a test compound on the polypeptides of this invention. When the functional consequences are determined using intact cells or animals, one can also measure a variety of effects such as, in the case of ovarian cancer associated with tumors, tumor growth, tumor metastasis, neovascularization, hormone release, transcriptional changes to both known and uncharacterized genetic markers (e.g., northern blots), changes in cell metabolism such as cell growth or pH changes, and changes in intracellular second messengers such as cGMP. In the assays of the invention, mammalian ovarian cancer polypeptide is typically used, e.g., mouse, preferably human.

Assays to identify compounds with modulating activity can be performed in vitro. For example, an ovarian cancer polypeptide is first contacted with a potential modulator and incubated for a suitable amount of time, e.g., from 0.5 to 48 hours. In one embodiment, the ovarian cancer polypeptide levels are determined in vitro by measuring the level of protein or mRNA. The level of protein is measured using immunoassays such as western blotting, ELISA and the like with an antibody that selectively binds to the ovarian cancer polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the ovarian cancer protein promoter operably linked to a reporter gene such as luciferase, green fluorescent protein, CAT, or β-gal. The reporter construct is typically transfected into a cell. After treatment with a potential modulator, the amount of reporter gene transcription, translation, or activity is measured according to standard techniques known to those of skill in the art.

In a preferred embodiment, as outlined above, screens may be done on individual genes and gene products (proteins). That is, having identified a particular differentially expressed gene as important in a particular state, screening of modulators of the expression of the gene or the gene product itself can be done. The gene products of differentially expressed genes are sometimes referred to herein as "ovarian cancer proteins." The ovarian cancer protein may be a fragment, or alternatively, be the full length protein to a fragment shown herein.

In one embodiment, screening for modulators of expression of specific genes is performed. Typically, the expression of only one or a few genes are evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

In a preferred embodiment, binding assays are done. In general, purified or isolated gene product is used; that is, the gene products of one or more differentially expressed nucleic acids are made. For example, antibodies are generated to the protein gene products, and standard immunoassays are run to determine the amount of protein present. Alternatively, cells comprising the ovarian cancer proteins can be used in the assays.

Thus, in a preferred embodiment, the methods comprise combining an ovarian cancer protein and a candidate compound, and determining the binding of the compound to the ovarian cancer protein. Preferred embodiments utilize the human ovarian cancer protein, although other mammalian proteins, e.g., counterparts, may also be used, e.g., for the development of animal models of human disease. In some embodiments, as outlined herein, variant or derivative ovarian cancer proteins may be used.

Generally, in a preferred embodiment of the methods herein, the ovarian cancer protein or the candidate agent is non-diffusably bound to an insoluble support having isolated sample receiving areas (e.g., a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is non-diffusible. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the ovarian cancer protein is bound to the support, and a test compound is added to the assay. Alternatively, the candidate agent is bound to the support and the ovarian cancer protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the test modulating compound to the ovarian cancer protein may be done in a number of ways. In a preferred embodiment, the compound is labeled, and binding determined directly, e.g., by attaching all or a portion of the ovarian cancer protein to a solid support, adding a labeled candidate agent (e.g., a fluorescent label), washing off excess reagent, and determining whether the label is present on the solid support. Various blocking and washing steps may be utilized as appropriate.

In some embodiments, only one of the components is labeled, e.g., the proteins (or proteinaceous candidate compounds) can be labeled. Alternatively, more than one component can be labeled with different labels, e.g., $^{125}$I for the proteins and a fluorophor for the compound. Proximity reagents, e.g., quenching or energy transfer reagents are also useful.

In one embodiment, the binding of the test compound is determined by competitive binding assay. The competitor is a binding moiety known to bind to the target molecule (e.g., an ovarian cancer protein), such as an antibody, peptide, binding partner, ligand, etc. Under certain circumstances, there may be competitive binding between the compound and the binding moiety, with the binding moiety displacing the compound. In one embodiment, the test compound is labeled. Either the compound, or the competitor, or both, is added first to the protein for a time sufficient to allow binding, if present. Incubations may be performed at a temperature which facilitates optimal activity, typically 4-40° C. Incubation periods are typically optimized, e.g., to facilitate rapid high throughput screening. Typically between 0.1 and 1 hr will be sufficient. Excess reagent is generally removed or washed away. The second component is then added, and the presence or absence of the labeled component is followed, to indicate binding.

In a preferred embodiment, the competitor is added first, followed by the test compound. Displacement of the competitor is an indication that the test compound is binding to the ovarian cancer protein and thus is capable of binding to, and potentially modulating, the activity of the ovarian cancer protein. In this embodiment, either component can be labeled. Thus, e.g., if the competitor is labeled, the presence of label in the wash solution indicates displacement by the agent. Alternatively, if the test compound is labeled, the presence of the label on the support indicates displacement.

In an alternative embodiment, the test compound is added first, with incubation and washing, followed by the competitor. The absence of binding by the competitor may indicate that the test compound is bound to the ovarian cancer protein with a higher affinity. Thus, if the test compound is labeled, the presence of the label on the support, coupled with a lack of competitor binding, may indicate that the test compound is capable of binding to the ovarian cancer protein.

In a preferred embodiment, the methods comprise differential screening to identity agents that are capable of modulating the activity of the ovarian cancer proteins. In this embodiment, the methods comprise combining an ovarian cancer protein and a competitor in a first sample. A second sample comprises a test compound, an ovarian cancer protein, and a competitor. The binding of the competitor is determined for both samples, and a change, or difference in binding between the two samples indicates the presence of an agent capable of binding to the ovarian cancer protein and potentially modulating its activity. That is, if the binding of the competitor is different in the second sample relative to the first sample, the agent is capable of binding to the ovarian cancer protein.

Alternatively, differential screening is used to identify drug candidates that bind to the native ovarian cancer protein, but cannot bind to modified ovarian cancer proteins. The structure of the ovarian cancer protein may be modeled, and used in rational drug design to synthesize agents that interact with that site. Drug candidates that affect the activity of an ovarian cancer protein are also identified by screening drugs for the ability to either enhance or reduce the activity of the protein.

Positive controls and negative controls may be used in the assays. Preferably control and test samples are performed in at least triplicate to obtain statistically significant results. Incubation of all samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc. which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in an order that provides for the requisite binding.

In a preferred embodiment, the invention provides methods for screening for a compound capable of modulating the activity of an ovarian cancer protein. The methods comprise adding a test compound, as defined above, to a cell comprising ovarian cancer proteins. Preferred cell types include almost any cell. The cells contain a recombinant nucleic acid that encodes an ovarian cancer protein. In a preferred embodiment, a library of candidate agents are tested on a plurality of cells.

In one aspect, the assays are evaluated in the presence or absence or previous or subsequent exposure of physiological signals, e.g., hormones, antibodies, peptides, antigens, cytokines, growth factors, action potentials, pharmacological agents including chemotherapeutics, radiation, carcinogenics, or other cells (e.g., cell-cell contacts). In another example, the determinations are determined at different stages of the cell cycle process.

In this way, compounds that modulate ovarian cancer agents are identified. Compounds with pharmacological activity are able to enhance or interfere with the activity of the ovarian cancer protein. Once identified, similar structures are evaluated to identify critical structural feature of the compound.

In one embodiment, a method of inhibiting ovarian cancer cell division is provided. The method comprises administration of an ovarian cancer inhibitor. In another embodiment, a method of inhibiting ovarian cancer is provided. The method comprises administration of an ovarian cancer inhibitor. In a further embodiment, methods of treating cells or individuals with ovarian cancer are provided. The method comprises administration of an ovarian cancer inhibitor.

In one embodiment, an ovarian cancer inhibitor is an antibody as discussed above. In another embodiment, the ovarian cancer inhibitor is an antisense or RNAi molecule.

A variety of cell viability, growth, proliferation, and metastasis assays are known to those of skill in the art, as described below.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow. Soft agar growth or colony formation in suspension assays can be used to identify modulators of ovarian cancer sequences, which when expressed in host cells, inhibit abnormal cellular proliferation and transformation. A therapeutic compound would reduce or eliminate the host cells' ability to grow in stirred suspension culture or suspended in semi-solid media, such as semi-solid or soft.

Techniques for soft agar growth or colony formation in suspension assays are described in Freshney (1994) *Culture of Animal Cells: A Manual of Basic Technique* (3d ed.) Wiley- Liss, herein incorporated by reference. See also, the methods section of Garkavtsev, et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with ($^3$H)-thymidine at saturation density can be used to measure density limitation of growth. See, e.g., Freshney (1994), supra. The transformed cells, when transfected with tumor suppressor genes, regenerate a normal phenotype and become contact inhibited and would grow to a lower density.

In this assay, labeling index with ($^3$H)-thymidine at saturation density is a preferred method of measuring density limitation of growth. Transformed host cells are transfected with an ovarian cancer-associated sequence and are grown for 24 hr at saturation density in non-limiting medium conditions. The percentage of cells labeling with ($^3$H)-thymidine is determined autoradiographically. See, e.g., Freshney (1994), supra.

Growth Factor or Serum Dependence

Transformed cells typically have a lower serum dependence than their normal counterparts. See, e.g., Temin (1966) *J. Nat'l Cancer Inst.* 37:167-175; Eagle, et al. (1970) *J. Exp. Med.* 131:836-879; and Freshney, supra. This is in part due to release of various growth factors by the transformed cells. Growth factor or serum dependence of transformed host cells can be compared with that of control.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, pp. 178-184 "Angiogenesis, tumor vascularization, and potential interference with tumor growth" in Mihich (ed. 1985) *Biological Responses in Cancer* Plenum. Similarly, tumor angiogenesis factor (TAF) is released at a higher level in tumor cells than their normal counterparts. See, e.g., Folkman (1992) *Sem Cancer Biol.* 3:89-96.

Various techniques which measure the release of these factors are described in Freshney (1994), supra. Also, see, Unkeless, et al. (1974) *J. Biol. Chem.* 249:4295-4305; Strickland and Beers (1976) *J. Biol. Chem.* 251:5694-5702; Whur, et al. (1980) *Br. J. Cancer* 42:305-312; Gullino, pp. 178-184 "Angiogenesis, tumor vascularization, and potential interference with tumor growth" in Mihich (ed. 1985) *Biological Responses in Cancer* Plenum; and Freshney (1985) *Anticancer Res.* 5:111-130.

Invasiveness into Matrigel

The degree of invasiveness into Matrigel or some other extracellular matrix constituent can be used as an assay to identify compounds that modulate ovarian cancer-associated sequences. Tumor cells exhibit a good correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells.

Alternatively, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by pre-labeling the cells with $^{125}$I and counting the radioactivity on the distal side of the filter or bottom of the dish. See, e.g., Freshney (1984), supra.

Tumor Growth In Vivo

Effects of ovarian cancer-associated sequences on cell growth can be tested in transgenic or immune-suppressed mice. Knock-out transgenic mice can be made, in which the ovarian cancer gene is disrupted or in which an ovarian cancer gene is inserted. Knock-out transgenic mice can be made by insertion of a marker gene or other heterologous gene into the endogenous ovarian cancer gene site in the mouse genome via homologous recombination. Such mice can also be made by substituting the endogenous ovarian cancer gene with a mutated version of the ovarian cancer gene, or by mutating the endogenous ovarian cancer gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. By breeding the chimeric mice it is possible to obtain a new line of mice containing the introduced genetic lesion. See, e.g., Capecchi, et al. (1989) *Science* 244:1288-1292. Chimeric targeted mice can be derived according to Hogan, et al. (1988) *Manipulating the Mouse Embryo: A Laboratory Manual* CSH Press; and Robertson (ed. 1987) *Teratocarcinomas and Embryonic Stem Cells: A Practical Approach* IRL Press, Washington, D.C.

Alternatively, various immune-suppressed or immune-deficient host animals can be used. For example, genetically athymic "nude" mouse (see, e.g., Giovanella, et al. (1974) *J. Nat'l Cancer Inst.* 52:921-930), a SCID mouse, a thymectomized mouse, or an irradiated mouse (see, e.g., Bradley, et al. (1978) *Br. J. Cancer* 38:263-272; Selby, et al. (1980) *Br. J. Cancer* 41:52-61) can be used as a host. Transplantable tumor cells (typically about $10^6$ cells) injected into isogenic hosts will produce invasive tumors in a high proportions of cases, while normal cells of similar origin will not. In hosts which developed invasive tumors, cells expressing an ovarian cancer-associated sequences are injected subcutaneously. After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth.

Polynucleotide Modulators of Ovarian Cancer

Antisense and RNAi Polynucleotides

In certain embodiments, the activity of an ovarian cancer-associated protein is down-regulated, or entirely inhibited, by the use of antisense polynucleotide, e.g., a nucleic acid complementary to, and which can preferably hybridize specifically to, a coding mRNA nucleic acid sequence, e.g., an ovarian cancer protein mRNA, or a subsequence thereof. Binding of the antisense polynucleotide to the mRNA reduces the translation and/or stability of the mRNA.

In the context of this invention, antisense polynucleotides can comprise naturally-occurring nucleotides, or synthetic species formed from naturally-occurring subunits or their close homologs. Antisense polynucleotides may also have altered sugar moieties or inter-sugar linkages. Exemplary among these are the phosphorothioate and other sulfur containing species which are known for use in the art. Analogs are comprehended by this invention so long as they function effectively to hybridize with the ovarian cancer protein mRNA. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single-stranded nucleic acid sequence (either RNA or DNA) capable of binding to target mRNA (sense) or DNA (antisense) sequences for ovarian cancer molecules. A preferred antisense molecule is for an ovarian cancer sequences in Table 19A, or for a ligand or activator thereof. Antisense or sense oligonucleotides, according to the present invention, comprise a fragment generally at least about 14 nucleotides, preferably from about 14 to 30 nucleotides. An antisense or a sense oligonucleotide can be developed based upon a cDNA sequence encoding a given protein. See, e.g., Stein and Cohen (1988) *Cancer Res.* 48:2659-2668; and van der Krol, et al. (1988) *BioTechniques* 6:958-976.

RNA interference is a mechanism to suppress gene expression in a sequence specific manner. See, e.g., Brumelkamp, et al. (2002) *Sciencexpress* (21 Mar. 2002); Sharp (1999) *Genes Dev.* 13:139-141; and Cathew (2001) *Curr. Op. Cell Biol.* 13:244-248. In mammalian cells, short, e.g., 21 nt, double stranded small interfering RNAs (siRNA) have been shown to be effective at inducing an RNAi response. See, e.g., Elbashir, et al. (2001) *Nature* 411:494-498. The mechanism may be used to down-regulate expression levels of identified genes, e.g., treatment of or validation of relevance to disease.

Ribozymes

In addition to antisense polynucleotides, ribozymes can be used to target and inhibit transcription of ovarian cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g., Castanotto, et al. (1994) *Adv. Pharmacol.* 25: 289-317 for a general review of the properties of different ribozymes).

The general features of hairpin ribozymes are described, e.g., in Hampel, et al. (1990) *Nucl. Acids Res.* 18:299-304; European Patent Publication No. 0 360 257; U.S. Pat. No. 5,254,678. Methods of preparing them are well known to those of skill in the art. See, e.g., WO 94/26877; Ojwang, et al. (1993) *Proc. Nat'l Acad. Sci. USA* 90:6340-6344; Yamada, et al. (1994) *Hum. Gene Ther.* 1:39-45; Leavitt, et al. (1995) *Proc. Nat'l Acad. Sci. USA* 92:699-703; Leavitt, et al. (1994) *Hum. Gene Ther.* 5:1151-120; and Yamada, et al. (1994) *Virology* 205:121-126.

Polynucleotide modulators of ovarian cancer may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of ovarian cancer may be introduced into a cell containing the target nucleic acid sequence, e.g., by formation of an polynucleotide-lipid complex, as described in WO 90/10448. It is understood that the use of antisense molecules or knock out and knock in models may also be used in screening assays as discussed above, in addition to methods of treatment.

Thus, in one embodiment, methods of modulating ovarian cancer in cells or organisms are provided. In one embodiment, the methods comprise administering to a cell an anti-ovarian cancer antibody that reduces or eliminates the biological activity of an endogenous ovarian cancer protein. Alternatively, the methods comprise administering to a cell or organism a recombinant nucleic acid encoding an ovarian cancer protein. This may be accomplished in any number of ways. In a preferred embodiment, e.g., when the ovarian cancer sequence is down-regulated in ovarian cancer, such state may be reversed by increasing the amount of ovarian cancer gene product in the cell. This can be accomplished, e.g., by over-expressing the endogenous ovarian cancer gene or administering a gene encoding the ovarian cancer sequence, using known gene-therapy techniques, e.g. In a preferred embodiment, the gene therapy techniques include the incorporation of the exogenous gene using enhanced homologous recombination (EHR), e.g., as described in PCT/US93/03868, hereby incorporated by reference in its entirety. Alternatively, e.g., when the ovarian cancer sequence is up-regulated in ovarian cancer, the activity of the endogenous ovarian cancer gene is decreased, e.g., by the administration of an ovarian cancer antisense or RNAi nucleic acid.

In one embodiment, the ovarian cancer proteins of the present invention may be used to generate polyclonal and monoclonal antibodies to ovarian cancer proteins. Similarly, the ovarian cancer proteins can be coupled, using standard technology, to affinity chromatography columns. These columns may then be used to purify ovarian cancer antibodies useful for production, diagnostic, or therapeutic purposes. In a preferred embodiment, the antibodies are generated to epitopes unique to an ovarian cancer protein; that is, the antibodies show little or no cross-reactivity to other proteins. The ovarian cancer antibodies may be coupled to standard affinity chromatography columns and used to purify ovarian cancer proteins. The antibodies may also be used as blocking polypeptides, as outlined above, since they will specifically bind to the ovarian cancer protein.

Methods of Identifying Variant Ovarian Cancer-associated Sequences

Without being bound by theory, expression of various ovarian cancer sequences is correlated with ovarian cancer. Accordingly, disorders based on mutant or variant ovarian cancer genes may be determined. In one embodiment, the invention provides methods for identifying cells containing variant ovarian cancer genes, e.g., determining all or part of the sequence of at least one endogenous ovarian cancer genes in a cell. This may be accomplished using any number of sequencing techniques. In a preferred embodiment, the invention provides methods of identifying the ovarian cancer genotype of an individual, e.g., determining all or part of the sequence of at least one ovarian cancer gene of the individual. This is generally done in at least one tissue of the individual, and may include the evaluation of a number of tissues or different samples of the same tissue. The method may include comparing the sequence of the sequenced ovarian cancer gene to a known ovarian cancer gene, e.g., a wild-type gene.

The sequence of all or part of the ovarian cancer gene can then be compared to the sequence of a known ovarian cancer gene to determine if any differences exist. This can be done using any number of known homology programs, such as Bestfit, etc. In a preferred embodiment, the presence of a difference in the sequence between the ovarian cancer gene of the patient and the known ovarian cancer gene correlates with a disease state or a propensity for a disease state, as outlined herein.

In a preferred embodiment, the ovarian cancer genes are used as probes to determine the number of copies of the ovarian cancer gene in the genome.

In another preferred embodiment, the ovarian cancer genes are used as probes to determine the chromosomal localization of the ovarian cancer genes. Information such as chromosomal localization finds use in providing a diagnosis or prognosis in particular when chromosomal abnormalities such as translocations, and the like are identified in the ovarian cancer gene locus.

Administration of Pharmaceutical and Vaccine Compositions

In one embodiment, a therapeutically effective dose of an ovarian cancer protein or modulator thereof, is administered to a patient. By "therapeutically effective dose" herein is meant a dose that produces effects for which it is administered. The exact dose will depend on the purpose of the treatment, and will be ascertainable by one skilled in the art using known techniques. See, e.g., Ansel, et al. (1999) *Pharmaceutical Dosage Forms and Drug Delivery Systems* Lippincott; Lieberman. (1992) *Pharmaceutical Dosage Forms* (vols. 1-3) Dekker, ISBN 0824770846, 082476918X, 0824712692, 0824716981; Lloyd (1999) *The Art, Science and Technology of Pharmaceutical Compounding* Amer. Pharmaceutical Assn.; and Pickar (1999) *Dosage Calculations* Thomson. Adjustments for ovarian cancer degradation, systemic versus localized delivery, and rate of new protease synthesis, as well as the age, body weight, general health, sex, diet, time of administration, drug interaction, and the severity of the condition may be necessary, and will be ascertainable with routine experimentation by those skilled in the art. U.S. patent application Ser. No. 09/687,576, further discloses the use of compositions and methods of diagnosis and treatment in ovarian cancer is hereby expressly incorporated by reference.

A "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

The administration of the ovarian cancer proteins and modulators thereof of the present invention can be done in a variety of ways as discussed above, including, but not limited to, orally, subcutaneously, intravenously, intra-nasally, transdermally, intraperitoneally, intramuscularly, intrapulmonary, vaginally, rectally, or intraocularly. In some instances, e.g., in the treatment of wounds and inflammation, the ovarian cancer proteins and modulators may be directly applied as a solution or spray.

The pharmaceutical compositions of the present invention comprise an ovarian cancer protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol.

The pharmaceutical compositions can be administered in a variety of unit dosage forms depending upon the method of administration. For example, unit dosage forms suitable for oral administration include, but are not limited to, powder, tablets, pills, capsules, and lozenges. It is recognized that ovarian cancer protein modulators (e.g., antibodies, antisense constructs, ribozymes, small organic molecules, etc.) when administered orally, should be protected from digestion. This is typically accomplished either by complexing the molecule(s) with a composition to render it resistant to acidic and enzymatic hydrolysis, or by packaging the molecule(s) in an appropriately resistant carrier, such as a liposome or a protection barrier. Means of protecting agents from digestion are well known in the art.

The compositions for administration will commonly comprise an ovarian cancer protein modulator dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like in accordance with the particular mode of administration selected and the patient's needs. See, e.g., *Remington's Pharmaceutical Science* (15th ed., 1980) and Hardman and Limbird (eds. 2001) *Goodman and Gillman: The Pharmacological Basis of Therapeutics* (10th ed.) McGraw-Hill. Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions are readily available.

The compositions containing modulators of ovarian cancer proteins can be administered for therapeutic or prophylactic treatments. In therapeutic applications, compositions are administered to a patient suffering from a disease (e.g., a cancer) in an amount sufficient to cure or at least partially arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the agents of this invention to effectively treat the patient. An amount of modulator that is capable of preventing or slowing the development of cancer in a mammal is referred to as a "prophylactically effective dose." The particular dose required for a prophylactic treatment will depend upon the medical condition and history of the mammal, the particular cancer being prevented, as well as other factors such as age, weight, gender, administration route, efficiency, etc. Such prophylactic treatments may be used, e.g., in a mammal who has previously had cancer to prevent a recurrence of the cancer, or in a mammal who is suspected of having a significant likelihood of developing cancer based, e.g., in part, upon gene expression profiles. Vaccine strategies may be used, in either a DNA vaccine form, or protein vaccine.

It will be appreciated that the present ovarian cancer protein-modulating compounds can be administered alone or in combination with additional ovarian cancer modulating compounds or with other therapeutic agent, e.g., other anti-cancer agents or treatments.

In numerous embodiments, one or more nucleic acids, e.g., polynucleotides comprising nucleic acid sequences set forth in Table 19A, such as RNAi, antisense polynucleotides or ribozymes, will be introduced into cells, in vitro or in vivo. The present invention provides methods, reagents, vectors, and cells useful for expression of ovarian cancer-associated polypeptides and nucleic acids using in vitro (cell-free), ex vivo or in vivo (cell or organism-based) recombinant expression systems.

The particular procedure used to introduce the nucleic acids into a host cell for expression of a protein or nucleic acid is application specific. Many procedures for introducing foreign nucleotide sequences into host cells may be used. These include the use of calcium phosphate transfection, spheroplasts, electroporation, liposomes, microinjection, plasma vectors, viral vectors and any of the other well known methods for introducing cloned genomic DNA, cDNA, synthetic DNA or other foreign genetic material into a host cell. See, e.g., Berger and Kimmel (1987) *Guide to Molecular Cloning Techniques* from Methods in Enzymology (vol. 152) Academic Press; Ausubel, et al. (eds. 1999 and supplements) *Current Protocols* Lippincott; and Sambrook, et al. (2001) *Molecular Cloning: A Laboratory Manual* (3d ed., Vol. 1-3) CSH Press.

In a preferred embodiment, ovarian cancer proteins and modulators are administered as therapeutic agents, and can be formulated as outlined above. Similarly, ovarian cancer genes (including both the full-length sequence, partial sequences, or regulatory sequences of the ovarian cancer coding regions) can be administered in a gene therapy application. These ovarian cancer genes can include antisense applications, either as gene therapy (e.g., for incorporation into the genome) or as antisense compositions, as will be appreciated by those in the art.

Ovarian cancer polypeptides and polynucleotides can also be administered as vaccine compositions to stimulate HTL, CTL, and antibody responses. Such vaccine compositions can include, e.g., lipidated peptides (see, e.g., Vitiello, et al. (1995) *J. Clin. Invest.* 95:341-349), peptide compositions encapsulated in poly(D,L-lactide-co-glycolide, "PLG") microspheres (see, e.g., Eldridge, et al. (1991) *Molec. Immunol.* 28:287-294; Alonso, et al. (1994) *Vaccine* 12:299-306; Jones, et al. (1995) *Vaccine* 13:675-681), peptide compositions contained in immune stimulating complexes (ISCOMS; see, e.g., Takahashi, et al. (1990) *Nature* 344:873-875; Hu, et al. (1998) *Clin. Exp. Immunol.* 113:235-243), multiple antigen peptide systems (MAPs; see, e.g., Tam (1988) *Proc. Nat'l Acad. Sci. USA* 85:5409-5413; Tam (1996) *J. Immunol. Methods* 196:17-32), peptides formulated as multivalent peptides; peptides for use in ballistic delivery systems, typically crystallized peptides, viral delivery vectors (Perkus, et al., p. 379, in Kaufmann (ed. 1996) *Concepts in Vaccine Development* de Gruyter; Chakrabarti, et al. (1986) *Nature* 320:535-537; Hu, et al. (1986) *Nature* 320:537-540; Kieny, et al. (1986) *AIDS Bio/Technology* 4:790-795; Top, et al. (1971) *J. Infect. Dis.* 124:148-154; Chanda, et al. (1990) *Virology* 175:535-547), particles of viral or synthetic origin (see, e.g., Kofler, et al. (1996) *J. Immunol. Methods* 192:25-35; Eldridge, et al. (1993) *Sem. Hematol.* 30:16-24; Falo, et al. (1995) *Nature Med.* 7:649-653), adjuvants (Warren, et al. (1986) *Ann. Rev. Immunol.* 4:369-388; Gupta, et al. (1993) *Vaccine* 11:293-306), liposomes (Reddy, et al. (1992) *J. Immunol.* 148:1585-1589; Rock (1996) *Immunol. Today* 17:131-137), or, naked or particle absorbed cDNA (Ulmer, et al. (1993) *Science* 259: 1745-1749; Robinson, et al. (1993) *Vaccine* 11:957-960; Shiver, et al., p. 423, in Kaufmann (ed. 1996) *Concepts in Vaccine Development* de Gruyter; Cease and Berzofsky (1994) *Ann. Rev. Immunol.* 12:923-989; and Eldridge, et al. (1993) *Sem. Hematol.* 30:16-24). Toxin-targeted delivery technologies, also known as receptor mediated targeting, such as those of Avant Immunotherapeutics, Inc. (Needham, Mass.) may also be used.

Vaccine compositions often include adjuvants. Many adjuvants contain a substance designed to protect the antigen from rapid catabolism, such as aluminum hydroxide or mineral oil, and a stimulator of immune responses, such as lipid A, Bortadella pertussis, or *Mycobacterium tuberculosis* derived proteins. Certain adjuvants are commercially available as, e.g., Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Vaccines can be administered as nucleic acid compositions wherein DNA or RNA encoding one or more of the polypeptides, or a fragment thereof, is administered to a patient. See, e.g., Wolff et. al. (1990) *Science* 247:1465-1468; U.S. Pat.

Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, e.g., as a vector to express nucleotide sequences that encode ovarian cancer polypeptides or polypeptide fragments. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover, et al. (1991) *Nature* 351:456-460. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata, et al. (2000) *Mol. Med. Today* 6:66-71; Shedlock, et al. (2000) *J. Leukoc. Biol.* 68:793-806; and Hipp, et al. (2000) In Vivo 14:571-85.

Methods for the use of genes as DNA vaccines are well known, and include placing an ovarian cancer gene or portion of an ovarian cancer gene under the control of a regulatable promoter or a tissue-specific promoter for expression in an ovarian cancer patient. The ovarian cancer gene used for DNA vaccines can encode full-length ovarian cancer proteins, but more preferably encodes portions of the ovarian cancer proteins including peptides derived from the ovarian cancer protein. In one embodiment, a patient is immunized with a DNA vaccine comprising a plurality of nucleotide sequences derived from an ovarian cancer gene. For example, ovarian cancer-associated genes or sequence encoding sub-fragments of an ovarian cancer protein are introduced into expression vectors and tested for their immunogenicity in the context of Class I MHC and an ability to generate cytotoxic T cell responses. This procedure provides for production of cytotoxic T cell responses against cells which present antigen, including intracellular epitopes.

In a preferred embodiment, the DNA vaccines include a gene encoding an adjuvant molecule with the DNA vaccine. Such adjuvant molecules include cytokines that increase the immunogenic response to the ovarian cancer polypeptide encoded by the DNA vaccine. Additional or alternative adjuvants are available.

In another preferred embodiment ovarian cancer genes find use in generating animal models of ovarian cancer. When the ovarian cancer gene identified is repressed or diminished in cancer tissue, gene therapy technology, e.g., wherein antisense RNA directed to the ovarian cancer gene will also diminish or repress expression of the gene. Animal models of ovarian cancer find use in screening for modulators of an ovarian cancer-associated sequence or modulators of ovarian cancer. Similarly, transgenic animal technology including gene knockout technology, e.g., as a result of homologous recombination with an appropriate gene targeting vector, will result in the absence or increased expression of the ovarian cancer protein. When desired, tissue-specific expression or knockout of the ovarian cancer protein may be necessary.

It is also possible that the ovarian cancer protein is overexpressed in ovarian cancer. As such, transgenic animals can be generated that overexpress the ovarian cancer protein. Depending on the desired expression level, promoters of various strengths can be employed to express the transgene. Also, the number of copies of the integrated transgene can be determined and compared for a determination of the expression level of the transgene. Animals generated by such methods find use as animal models of ovarian cancer and are additionally useful in screening for modulators to treat ovarian cancer.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, ovarian cancer-specific nucleic acids or antibodies, hybridization probes and/or primers, siRNA or antisense polynucleotides, ribozymes, dominant negative ovarian cancer polypeptides or polynucleotides, small molecules inhibitors of ovarian cancer-associated sequences etc. A therapeutic product may include sterile saline or another pharmaceutically acceptable emulsion and suspension base.

In addition, the kits may include instructional materials containing directions (e.g., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of ovarian cancer-associated sequences. Such kits can be prepared from readily available materials and reagents. For example, such kits can comprise one or more of the following materials: an ovarian cancer-associated polypeptide or polynucleotide, reaction tubes, and instructions for testing ovarian cancer-associated activity. Optionally, the kit contains biologically active ovarian cancer protein. A wide variety of kits and components can be prepared according to the present invention, depending upon the intended user of the kit and the particular needs of the user. Diagnosis would typically involve evaluation of a plurality of genes or products. The genes will be selected based on correlations with important parameters in disease which may be identified in historical or outcome data.

EXAMPLES

Example 1

Gene Chip Analysis

Molecular profiles of various normal and cancerous tissues were determined and analyzed using gene chips. RNA was isolated and gene chip analysis was performed as described (Glynne, et al. (2000) *Nature* 403:672-676; Zhao, et al. (2000) *Genes Dev.* 14:981-993).

TABLE 8B

| Pkey | CAT Number | Accession |
|---|---|---|
| 101249 | 2520_1 | L18964 NM_002740 L33881 AA095249 BE080871 AW605320 M85571 AA179776 AA160650 AW117327 BE467131 AW088338 AW937631 AW087514 AI480090 AI873147 T57875 AI217404 AA827196 AI279471 AA969093 AA815168 AA988896 AI754623 T28044 AW950302 AW950294 AI032193 AI953696 AI630583 AA062633 BE541355 AA180493 AW015748 AA253651 |
| 100661 | 23182_1 | BE623001 U05096 AA383604 AW966416 N53295 AA460213 AW571519 AA603655 |
| 116401 | 95855_1 | AW893940 AW978851 AA034240 AI686323 AI767653 AA829515 AA053933 AA737691 W92607 AW261869 AA835698 AA447216 AI623248 Z21891 AA835700 AA599963 T20152 AA533167 |
| 116416 | 373989_1 | AW753676 R11789 AW001886 AA609219 AW780420 AI860557 AI280331 AI334300 AI288870 AA669343 N29918 BE537790 AA934687 H79075 N42970 R63752 |
| 132191 | 54683_4 | AA507576 AI610269 AI380079 R40309 AI203932 AI342128 AI342578 R43110 AW583269 AI375234 AI092708 R52802 AI028462 AI016062 AI189144 AI016691 W45515 AA551452 AA449431 T10046 AA424059 N62822 AW197701 AA465242 AI418989 AI942433 AI891115 BE302316 AI743979 AI283341 AW340338 AA774643 AW104778 AI078020 N21487 H97562 AA970063 BE327945 F03880 F03885 AA970699 AI298468 AI380330 AI247787 AA778907 AI200154 AI089890 AI695738 W88524 AI471010 AA700191 AA778937 BE440182 R79225 AA338236 AA548984 AA907692 N21250 AW904736 AI909337 AA987772 AW959228 AI149372 N29644 AI039967 AA677529 AI694291 R85811 N28672 AA465598 AA321185 AW130492 AI824479 AI682992 |
| 130941 | 2774_1 | NM_000869 D49394 BE252349 AW249320 AW249140 AW250535 S82612 AJ003079 AJ005205 AW178407 AA811360 AW976407 AW976408 AW248903 AA731733 AA804189 AA703169 AI435492 AI076288 AA912176 AA743457 R08170 C06167 R02351 |
| 115909 | 47548_1 | AW872527 AA453863 AA442475 AF086541 AI692575 AW131631 AA732993 W96131 AA436666 AA453779 AA365504 AW959717 AA975337 AA365503 AI632902 AA659686 AA665087 C00396 AA988869 |
| 108778 | 18565_1 | AF133123 NM_012086 AA128292 S81493 AL137453 BE614053 AA307628 BE009521 BE085659 BE085542 BE085598 AL120264 R13165 AA429306 R13465 R55236 AW994182 W00838 AW994404 AW994321 AA516147 AA345603 AW953009 BE315104 AI126654 AA626457 AA291327 H67983 H66271 H67976 AW270955 AA758221 AI023487 AI921811 AI953370 AF085850 R70992 N25129 AW295143 AI433661 AW608361 AA873402 AI217453 AI953358 AA262143 AA928495 AI475268 AI167211 AW385961 AA259045 AI762630 AA428238 AI001932 AI735550 AI951370 AA766807 S81492 AA918976 AI040967 R70939 AA469065 T70340 AA477615 AA478070 AI017743 AI608833 AI635824 AI186039 AA741312 AI040184 H67656 AA258221 AA731316 AI381293 AW298473 R55237 R37375 AI768014 AA128548 AI206773 AI879827 R64193 AA300576 NM_014597 AA223318 AA171806 BE269461 AW578439 AW368395 AW604388 AW953513 AA772816 AW604383 AW577851 BE169672 AW117711 AW366303 AW366302 AW366308 AW366304 AW366300 AI908432 AW591937 AI358420 AW272622 C75067 AI926471 AW002266 |
| 102136 | 17647_1 | BE064947 BE064722 T10372 AW838681 AI811119 AW262098 AA588547 AI916666 AI440083 AI078150 F24260 AA512919 AI953413 AI064798 AI420425 AA191324 BE503222 AI632721 AA180035 AA558329 W44843 T10610 W38442 BE542869 AI125024 BE279566 AW747936 AI589491 AA559096 AI090265 AA548959 AA223220 AW515936 AW368395 AW368407 BE540776 AI039762 AI584020 AA171691 |
| 108857 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87768 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 102305 | 18424_1 | AL043202 U33286 NM_001316 AF053641 AL048759 N99830 AA263091 AW408174 N90467 R84306 AA317882 BE613644 AA307378 T10722 AA207207 AA315560 AA113938 AW386317 AW386316 L44546 AW386335 AA243317 AA713588 AA243317 AA649035 BE300737 AW752491 AW902334 AW993922 BE003403 AA251521 AA382754 AA339152 AA382619 H58600 H67810 T70379 T82109 D81644 D60375 H59003 BE075732 AA471242 H17790 F11801 T84903 R78076 BE614356 R16380 RL6395 AA876127 W95535 AA164768 AI279876 H02142 C18698 AA635866 AW544410 AI539769 T39128 AL121103 AA192466 AA213367 AI963800 BE090601 Z20096 BE566508 AI969470 BE044090 T65536 AA837311 AA075484 AA075621 AA778294 AA587266 T69722 AA446118 X85624 AI334209 AI587101 AI281280 AA568602 AA946837 C75603 AA236997 AA459274 AI150191 AA165156 AI198839 AA789258 AI139373 AA236574 AI127770 AA678954 AI140786 AA113939 AI187231 AI754062 AI753243 AW439719 AW439362 H02038 C17463 AI400951 AA227539 N66040 R89384 AA872668 AI344110 W95420 AA164700 C05669 BE094097 AI826398 H58956 T17222 AW139044 AI271344 T16445 R42323 C75565 AA165228 AI025443 AA165229 C21496 AI826239 AI68711 AA582354 AA524392 R01549 R01641 Z21083 AA528463 T39127 AA989472 F09450 AA084485 BE004378 AW974353 AA137250 AI278406 AW609291 AI137249 AA142866 AA639198 AW609271 AW149760 AI025112 AA236620 AA937248 U90736 AW005487 AW674427 BE397971 AW609285 T65640 T99684 T97378 AW609366 T85647 AI572235 T99083 AA199583 AW303874 T35523 AA586445 Z39669 AA459503 N95643 AW821210 AW813461 AW582064 AW609293 AW609320 AW609270 AW582085 AW582071 AW609318 AW609270 AW813451 AW813456 AW582079 AW609276 AW609280 AW609290 AW582101 AW582102 AW609263 AW609317 AW609256 AW609305 AW582063 F06655 AW605343 AA446426 BE090595 AW969578 T79852 AI082505 N63239 AI973168 AI086182 AA846711 AI874213 AA730605 AI927257 AA912624 D60376 T10180 AA705847 AI018123 AA493197 T67083 R77739 AA953087 R00885 AI370606 R01642 AA862914 N57843 AW023353 H77483 H68082 R42337 H58601 T97267 |

TABLE 8B-continued

| Pkey | CAT Number | Accession |
|---|---|---|
| 109648 | 708849_1 | H17800 AI362549 AI671064 T23526 F03426 F04694 F04600 AI635856 Z38715 F02039 AW022635 |
| 132528 | 11027_8 | T78736 AA284422 AA283006 |
| 101804 | 26687_1 | M86699 NM_003318 AL133475 AA122377 Z21415 R57092 AA806569 AA811904 BE538323 R41558 AA421620 AI337292 AA470077 AW795371 AA543024 AI677941 AI472200 AI215042 AA732384 AA837143 AA804229 AI907533 AI742701 AA121159 AI973225 AI620839 |
| 132572 | 31281_1 | AI929659 AA227827 AF069765 AW408768 NM_006947 AF077019 AA220974 H07969 C14621 D52294 BE512960 BE614138 BE258539 BE251981 AA355433 AA481126 AW403053 BE542282 AI929818 AL120605 AW753079 AW391834 BE018603 BE395262 W21406 AW663259 AW975690 W93905 W96519 AI863832 AA443177 AA730942 T99558 T86581 W19444 N55583 AI701020 AI928986 AI857864 AI590849 AW081819 AA714970 AI122630 W04887 AA66427 AA602680 W93645 AA582946 AW008812 AA311187 AA463631 AI421918 AA40518 AI921404 AA143770 AA587675 BE302192 AA813080 AI493386 AW327435 AW340871 AI143616 AA687231 AA218961 AI362249 AI378345 N74716 AW969249 AA468581 AA516399 AI274726 AI131244 AI572604 AI929236 AW327971 R65637 N90309 H07877 W96486 AI358806 T90801 AI383246 AI740957 T86758 AI471248 AI864233 AA910590 AI079094 AW805781 AA709025 AW196707 AW327436 AI903790 AI873956 T99348 AI924643 AW103910 AI802993 AI080390 T99098 D19794 AW327972 AI935904 AI288575 AW36875 AA779784 N93574 AW769295 W32639 AA363094 N89012 W39751 AI291329 AI291371 AA829411 AI985219 AI422775 AA918940 AA363108 AA192633 AF086131 AA373679 AA165043 AA355705 AI243507 AI027796 AA573461 AA757260 AI370979 AA574149 AA558276 N70650 AI478948 R35393 AA448435 AA334659 AW879356 AA436527 AW972044 W25165 AA521219 AI094141 AI302096 AW578551 AW578534 AW390535 AI131472 N50381 AA736938 AI089112 AA863053 AI359793 AA962268 T27353 D82590 AA448297 AI277168 AI368457 AI273174 AA330346 AA342341 AA355159 T85701 BE162893 T99703 |
| 131985 | 113870_1 | AA503020 AI858190 AI686571 AW615203 AW073686 AW172459 AI828762 AW150534 AI859795 AA411046 AI539195 AA404609 AI638559 AA434329 AA171844 AI684143 AA953518 AW470108 AI870700 AA706376 AI539668 AI683712 AA075579 AI682137 AA291512 AA554431 H51315 AA404225 AA075632 AA172293 H51911 |
| 132624 | 42095_1 | AA326108 W74020 AW612698 AI750909 AA487800 AA270695 AA044941 H20708 AA296750 AA018401 AA378581 AW964159 AA018887 R68533 AA525338 AA526640 H84308 AA278942 AA164818 AA847110 T82335 N25519 AA021474 N31381 N36297 AA838191 AA318932 AA961206 N41430 N41439 AW630477 W37595 BE394538 AA365256 N47771 N34873 AA988105 AI242138 AW148523 AI978761 N50882 AA527448 AW086200 AI750910 N50868 AA709437 N51946 AI222179 AA732883 H96742 AW615360 N53720 W37490 R87362 AA613273 H98999 AI469022 AI368442 AI460122 N20486 N24087 AA164819 N24878 AW471270 AW590458 R68240 AA594434 N20400 AI419626 AW500664 AI033658 AA593215 AA907408 AI422627 H85551 AA923571 D62680 AW627456 H96206 AA016289 AA485896 N25691 |
| 132632 | 4312_1 | AU076916 BE298110 AW239395 AW672700 NM_003875 U10860 AW651755 BE297958 C03806 AI795876 AA644165 T36030 AW392852 AA446421 AW881866 AI469428 BE548103 T96204 R94457 N78225 AI564549 AW004984 AW780423 AW675448 AW087890 AA971454 AA305698 AA879433 AA535069 AI394371 AA928053 AI378367 N59764 AI364000 AI431285 T81090 AW674657 AW674987 AA897396 AW673412 BE063175 AW674408 AI020011 R00723 AI753769 AI460161 AW079585 AW275744 AI873729 D25791 BE537646 T81139 R00722 |
| 102610 | 9336_1 | U65011 NM_006115 AW182053 BE383930 BE407839 BE409930 BE408826 AW370292 AA312859 AA136204 AW365852 AW365735 BE622732 AW939295 AA781195 AI017284 AW375329 AW375366 AW513316 AW770892 BE207426 AW173563 AW178424 AW365726 AF025440 AW172852 AI570998 AW117792 AI885499 BE465516 AI017427 AW130942 AI613210 AW591505 AW169285 AI521444 AI745044 AI627904 AI690634 AI289305 AA861253 AI612799 BE207425 AI149694 BE207404 AI744982 AI613210 AW375467 AI014752 AA613844 AI725693 AA136089 AI290092 AA565489 AI689083 AI859014 AW051225 AA665758 AA496991 AA902662 AI082468 AI014752 AW167626 AW084200 AW188723 AA617626 AI918664 AW381473 AW381543 AA598817 AW088942 AW050423 AA564738 T19428 AI567170 AW166726 AW084200 AW188723 AA617626 AI918664 AW381473 AW381543 AA598817 AW088942 AW050423 AI021918 AA160639 U66560 AA321623 U52098 AL119453 AA455712 N80080 N46550 W07223 N75923 W05057 AI811577 AA455657 AI275409 AI139121 AI927568 AI927562 AI139471 AA160473 N78795 AI719983 AI718928 AA723097 AI335776 N39140 N59184 AI587600 AI864812 AA732097 N74667 AA832398 H89600 D19825 AI554833 |
| 102627 | 25245_1 | NM_006276 NM_006276 L41887 L22253 BE379909 BE543960 D55986 AA852399 AI630020 W77996 AA278193 R10505 AI963201 AI739336 BE174301 AA662222 AA494481 BE440161 AW780428 BE504485 BE504485 BE504485 BE504485 AI093618 BE504485 AA580279 AA664912 AA244152 AW611553 BE503285 AA211023 AA383016 AI698174 AW195381 AA948229 AI768495 AI690437 N30025 AI718952 AI953572 BE464509 AA777315 AI337221 AW070910 AI953848 AW674561 H54177 AW510890 AW078699 AI436178 AA630759 BE502074 AA278769 AI499038 AW469072 AA778071 AW236753 AI933033 AI690458 AI276691 AW768235 AI952118 AA425156 AA610579 W73953 AA244153 W86034 AI948872 AI952678 AW087811 AI335591 AI869883 AI926911 W48865 AI048024 AA214485 AI972522 AI151368 W48738 AA214467 AA334640 AI678170 AA927525 AA581588 W96283 AA365470 AI471919 AW611488 AA211834 AI365198 AI698365 AW002238 AA507624 W96150 AA446490 AL048025 AA852400 AA362221 AI338376 R35083 AA290812 R10397 AA975988 AW236462 Z43032 H16969 F13487 D19858 AA452207 BE085942 AA344396 AW949533 AA279472 AW902406 AW070440 BE395195 H00835 AA300750 AA729303 AA420591 AA385025 AA420542 R69155 AA420592 AA281747 N88502 AI458206 AI700996 AW418607 AW341202 AI825692 W00640 AA214405 AA044744 AI950617 AI950617 BE467493 AA474113 AA446310 AI337715 AA581588 AI911573 AW243968 AI628622 AW173020 AW079958 AI140387 AW051969 |
| 132725 | 29101_1 | |

TABLE 8B-continued

| Pkey | CAT Number | Accession |
|---|---|---|
| 111234 | 83711_2 | AW299438 AI127170 AW769164 AI422435 AI307116 BE549519 AI371116 AA281748 AA701073 AA679948 BE551197 N50345 AW338776 BE326601 AI142892 AW470687 AI989568 AA911241 AW294822 AI174414 AA804366 AI004725 AW271994 AI559313 AI270102 AI351542 AW768904 AA765964 AI961708 AI149231 AA995907 AI094280 AI185753 H01219 AW768846 AA747500 AA970106 AI601238 AA513452 AW612802 BE075163 R39171 AI565328 AI375559 F10356 AA284625 BE241509 AI702889 AW193010 AA649847 AW439150 AA721407 AA810333 AA706384 AI049887 BE569015 BE622280 BE566618 AW967342 R69269 |
| 134161 | 16074_1 | AA902656 AI185915 R43705 H15150 H09794 AA832464 AI697438 AI354538 AI436354 AA948272 AA928143 AI091263 R41658 AI352580 AI122948 AA946670 AI340088 AI275007 N70255 AA721176 AI934162 AA827098 AA935934 AA827088 AI081207 AA992399 AW130757 AI805667 AA035556 AI379266 AI093901 AI095234 AA909079 AA516079 AI572357 AA205969 AI432383 AA905290 AW628920 AW182996 AI266084 N49879 AW024457 AI246246 AI934031 AI369270 AI003836 AA010063 AA494361 AI284151 AI919536 N34884 N69287 AW510465 AI358609 AW081421 AA706205 AI085317 AI140633 AI347104 AA602547 AI686707 AA872686 AA694028 AI094546 Z40832 AI382838 AA610132 AA501433 H84120 AI140722 AW674839 BE503822 AW663895 BE327472 AW393494 AI340087 W04189 AW393499 H56506 BE089878 BE301950 AI025475 AA724446 BE275324 H15210 AW957667 |
| 132939 | 11857_1 | AA634543 AI682259 AF117108 BE396917 NM_006547 U97188 U76705 BE560799 BE396918 BE269531 BE560268 BE560346 AA836048 AL023775 BE545535 AA427803 C18804 D58801 AA303353 U46218 BE539704 AA187966 AA252545 AA261821 D63197 AI824109 AI088047 AI424833 AI807368 AI250857 AA741476 AI146832 AA169615 AI808821 AI274288 AW136704 AI206172 AA917039 AA243584 AI808611 AW674709 AA935733 AW450092 AA905172 AA471196 AA302256 AW673448 AI265047 AW511295 AA247134 W81035 AA722962 AW662471 R64432 AW044616 AI086619 AW628346 AW043682 AA425750 AI743038 AI68723 AA187143 AI376987 AI803976 AI275537 AW471358 AW104877 AA195464 W81072 AW197351 AA932674 AI393420 AI43498 R63822 AW085083 AI240272 W87006 AA011347 H58428 AI497895 R23223 |
| 111345 | 6692_1 | AB009284 AF000416 AA022636 BE082610 AW367997 AA491410 AA337477 AA336421 W38526 AA625283 AA773685 AA490078 T66134 AA847838 AA022647 AW054726 AI918001 AA431966 AI263596 AI804298 AW469314 U76189 AA779001 AA625945 AI042357 AI674730 AA410350 AK001450 AV654353 AA058443 D81618 AA853665 W31930 AA334445 AW955767 N47777 AA883784 AA428916 AI652062 AA329703 AI417923 AI435031 AA708791 AI989636 AI220345 AI239913 AI220102 AI435875 AI076731 AI377049 AI039173 AW972638 N90076 AW263652 BE440048 BE440013 AA577463 AI038774 AW204992 AA846580 AA501952 AA342058 AA508525 D61670 W31725 AI689499 AI955969 AA526628 AI282717 T66198 AW263155 AA314512 AW408152 AA360413 BE206274 AK001402 AA307665 AW954678 W39078 AW369236 AW801517 AW368503 AW801322 AI674163 AA861077 AW369072 AW361194 AW369125 AW364187 H94225 T79502 AA131908 BE071359 AW368489 AW083479 AW970625 AW613124 AW960972 AA994566 AI280346 AA884588 AA653563 AI200023 N89820 AW768792 C000145 R96554 AI738568 AI830199 AW118577 AI478895 AI688497 H92996 AW083479 AW970625 AW613124 AW960972 AA994566 AI280346 AA884588 AA653563 AI200023 N89820 AW768792 C000145 R96554 AA806630 AA806158 AW592520 R96509 AA813923 AA502823 AW467889 AA960972 T79416 |
| 104301 | 145380_1 | AA768491 AA476251 AA809748 AI186268 AA621244 AI379029 BE550341 AA651915 AI216376 AI215585 AI471780 AA772159 AW181980 AI151169 AA759270 AI675769 AI018776 AA757335 AA148511 AI138378 AA504167 AI420617 AW261930 AW872797 N51769 AW614403 AI860533 AW573108 N64830 AI693732 AI436159 BE501089 AI436163 AA971485 AI269364 AI935358 AI222050 AW303978 AW573247 AI871154 T16758 AI765893 AW969016 AA744720 BE094085 AA743769 AI476407 AA156619 AI768535 R81435 D45332 N75682 N51177 AW207406 AA425184 R20997 AA504168 Z43298 |
| 134520 | 13358_3 | BE091005 BE541579 AW387738 AW386083 H13769 AW377820 AW369180 AW753239 AW672695 BE379572 AW021732 AW891450 AW891416 BE091358 N50375 BE091354 BE091365 BE091361 BE091350 AA353863 AA845510 N21407 AW770981 AI361577 AA526557 AA525443 AW893622 AA630898 AI418983 BE172016 AA550754 AA664574 C16147 AA355902 AW958586 N51590 C20995 BE544186 AI337578 AA090549 AI807374 AW450654 BE067578 AA446781 AA447058 T10807 AA457082 AI267703 AI880220 BE568979 AW380506 BE150744 AW380468 AW380546 BE150713 D60029 H88099 BE346301 BE150731 AW368467 BE091348 |
| 135242 | 5782_1 | AI583187 M73812 AW339829 M74093 BE252510 BE252518 BE536901 U40788 W95578 BE018493 BE544205 N83637 AI671049 AW439693 AW300786 AW374970 AA592960 AI215885 AI215884 BE302101 AI186210 AW771831 T54213 AW452924 AA834019 W95471 AA628312 AW304866 AA570076 AI559873 T54121 |
| 134621 | 27351_1 | AA037145 L02547 NM_001324 AW411516 AA314711 AA143605 BE394455 AA325731 AA093227 AA083307 BE299438 BE295669 AA370886 AA338272 AA166862 BE304837 BE298306 R60507 AW238966 N72750 AW505406 AW994153 AA309742 AA309929 BE090721 AW904189 AW904214 AA363564 R94127 AA352101 R28249 AA206337 AW577208 AA385473 AA355463 AA400696 AA075587 W72815 AA554033 AA075530 AA620555 AA554034 T27804 AW950014 AI570740 AI268538 AA704423 AW411517 AI278646 AW339924 AI668917 AI796034 AA994601 R94082 AW027137 AA400652 AW299746 W72816 AA988494 AA746582 AW087489 AA992763 AW516454 AA992759 AW270444 AA227188 AI208929 AA167720 AI052527 AA865660 AA569368 AI888464 AI670003 AA827620 AA507543 AI888385 R88418 AW959083 AI341077 AI825719 BE552285 AA738076 AW085903 R28242 |
| 126802 | 116467_4 | AW805510 AW805503 AW805500 AW805819 AW517040 AW473670 AW516701 T30141 AA894497 BE349504 AI272007 AI985274 BE501962 AW102975 AI801727 AW197918 T24046 AA947601 AW900958 |

TABLE 8B-continued

| Pkey | CAT Number | Accession |
|---|---|---|
| 126892 | 38252_1 | AF121856 BE242657 U83194 AA226732 AI160190 AA948725 AI079958 AW513369 W39443 AW408479 W06854 AA094683 AI985095 AA316647 H96313 N78438 R81582 H95034 R79674 AA488552 W25292 W31697 W19918 T30640 R08686 H78637 AA165100 Z41909 AA165080 R34212 AA150886 T82168 N77082 W56864 R19848 AA888217 AA314539 AW750293 N62714 R58039 AA845453 N63268 W03474 N41923 AI264123 AI808533 AA82488 AW198143 N99916 AA902465 AA775397 AA772387 AI567675 AA227473 AI082614 R58334 N78878 R34329 AW438902 AA164685 AA558790 AI590102 AA863422 BE002625 AA934039 AI298102 W15351 H93997 AA725325 BE180993 W05350 AI510771 W06941 AA488414 R79863 N91264 R76884 AA312948 T71267 AW959659 AI086695 N90421 AI278098 AA164538 AI30271 AA854381 R81331 AA700449 H06174 AW518427 AA876634 AA150778 N32393 H78585 T85364 BE002808 AW663196 N90337 BE252097 T71401 H06438 N40268 N31015 R77046 T99588 T85462 W25298 T59815 H09416 T85403 W32150 N79109 R78812 |
| 105298 | 8689_1 | BE387790 BE276849 BE246825 BE246900 AA380487 AA332996 AW408727 AK000294 AI636887 AW197272 AW590657 AW594006 AI768979 AI751632 AA58O098 AA313261 AA300475 AA133237 AA233499 BE242126 BE242597 BE242254 AA314374 W961210 AW939345 AA173535 AA305779 R99373 AA128304 AA447246 AA476365 T34973 BE264878 N25149 Z24939 BE263038 AA128317 Z46082 H23504 AW378551 AA088533 AA442625 H15235 H79172 AA344697 AA334742 AL040280 BE173129 T59749 AA084410 BE242311 AA173576 AA455337 AA129715 AA582953 AW612637 AA917038 AW340019 AW006315 AW593024 H05915 AW294592 AI146814 AW195659 AW440271 AI209090 AI288689 H98630 H15174 AI214454 AI569471 AA085808 AW188361 AI751631 AW440477 AW300860 AA516088 AI365108 AL305805 AI264064 AI246276 AA442611 AA807059 AA233459 AA875987 AI374653 AA972665 AA947515 AA436867 AI216423 AI657181 AI680306 AA436854 AI537153 AA883723 Z28659 AA705973 Z40741 AA463884 AI216025 AI564986 AA476316 AI432566 AI571662 AA447126 AW293675 AI675617 AW009004 H23498 |
| 120438 | 166102_1 | AW015242 AA831493 AI292346 AI076966 AI191561 AA243441 AI183309 AA252613 AI038422 AI306531 AW051480 AI348605 AA195119 AI817119 AI091896 AA738440 AA195013 AA976687 AA459659 AI246250 BE219252 AI703457 AA243291 AA989100 AA931640 AA459782 |
| 105516 | 9334_1 | AK00269 AL354613 AA147472 AA490803 BE207628 AW816113 AA085574 AW503392 AA299910 AW750305 BE079539 BE079484 BE512838 AK001593 AW968772 AW967440 AW206280 AA251270 AI627886 AA149960 Z44257 R12986 AA448446 AI734041 AA422167 BE220551 R66041 AI864512 AA204731 AA894490 BE001136 AA612785 AA237035 AA149990 Z44257 R12986 AA448446 AI734041 AA422167 BE220551 R66041 R32927 R32942 AA258773 AW386142 R53730 N54624 AW880296 AA253485 AW954441 H98989 AW614348 AI654838 AA779793 AW237213 N66635 AI186812 AA947479 BE158011 AI859480 AW805579 N52010 AA806305 AI628445 AW270990 AA778165 AA149949 AI650728 AA749108 AA687257 AI261661 AA747442 AA481351 AA206139 AA441306 AW473306 AA903407 AW473316 AA513150 AA976840 AA687117 AI281547 AA046243 R32825 AI631554 R32839 AW510564 AA436408 AA257971 AA253362 AA938330 AA513150 AA976840 AA687117 AI281547 AA046243 R32825 AI631554 AW139818 AI244536 R52946 AW235443 R40183 AA299909 AA811958 AI302918 Z40213 BE158047 BE158060 AA767245 AW748159 AW500735 AA094074 |
| 129097 | 25953_1 | BE243933 AA355449 T29766 F08396 N83324 NM_006963 S50223 AI207648 AA258092 AA113952 AI311718 AI128612 AW607449 M77172 AI951311 X52346 AA903307 AI569810 N55421 W77876 R37223 R83788 AA031666 H47092 AA133451 AA311095 AA906963 H87667 N56058 AA393593 W24864 H10710 F06925 F07239 AW386140 AA325018 AA235950 AW373176 N57158 AA258093 N39467 R21609 BE089979 R34173 AW889005 AA745644 AI693852 AA424914 AA744771 W72632 AI291213 AA524318 AI472134 AI911230 AA528418 AA115745 AA775720 AI671134 AA975047 AW298117 AA321015 N26288 AW952194 AI743379 AL204233 AI801026 AA830690 AI146980 AW104611 AI338576 R21507 AI367623 BE244484 AI269308 AA031667 AI884346 AA731989 AA988943 AA235951 AA807887 AA642645 AI246489 N29739 AI216718 AI383349 AI038618 AI351476 AA806031 AI914178 H10711 AI095573 H89220 AW470854 AA729015 R83353 AA782239 R34295 H87165 AW419059 AI653689 Z40349 H89114 AW074506 AA397785 AA888377 AI091228 F03193 AI468783 AA702615 AI830829 AA748323 R37224 AA424915 AA731647 H47183 |
| 120619 | 169895_1 | AW965339 AL045632 AA333229 AI806195 AA284372 AA206108 AA482533 AW449514 AA804785 AI215473 AI357262 AI651208 AI651753 |
| 129229 | 20927_1 | AF013758 NM_006451 AI538709 AA209236 AA300293 AA367274 AA126598 AA324825 AW955225 F11436 AW374740 AW374774 AW751514 W74780 AI909015 AW997079 AW997067 AW379344 AW363397 W38589 AA043823 BE169280 AI909016 AW994851 AI740638 AW148560 AW36339 AI858333 AA514718 AW954872 AW46734 AI681980 AW519045 AW055171 AA579286 AW069164 AW615904 AA345052 AI446735 AI142106 AA662683 AW002813 AI418280 AW613203 AI613333 AI354480 AI929755 AI146977 W74674 AW799610 AI798529 AI589422 AA043957 AI223043 AA157016 AI446759 D56729 AI584471 F30716 AA812125 AI537301 AA653347 D11966 AI434383 AA598533 AI287254 AW139140 AW051033 AA601911 AI702506 AA737460 T30221 AI129081 N90213 AA805225 AI798518 BE001071 T10841 W20199 AW664594 AW195667 D60123 D61496 AW468018 AI720097 N90553 AA829375 AW513266 H92758 AA585324 C14767 AI922391 D60124 D60666 AW071558 BE044120 AA728821 AA211941 |
| 120821 | 19274_2 | Y19062 NM_014393 AA347419 AI929333 AW196689 AI040867 F13437 AA918240 AI869798 AI365176 AW440030 AW440072 N80892 AW242030 Z44807 R21013 AA347419 AI929333 AW196689 AI040867 F13437 AA918240 AI869798 AI365176 AW440030 AW440072 N80892 AW242030 Z44807 R12417 AA436784 AA442041 AA046503 AL157526 AI929265 AA055542 AW519286 R12736 AW080147 AW136530 AI202958 AW241579 AW004719 AI810504 AL581093 AA493977 Z40600 F04553 R46130 F09321 |

TABLE 8B-continued

| Pkey | CAT Number | Accession |
|---|---|---|
| 106459 | 3897_1 | AA789081 AW408328 NM_006530 U61384 AA449641 AW138216 AA448598 AI245746 AI365301 N44728 AA255743 AA360783 BE550380 AW593925 AI962309 AA322097 AW964625 AI695988 AW672827 BE543256 AK001413 AW603395 AA651700 AA449053 AA465540 AW083185 T62128 Z78373 AW673713 AW468061 BE350755 AW673958 AW675504 AA995709 AW574841 AA835883 AI248439 AA548364 T62072 N33193 AA814046 AI376210 AI340020 AA449766 AA703407 AA427613 AI470108 AI298757 AA507602 AI658941 AA449478 AA633165 AA449741 AA831821 AA903673 AA682588 AW673075 |
| 115094 | 190995_1 | AA255920 AI817197 AA255921 AI612925 AW874669 AA493440 |
| 129571 | 1726_1 | X51630 M80232 X61631 S75264 AA172249 AA134066 AA130278 AA130187 AA130291 AA031534 AI246677 Z21455 AI745434 AW273544 AW08613 AW471307 AI745483 AI399854 AI683952 AA031555 AA298075 AI935945 T29809 AA172099 AA356120 |
| 121779 | 287665_1 | AW513143 AA422036 AI821669 AW514232 AA477828 AW772009 AW439799 AW089884 |
| 106738 | 174703_1 | AW149266 R49246 AW237401 AA938113 AW665871 AI969698 AI950812 AW874276 AI571939 AA741222 AI869822 AW104061 AI569994 AW972559 AA506012 AI553704 AA470145 AI332421 AA218990 AW131361 AI709076 AW392488 AW392477 AI970981 AW392476 D61949 H44981 BE172698 |
| 123005 | 75629_1 | AW369771 AW748174 AA249198 AA044331 AA172909 AW995442 AI480343 AA044582 AW956159 AA373451 AA127965 AL134913 AW994956 BE622314 BE006298 BE006312 BE006305 BE006317 BE006303 AA043906 AA234175 AA479726 |
| 108055 | 100690_1 | AJ404672 AJ289819 AW976000 AA043561 AW450885 AW452879 AA043562 AA788832 AI564338 AI564330 AI368875 AA643607 AA994375 AA810342 AI367704 BE545072 AI540751 AA301103 AI916675 N85422 BE563965 AA327978 AI816094 AK001515 BE501319 AA279943 BE138895 AA343765 |
| 115291 | 22325_1 | AW963051 AW082308 AI823992 AI653752 AI589007 AI816135 AI566535 BE501307 AW272765 AW242239 AA766315 AI014927 AA578848 AI354483 AI476548 AI038579 AA973322 AA992180 AW472921 BE504789 AI392988 AA506076 AA769228 AI370562 AL137710 BE005656 AW965920 |
| 130376 | 24827_4 | R40873 |
| 115536 | 61_1 | AK001468 AA190315 AA374980 AW961179 AA307782 AA315295 AA347194 AW953073 AW368190 AW368192 AA280772 AA251247 N85676 AI215522 AI216389 N87835 R12261 R57094 AI660045 AA347193 R16712 AW119006 N55905 N87768 AW900167 AI341261 AI818674 D20285 AI475165 AA300756 R40626 AI122827 AA133250 AI952488 AA970372 AA889845 AW069517 AI524385 AA190314 AI673359 AA971105 AI351088 AI872789 AI919056 AI611216 AK001472 BE568761 AA581004 |
| 114965 | 153955_1 | AI733881 AA165164 AI826437 AI972791 AA165165 BE219575 AI732586 AI821571 AA250737 AW136875 AI984273 AI249271 |
| 131228 | 8262_1 | AW207469 AL079814 AA354351 AF020043 AW291396 BE550484 NM_005445 BE046917 AW594249 AI651554 AI631515 AW771344 AI969758 AI699982 AA247175 AI244676 D44780 AW593978 AI638479 AI373676 AW089547 AL121432 AA554698 AI016991 AI087260 AW449939 AF067163 W40482 AW316558 AI537184 AW381979 W40150 AI810562 AA573151 AI630288 AI675561 AI674420 AW840733 AW022653 AA114219 AJ005015 AL046587 AA878141 AW271896 AW085287 AA150465 BE536295 AA463412 BE093222 AA213739 AA485586 AI825913 AA706307 AI337348 R31995 AI819641 R32095 AW976653 AA742375 AA142957 AI808214 AW468303 AI205987 AI206347 AI769095 BE501640 AA113866 AI093931 AI752855 AA612743 AA463411 AA279157 AI123791 AA213570 AI207305 AW627814 R31945 R32040 |
| 116238 | 10772_1 | AV660717 NM_015437 AL050285 R95774 AI867094 AA443833 AI367670 AA609046 AI440298 AI613139 AI291826 AW028954 AI123242 AI824715 AW079750 AW479362 AW150151 AI952267 AA814094 AI168431 AI566595 AI521422 AI920793 AW051241 N70051 AI689429 AI783813 AI769315 AI743691 AI915645 AA479473 C21435 N50944 N50902 AW978102 H23837 BE087538 AA316616 |
| 122802 | 287993_1 | AI687303 AI571681 AI554465 AI684252 AI581056 AA604098 AI628160 AI859843 AA424021 AA460530 BE042778 AW273200 AW273223 AW167288 AW083347 AI654306 AW517496 AW104706 AW2732114 BE139512 AW189487 AW130822 AW167419 AI289485 AW150010 H88004 AI743745 AW088710 |
| 123494 | 21202_1 | AW179019 AW179011 AF135160 NM_014050 AF078860 BE018005 AK000285 AF151038 BE245156 AW179007 AI345114 BE619758 BE619209 W25509 AA314339 AA336674 AA337956 AW954843 AW390412 N46796 AA316235 AA314286 R15686 BE535633 N57134 N46483 AW368462 AA923517 AA665223 AI418513 AA837523 AI359320 AI309273 AI522278 N46299 AA904977 AW938272 N30240 AA887965 AI671972 AI028109 AA094652 AA883262 AA887781 AI744447 AW592944 AI077790 AW860883 AW148667 N89861 AA557195 AI191824 AI433166 AI719760 AA453089 AA630656 AA300976 AA639620 AW675033 AA284393 AW886987 AI476335 AI332939 BE301513 AA452920 AW674302 AI925483 AW170412 AI698717 AI375985 BE220535 AI688151 AW514809 AW062346 AA599786 BE350848 AI023075 AA864875 AA166871 AI807947 AW514579 AI978602 AI860340 AA830886 AI374788 AI283592 AA683152 AA743159 AI379932 AI432056 AI128904 AW150338 N38909 |
| 116296 | 11967_2 | AW149502 Z43342 AW002826 AL049382 AA442545 AW971471 BE220243 AW968952 AA043607 AW299245 AA659892 AI038768 H26330 BE463534 AI628252 AA836139 AI277291 AA489033 AA741239 AI209064 AI300253 AI275761 Z39417 C01835 |

Pkey: Unique Eos probeset identifier number
CAT number: Gene cluster number
Accession: Genbank accession numbers Table 10A lists about 733 genes up-regulated in ovarian cancer compared to normal adult tissues. These were selected from 59680 probesets on the Affymetrix/Eos-Hu03 Gene-Chip array such that the ratio of "average" ovarian cancer to "average" normal adult tissues was greater than or equal to 3.0. The "average" ovarian cancer level was set to the about the 80th percentile amongst various ovarian cancers. The "average" normal adult tissue level was set to the 90th percentile value amongst various non-malignant tissues. In order to remove gene-specific background levels of non-specific hybridization, the 15th percentile value amongst the non-malignant tissues was subtracted from both the numerator and the denominator before the ratio was evaluated.

TABLE 10A

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 432938 | T27013 | Hs.3132 | steroidogenic acute regulatory protein | 56.1 |
| 418179 | X51630 | Hs.1145 | Wilms tumor 1 | 33.5 |
| 400292 | AA250737 | Hs.72472 | BMPR-lb; bone morphogenetic protein receptor | 30.0 |
| 452838 | U65011 | Hs.30743 | Preferentially expressed antigen in melanoma | 29.5 |
| 415511 | AI732617 | Hs.182362 | ESTs | 28.1 |
| 422956 | BE545072 | Hs.122579 | ESTs | 28.1 |
| 410929 | H47233 | Hs.30643 | ESTs | 27.4 |
| 400289 | X07820 | Hs.2258 | Matrix Metalloproteinase 10 (Stromolysin 2) | 25.2 |
| 449034 | AI624049 | Hs.277523 | gb: ts41a09.x1 NCI_CGAP_Ut1 *Homo sapiens* cDNA | 23.7 |
| 427585 | D31152 | Hs.179729 | collagen; type X; alpha 1 (Schmid metaphyseal | 22.7 |
| 428392 | H10233 | Hs.2265 | secretory granule, neuroendocrine protein 1 | 21.9 |
| 448243 | AW369771 | Hs.77496 | ESTs | 21.3 |
| 430691 | C14187 | Hs.103538 | ESTs | 21.2 |
| 444783 | AK001468 | Hs.62180 | ESTs | 20.8 |
| 407638 | AJ404672 | Hs.288693 | EST | 20.1 |
| 423739 | AA398155 | Hs.97600 | ESTs | 19.7 |
| 436982 | AB018305 | Hs.5378 | spondin 1, (f-spondin) extracellular matrix p | 19.0 |
| 451110 | AI955040 | Hs.301584 | ESTs | 18.8 |
| 426427 | M86699 | Hs.169840 | TTK protein kinase | 18.7 |
| 428227 | AA321649 | Hs.2248 | INTERFERON-GAMMA INDUCED | 18.3 |
| 419854 | AW664873 | Hs.87836 | *Homo sapiens* PAC clone RP5-1087M19 from 7q11. | 18.3 |
| 439706 | AW872527 | Hs.59761 | ESTs | 18.3 |
| 428579 | NM_005756 | Hs.184942 | G protein-coupled receptor 64 | 17.4 |
| 410247 | AF181721 | Hs.61345 | RU2S | 17.0 |
| 428153 | AW513143 | Hs.98367 | hypothetical protein FLJ22252 similar to SRY- | 16.9 |
| 415076 | NM_000857 | Hs.77890 | guanylate cyclase 1, soluble, beta 3 | 16.6 |
| 416209 | AA236776 | Hs.79078 | MAD2 (mitotic arrest deficient, yeast, homolo | 16.6 |
| 424905 | NM_002497 | Hs.153704 | NIMA (never in mitosis gene a)-related kinase | 16.2 |
| 423685 | BE350494 | Hs.49753 | *Homo sapiens* mRNA for KIAA1561 protein, parti | 15.9 |
| 428187 | AI687303 | Hs.285529 | ESTs | 15.9 |
| 438817 | AI023799 | Hs.163242 | ESTs | 15.9 |
| 424906 | AI566086 | Hs.153716 | *Homo sapiens* mRNA for Hmob33 protein, 3' untr | 15.9 |
| 407721 | Y12735 | Hs.38018 | dual-specificity tyrosine-(Y)-phosphorylation | 15.7 |
| 412723 | AA648459 | Hs.179912 | ESTs | 15.3 |
| 424717 | H03754 | Hs.152213 | wingless-type MMTV integration site family, m | 15.2 |
| 443646 | AI085198 | Hs.298699 | ESTs | 15.1 |
| 424345 | AK001380 | Hs.145479 | *Homo sapiens* cDNA FLJ10518 fis, clone NT2RP20 | 14.8 |
| 428976 | AL037824 | Hs.194695 | ras homolog gene family, member I | 14.6 |
| 418738 | AW388633 | Hs.6682 | solute carrier family 7, member 11 | 14.3 |
| 428479 | Y00272 | Hs.184572 | cell division cycle 2, G1 to S and G2 to M | 14.2 |
| 436209 | AW850417 | Hs.254020 | ESTs, Moderately similar to unnamed protein p | 14.1 |
| 427356 | AW023482 | Hs.97849 | ESTs | 13.9 |
| 418601 | AA279490 | Hs.86368 | calmegin | 13.8 |
| 416661 | AA634543 | Hs.79440 | IGF-II mRNA-binding protein 3 | 13.7 |
| 428532 | AF157326 | Hs.184786 | TBP-interacting protein | 13.6 |
| 402408 | | | 0 | 13.6 |
| 447350 | AI375572 | Hs.172634 | ESTs; HER4 (c-erb-B4) | 13.4 |
| 451807 | W52854 | Hs.27099 | DKFZP564J0863 protein | 13.4 |
| 423575 | C18863 | Hs.163443 | ESTs | 13.2 |
| 443211 | AI128388 | Hs.143655 | ESTs | 13.2 |
| 437872 | AK002015 | Hs.5887 | RNA binding motif protein 7 | 13.0 |
| 451659 | BE379761 | Hs.14248 | ESTs, Weakly similar to ALU8_HUMAN ALU SUBFAM | 12.7 |
| 452904 | AL157581 | Hs.30957 | *Homo sapiens* mRNA; cDNA DKFZp434E0626 (from c | 12.7 |
| 442655 | AW027457 | Hs.30323 | ESTs | 12.5 |
| 452096 | BE394901 | Hs.226785 | ESTs | 12.4 |
| 414972 | BE263782 | Hs.77695 | KIAA0008 gene product | 12.3 |
| 435039 | AW043921 | Hs.130526 | ESTs | 12.3 |
| 447033 | AI357412 | Hs.157601 | EST - not in UniGene | 12.3 |
| 433764 | AW753676 | Hs.39982 | ESTs | 12.2 |
| 442611 | BE077155 | Hs.177537 | ESTs | 12.0 |
| 408562 | AI436323 | Hs.31141 | *Homo sapiens* mRNA for KIAA31568 protein, parti | 11.9 |
| 427344 | NM_000869 | Hs.2142 | 5-hydroxytryptamine (serotonin) receptor 3A | 11.8 |
| 421478 | AI683243 | Hs.97258 | ESTs | 11.8 |
| 426635 | BE395109 | Hs.129327 | ESTs | 11.8 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 415989 | AI267700 | Hs.111128 | ESTs | 11.7 |
| 433159 | AB035898 | Hs.150587 | kinesin-like protein 2 | 11.5 |
| 452249 | BE394412 | Hs.61252 | ESTs | 11.4 |
| 418506 | AA084248 | Hs.85339 | G protein-coupled receptor 39 | 11.3 |
| 442353 | BE379594 | Hs.49136 | ESTs | 11.3 |
| 447700 | AI420183 | Hs.171077 | ESTs, Weakly similar to similar to serine/thr | 11.3 |
| 450480 | X82125 | Hs.25040 | zinc finger protein 239 | 11.3 |
| 425176 | AW015644 | Hs.301430 | ESTs, Moderately similar to TEF1_HUMAN TRANSC | 11.2 |
| 435496 | AW840171 | Hs.265398 | ESTs, Weakly similar to transformation-relate | 11.2 |
| 433133 | AB027249 | Hs.104741 | PDZ-binding kinase; T-cell originated protein | 11.1 |
| 445258 | AI635931 | Hs.147613 | ESTs | 11.1 |
| 432677 | NM_004482 | Hs.278611 | UDP-N-acetyl-alpha-D-galactosamine:polypeptid | 11.0 |
| 429782 | NM_005754 | Hs.220689 | Ras-GTPase-activating protein SH3-domain-bind | 10.9 |
| 404567 | | | 0 | 10.8 |
| 423811 | AW299598 | Hs.50895 | homeo box C4 | 10.7 |
| 452891 | N75582 | Hs.212875 | ESTs, Weakly similar to KIAA0357 [*H. sapiens*] | 10.6 |
| 441627 | AA947552 | Hs.58086 | ESTs | 10.3 |
| 443555 | N71710 | Hs.21398 | ESTs, Moderately similar to GNPI_HUMAN GLUCOS | 10.3 |
| 412140 | AA219691 | Hs.73625 | RAB6 interacting, kinesin-like (rabkinesin6) | 10.2 |
| 427469 | AA403084 | Hs.269347 | ESTs | 10.1 |
| 415227 | AW821113 | Hs.72402 | ESTs | 10.1 |
| 445413 | AA151342 | Hs.12677 | CGI-147 protein | 10.0 |
| 425734 | AF056209 | Hs.159396 | peptidylglycine alpha-amidating monooxygenase | 10.0 |
| 421451 | AA291377 | Hs.50831 | ESTs | 10.0 |
| 410044 | BE566742 | Hs.58169 | highly expressed in cancer, rich in leucine h | 9.8 |
| 427878 | C05766 | Hs.181022 | CGI-07 protein | 9.7 |
| 408460 | AA054726 | Hs.285574 | ESTs | 9.7 |
| 422972 | N59319 | Hs.145404 | ESTs | 9.7 |
| 443715 | AI583187 | Hs.9700 | cyclin E1 | 9.7 |
| 440901 | AA909358 | Hs.128612 | ESTs | 9.6 |
| 453160 | AI263307 | Hs.146228 | ESTs | 9.6 |
| 415211 | R64730.comp | Hs.155986 | ESTs; Highly similar to SPERM SURFACE PROTEIN | 9.5 |
| 425282 | AW163518 | Hs.155485 | huntingtin interacting protein 2 | 9.5 |
| 400250 | | | 0 | 9.5 |
| 410568 | AW162948 | Hs.64542 | pre-mRNA cleavage factor Im (68 kD) | 9.3 |
| 442957 | AI949952 | Hs.49397 | ESTs | 9.3 |
| 453922 | AF053306 | Hs.36708 | budding uninhibited by benzimidazoles 1 (yeas | 9.3 |
| 434401 | AI864131 | Hs.71119 | Putative prostate cancer tumor suppressor | 9.2 |
| 453628 | AW243307 | Hs.170187 | ESTs | 9.1 |
| 452055 | AI377431 | Hs.293772 | ESTs | 9.1 |
| 424086 | AI351010 | Hs.102267 | lysyl oxidase | 9.1 |
| 442875 | BE623003 | Hs.23625 | *Homo sapiens* clone TCCCTA00142 mRNA sequence | 9.1 |
| 416208 | AW291168 | Hs.41295 | ESTs | 9.0 |
| 407168 | R45175 | Hs.117183 | gb: yg40f01.s1 Soares infant brain 1NIB *Homo s* | 9.0 |
| 445537 | AJ245671 | Hs.12844 | EGF-like-domain; multiple 6 | 8.9 |
| 409269 | AA576953 | Hs.22972 | *Homo sapiens* cDNA FLJ13352 fis, clone OVARC10 | 8.9 |
| 433527 | AW235613 | Hs.133020 | ESTs | 8.9 |
| 409928 | AL137163 | Hs.57549 | hypothetical protein dJ473B4 | 8.8 |
| 423020 | AA383092 | Hs.1608 | replication protein A3 (14 kD) | 8.7 |
| 425665 | AK001050 | Hs.159066 | ESTs | 8.6 |
| 443204 | AW205878 | Hs.29643 | *Homo sapiens* cDNA FLJ13103 fis, clone NT2RP30 | 8.6 |
| 449433 | AI672096 | Hs.9012 | ESTs | 8.6 |
| 453878 | AW964440 | Hs.19025 | ESTs | 8.6 |
| 450505 | NM_004572 | Hs.25051 | plakophilin 2 | 8.6 |
| 407001 | U12471 | Hs.247954 | Human thrombospondin-1 gene, partial cds | 8.5 |
| 414315 | Z24878 | | gb: HSB65D052 STRATAGENE Human skeletal muscle | 8.5 |
| 425492 | AL021918 | Hs.158174 | zinc finger protein 184 (Kruppel-like) | 8.5 |
| 435181 | AA669339 | Hs.28838 | KIAA1571 protein | 8.5 |
| 436396 | AI683487 | Hs.299112 | *Homo sapiens* cDNA FLJ11441 fis, clone HEMBA10 | 8.5 |
| 418384 | AW149266 | Hs.25130 | ESTs | 8.4 |
| 453370 | AI470523 | Hs.182356 | ESTs, Moderately similar to translation initi | 8.4 |
| 409041 | AB033025 | Hs.50081 | KIAA1199 protein | 8.4 |
| 447078 | AW885727 | Hs.301570 | ESTs | 8.4 |
| 448674 | W31178 | Hs.154140 | ESTs | 8.3 |
| 433393 | AF038564 | Hs.98074 | atrophin-1 interacting protein 4 | 8.3 |
| 433496 | AF064254 | Hs.49765 | VERY-LONG-CHAIN ACYL-COA SYNTHETASE | 8.3 |
| 421155 | H87879 | Hs.102267 | lysyl oxidase | 8.2 |
| 438394 | BE379623 | Hs.27693 | CGI-124 protein | 8.2 |
| 400298 | AA032279 | Hs.61635 | STEAP1 | 8.1 |
| 409092 | AI735283 | Hs.172608 | ESTs | 8.1 |
| 440250 | AA876179 | Hs.134650 | ESTs | 8.1 |
| 409143 | AW025980 | Hs.138965 | ESTs | 8.1 |
| 407771 | AL138272 | Hs.62713 | ESTs | 8.1 |
| 419088 | AI538323 | Hs.77496 | ESTs | 8.1 |
| 431725 | X65724 | Hs.2839 | Norrie disease (pseudoglioma) | 7.9 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 431750 | AA514986 | Hs.283705 | ESTs | 7.9 |
| 435635 | AF220050 | Hs.181385 | uncharacterized hematopoietic stem/progenitor | 7.9 |
| 441826 | AW503603 | Hs.129915 | phosphotriesterase related | 7.9 |
| 417728 | AW138437 | Hs.24790 | KIAA1573 protein | 7.8 |
| 418845 | AA852985 | Hs.89232 | chromobox homolog 5 (*Drosophila* HP1 alpha) | 7.8 |
| 421039 | NM_003478 | Hs.101299 | cullin 5 | 7.8 |
| 446999 | AA151520 | Hs.279525 | hypothetical protein PRO2605 | 7.8 |
| 429609 | AF002246 | Hs.210863 | cell adhesion molecule with homology to L1CAM | 7.8 |
| 415139 | AW975942 | Hs.48524 | ESTs | 7.7 |
| 450192 | AA263143 | Hs.24596 | RAD51-interacting protein | 7.7 |
| 423992 | AW898292 | Hs.137206 | *Homo sapiens* mRNA; cDNA DKFZp564H1663 (from c | 7.7 |
| 436211 | AK001581 | Hs.80961 | polymerase (DNA directed), gamma | 7.7 |
| 450101 | AV649989 | Hs.24385 | Human hbc647 mRNA sequence | 7.5 |
| 426921 | AA037145 | Hs.172865 | cleavage stimulation factor, 3' pre-RNA, subu | 7.5 |
| 433330 | AW207084 | Hs.132816 | ESTs | 7.5 |
| 439759 | AL359055 | Hs.67709 | *Homo sapiens* mRNA full length insert cDNA clo | 7.5 |
| 427660 | AI741320 | Hs.114121 | *Homo sapiens* cDNA: FLJ23228 fis, clone CAE066 | 7.5 |
| 422095 | AI868872 | Hs.288966 | ceruloplasmin (ferroxidase) | 7.5 |
| 436476 | AA326108 | Hs.53631 | ESTs | 7.5 |
| 412170 | D16532 | Hs.73729 | very low density lipoprotein receptor | 7.4 |
| 428954 | AF100781 | Hs.194678 | WNT1 inducible signaling pathway protein 3 | 7.4 |
| 450221 | AA328102 | Hs.24641 | cytoskeleton associated protein 2 | 7.4 |
| 439262 | AA832333 | Hs.124399 | ESTs | 7.4 |
| 435420 | AI928513 | Hs.59203 | ESTs | 7.3 |
| 422892 | AA988176 | Hs.121553 | hypothetical protein FLJ20641 | 7.3 |
| 457030 | AI301740 | Hs.173381 | dihydropyrimidinase-like 2 | 7.3 |
| 411571 | AA122393 | Hs.70811 | hypothetical protein FLJ20516 | 7.2 |
| 409916 | BE313625 | Hs.57435 | solute carrier family 11 (proton-coupled diva | 7.2 |
| 418007 | M13509 | Hs.83169 | Matrix metalloprotease 1 (interstitial collag | 7.2 |
| 420900 | AL045633 | Hs.44269 | ESTs | 7.2 |
| 424001 | W67883 | Hs.137476 | KIAA1051 protein | 7.2 |
| 400301 | X03635 | Hs.1657 | Estrogen receptor 1 | 7.1 |
| 400238 | | | 0 | 7.1 |
| 413573 | AI733859 | Hs.149089 | ESTs | 7.1 |
| 428071 | AF212848 | Hs.182339 | transcription factor ESE-3B | 7.1 |
| 447164 | AF026941 | Hs.17518 | *Homo sapiens* cig5 mRNA, partial sequence | 7.1 |
| 453062 | AW207538 | Hs.61603 | ESTs | 7.1 |
| 456965 | AW131888 | Hs.172792 | ESTs, Weakly similar to hypothetical protein | 7.1 |
| 442500 | AI819068 | Hs.209122 | ESTs | 7.1 |
| 446142 | AI754693 | Hs.145968 | ESTs | 7.0 |
| 417791 | AW965339 | Hs.111471 | ESTs | 7.0 |
| 418524 | AA300576 | Hs.85769 | acidic 82 kDa protein mRNA | 7.0 |
| 451797 | AW663858 | Hs.56120 | ESTs | 7.0 |
| 452909 | NM_015368 | Hs.30985 | pannexin 1 | 7.0 |
| 453616 | NM_003462 | Hs.33846 | dynein, axonemal, light intermediate polypept | 7.0 |
| 436281 | AW411194 | Hs.120051 | ESTs | 7.0 |
| 449897 | AW819642 | Hs.24135 | transmembrane protein vezatin; hypothetical p | 6.9 |
| 414142 | AW368397 | Hs.150042 | ESTs | 6.9 |
| 448776 | BE302464 | Hs.30057 | transporter similar to yeast MRS2 | 6.9 |
| 419423 | D26488 | Hs.90315 | KIAA0007 protein | 6.9 |
| 420908 | AL049974 | Hs.100261 | *Homo sapiens* mRNA; cDNA DKFZp564B222 (from cl | 6.8 |
| 452971 | AI873878 | Hs.91789 | ESTs | 6.8 |
| 413597 | AW302885 | Hs.117183 | ESTs | 6.8 |
| 415138 | C18356 | Hs.78045 | tissue factor pathway inhibitor 2 TFPI2 | 6.8 |
| 437478 | AL390172 | Hs.118811 | ESTs | 6.7 |
| 425292 | NM_005824 | Hs.155545 | 37 kDa leucine-rich repeat (LRR) protein | 6.7 |
| 421184 | NM_003616 | Hs.102456 | survival of motor neuron protein interacting | 6.7 |
| 410227 | AB009284 | Hs.61152 | exostoses (multiple)-like 2 | 6.6 |
| 446608 | N75217 | Hs.257846 | ESTs | 6.6 |
| 438167 | R28363 | Hs.24286 | ESTs | 6.6 |
| 445459 | AI478629 | Hs.158465 | ESTs | 6.6 |
| 452291 | AF015592 | Hs.28853 | CDC7 (cell division cycle 7, *S. cerevisiae*, h | 6.6 |
| 410011 | AB020641 | Hs.57856 | PFTAIRE protein kinase 1 | 6.6 |
| 410292 | AA843087 | Hs.124194 | ESTs | 6.5 |
| 415716 | N59294 | Hs.301141 | *Homo sapiens* cDNA FLJ11689 fis, clone HEMBA10 | 6.5 |
| 424770 | AA425562 | | gb: zw46e05.r1 Soares_total_fetus_Nb2HF8_9w Ho | 6.5 |
| 438122 | AI620270 | Hs.129837 | ESTs | 6.5 |
| 439820 | AL360204 | Hs.283853 | *Homo sapiens* mRNA full length insert cDNA clo | 6.5 |
| 444743 | AA045648 | Hs.11817 | nudix (nucleoside diphosphate linked moiety X | 6.5 |
| 450638 | AK001826 | Hs.25245 | hypothetical protein FLJ11269 | 6.5 |
| 418203 | X54942 | Hs.83758 | CDC28 protein kinase 2 | 6.5 |
| 439901 | N73885 | Hs.124169 | ESTs | 6.5 |
| 428758 | AA433988 | Hs.98502 | *Homo sapiens* cDNA FLJ14303 fis, clone PLACE20 | 6.4 |
| 404552 | | | 0 | 6.4 |
| 404599 | | | 0 | 6.4 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 419503 | AA243642 | Hs.137422 | ESTs | 6.4 |
| 420149 | AA255920 | Hs.88095 | ESTs | 6.4 |
| 440411 | N30256 | Hs.156971 | ESTs, Weakly similar to Weak similarity with | 6.4 |
| 449108 | AI140683 | Hs.98328 | ESTs | 6.4 |
| 452097 | AB002364 | Hs.27916 | ADAM-TS3; a disintegrin-like and metallopr | 6.4 |
| 453619 | H87648 | Hs.33922 | *H. sapiens* novel gene from PAC 117P20, chromos | 6.4 |
| 410273 | BE326877 | Hs.281523 | ESTs | 6.3 |
| 434486 | AA678816 | Hs.117142 | ESTs | 6.3 |
| 454036 | AA374756 | Hs.93560 | ESTs, Weakly similar to unnamed protein produ | 6.3 |
| 403381 | | | 0 | 6.2 |
| 421308 | AA687322 | Hs.192843 | ESTs | 6.2 |
| 419346 | AI830417 | | gb: wh94d12.x1 NCI_CGAP_CLL1 *Homo sapiens* cDNA | 6.2 |
| 446140 | AA356170 | Hs.26750 | *Homo sapiens* cDNA: FLJ21908 fis, clone HEP038 | 6.2 |
| 453047 | AW023798 | Hs.286025 | ESTs | 6.2 |
| 442573 | H93366 | Hs.7567 | Branched chain aminotransferase 1, cytosolic, | 6.1 |
| 410102 | AW248508 | Hs.279727 | ESTs; | 6.1 |
| 410004 | AI298027 | Hs.299115 | ESTs | 6.1 |
| 413335 | AI613318 | Hs.48442 | ESTs | 6.1 |
| 424945 | AI221919 | Hs.173438 | hypothetical protein FLJ10582 | 6.1 |
| 427510 | Z47542 | Hs.179312 | small nuclear RNA activating complex, polypep | 6.1 |
| 451229 | AW967707 | Hs.48473 | ESTs | 6.1 |
| 452641 | AW952893 | Hs.237825 | signal recognition particle 72 kD | 6.1 |
| 433172 | AB037841 | Hs.102652 | hypothetical protein ASH1 | 6.1 |
| 425465 | L18964 | Hs.1904 | protein kinase C; iota | 6.1 |
| 437117 | AL049256 | Hs.122593 | ESTs | 6.0 |
| 423440 | R25234 | Hs.143434 | contactin 1 | 6.0 |
| 430510 | AW162916 | Hs.241576 | hypothetical protein PRO2577 | 6.0 |
| 433252 | AB040957 | Hs.151343 | KIAA1524 protein | 6.0 |
| 434699 | AA643687 | Hs.149425 | *Homo sapiens* cDNA FLJ11980 fis, clone HEMBB10 | 6.0 |
| 436954 | AA740151 | Hs.130425 | ESTs | 5.9 |
| 436032 | AA150797 | Hs.109276 | latexin protein | 5.9 |
| 424590 | AW966399 | Hs.46821 | hypothetical protein FLJ20086 | 5.9 |
| 444078 | BE246919 | Hs.10290 | U5 snRNP-specific 40 kDa protein (hPrp8-bindi | 5.9 |
| 418379 | AA218940 | Hs.137516 | fidgetin-like 1 | 5.9 |
| 438081 | H49546 | Hs.298964 | ESTs | 5.8 |
| 443270 | NM_004272 | Hs.9192 | Homer, neuronal immediate early gene, 1B | 5.8 |
| 450459 | AI697193 | Hs.299254 | ESTs | 5.8 |
| 433612 | AF078164 | Hs.61188 | *Homo sapiens* Ku70-binding protein (KUB3) mRNA | 5.8 |
| 449048 | Z45051 | Hs.22920 | similar to S68401 (cattle) glucose induced ge | 5.8 |
| 417251 | AW015242 | Hs.99488 | ESTs; Weakly similar to ORF YKR074w [*S. cerevi* | 5.7 |
| 429181 | AW979104 | Hs.294009 | ESTs | 5.7 |
| 454933 | BE141714 | | gb: QV0-HT0101-061099-032-c04 HT0101 *Homo sapi* | 5.7 |
| 456553 | AA721325 | Hs.189058 | ESTs, Weakly similar to cAMP-regulated guanin | 5.7 |
| 430371 | D87466 | Hs.240112 | KIAA0276 protein | 5.7 |
| 425371 | D49441 | Hs.155981 | mesothelin | 5.7 |
| 424513 | BE385864 | Hs.149894 | mitochondrial translational initiation factor | 5.6 |
| 432015 | AL157504 | Hs.159115 | ESTs | 5.6 |
| 438109 | AI076621 | Hs.71367 | ESTs, Moderately similar to ALU7_HUMAN ALU SU | 5.6 |
| 407137 | T97307 | Hs.199067 | v-erb-b2 avian erythroblastic leukemia viral | 5.6 |
| 407945 | X69208 | Hs.606 | ATPase, Cu++ transporting, alpha polypeptide | 5.6 |
| 416565 | AW000960 | Hs.44970 | ESTs | 5.6 |
| 417830 | AW504786 | Hs.132808 | epithelial cell transforming sequence 2 oncog | 5.5 |
| 419752 | AA249573 | Hs.152618 | ESTs | 5.5 |
| 422093 | AF151852 | Hs.111449 | CGI-94 protein | 5.5 |
| 424583 | AF017445 | Hs.150926 | fucose-1-phosphate guanylyltransferase | 5.5 |
| 430388 | AA356923 | Hs.240770 | nuclear cap binding protein subunit 2, 20 kD | 5.5 |
| 452534 | AW083022 | Hs.149425 | *Homo sapiens* cDNA FLJ11980 fis, clone HEMBB10 | 5.5 |
| 453279 | AW893940 | Hs.59698 | ESTs | 5.5 |
| 424188 | AW954552 | Hs.142634 | zinc finger protein | 5.5 |
| 453884 | AA355925 | Hs.36232 | KIAA0186 gene product | 5.5 |
| 424641 | AB001106 | Hs.151413 | glia maturation factor, beta | 5.5 |
| 444478 | W07318 | Hs.240 | M-phase phosphoprotein 1 | 5.5 |
| 427975 | AI536065 | Hs.122460 | ESTs | 5.5 |
| 424620 | AA101043 | Hs.151254 | kallikrein 7 (chymotryptic; stratum corneum) | 5.5 |
| 442914 | AW188551 | Hs.99519 | *Homo sapiens* cDNA FLJ14007 fis, clone Y79AA10 | 5.5 |
| 417995 | AW974175 | Hs.188751 | ESTs | 5.4 |
| 418946 | AI798841 | Hs.132103 | ESTs | 5.4 |
| 419963 | AA743276 | Hs.301052 | ESTs | 5.4 |
| 420362 | U79734 | Hs.97206 | huntingtin interacting protein 1 | 5.4 |
| 422670 | AA371612 | Hs.115351 | ESTs | 5.4 |
| 432837 | AA310693 | Hs.279512 | HSPC072 protein | 5.4 |
| 447020 | T27308 | Hs.16986 | hypothetical protein FLJ11046 | 5.4 |
| 458027 | L49054 | Hs.85195 | ESTs, Highly similar to t(3; 5)(q25.1; p34) fus | 5.4 |
| 425217 | AU076696 | Hs.155174 | CDC5 (cell division cycle 5, *S. pombe*, homolo | 5.4 |
| 422938 | NM_001809 | Hs.1594 | centromere protein A (17 kD) | 5.4 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 450434 | AA166950 | Hs.18645 | ESTs, Weakly similar to partial CDS [*C. elegan* | 5.4 |
| 438279 | AA805166 | Hs.165165 | ESTs, Moderately similar to ALU8_HUMAN ALU SU | 5.4 |
| 413384 | NM_000401 | Hs.75334 | exostoses (multiple) 2 | 5.3 |
| 420328 | Y19062 | Hs.96870 | staufen (*Drosophila*, RNA-binding protein) hom | 5.3 |
| 436586 | AI308862 | Hs.167028 | ESTs | 5.3 |
| 435793 | AB037734 | Hs.4993 | ESTs | 5.3 |
| 422306 | BE044325 | Hs.227280 | *Homo sapiens* mRNA for Lsm5 protein | 5.3 |
| 425154 | NM_001851 | Hs.154850 | collagen, type IX, alpha 1 | 5.2 |
| 453293 | AA382267 | Hs.10653 | ESTs | 5.2 |
| 429944 | R13949 | Hs.226440 | *Homo sapiens* clone 24881 mRNA sequence | 5.2 |
| 434891 | AA814309 | Hs.123583 | ESTs | 5.2 |
| 415263 | AA948033 | Hs.130853 | ESTs | 5.2 |
| 409506 | NM_006153 | Hs.54589 | NCK adaptor protein 1 | 5.2 |
| 412848 | AA121514 | Hs.70832 | ESTs | 5.2 |
| 421246 | AW582962 | Hs.300961 | ESTs, Highly similar to AF151805 1 CGI-47 pro | 5.2 |
| 431548 | AI834273 | Hs.9711 | *Homo sapiens* cDNA FLJ13018 fis, clone NT2RP30 | 5.2 |
| 412719 | AW016610 | Hs.129911 | ESTs | 5.2 |
| 411945 | AL033527 | Hs.92137 | v-myc avian myelocytomatosis viral oncogene h | 5.1 |
| 424078 | AB006625 | Hs.139033 | paternally expressed gene 3 | 5.1 |
| 433558 | AA833757 | Hs.201769 | ESTs | 5.1 |
| 434265 | AA846811 | Hs.130554 | *Homo sapiens* cDNA: FLJ23089 fis, clone LNG070 | 5.1 |
| 453911 | AW503857 | Hs.4007 | Sarcolemmal-associated protein | 5.1 |
| 415539 | AI733881 | Hs.72472 | BMPR-lb; bone morphogenetic protein receptor | 5.1 |
| 442717 | R88362 | Hs.180591 | ESTs, Weakly similar to R06F6.5b [*C. elegans*] | 5.1 |
| 432358 | AI093491 | Hs.72830 | ESTs | 5.0 |
| 409731 | AA125985 | Hs.56145 | thymosin, beta, identified in neuroblastoma c | 5.0 |
| 419699 | AA248998 | Hs.31246 | ESTs | 5.0 |
| 420313 | AB023230 | Hs.96427 | KIAA1013 protein | 5.0 |
| 422505 | AL120862 | Hs.124165 | ESTs; (HSA)PAP protein (programmed cell deat | 5.0 |
| 425733 | F13287 | Hs.159388 | *Homo sapiens* clone 23578 mRNA sequence | 5.0 |
| 434160 | BE551196 | Hs.114275 | ESTs | 5.0 |
| 435094 | AI560129 | Hs.277523 | EST | 5.0 |
| 436812 | AW298067 | | gb: UI-H-BW0-ajp-g-09-0-UI.s1 NCI_CGAP_Sub6 *Ho* | 5.0 |
| 432415 | T16971 | Hs.289014 | ESTs | 4.9 |
| 406117 | | | 0 | 4.9 |
| 438018 | AK001160 | Hs.5999 | hypothetical protein FLJ10298 | 4.9 |
| 447505 | AL049266 | Hs.18724 | *Homo sapiens* mRNA; cDNA DKFZp564F093 (from cl | 4.9 |
| 448621 | AI097144 | Hs.5250 | ESTs, Weakly similar to BACR37P7.g [*D. melanog* | 4.9 |
| 453001 | AW131636 | Hs.191260 | ESTs | 4.9 |
| 410561 | BE540255 | Hs.6994 | *Homo sapiens* cDNA: FLJ22044 fis, clone HEP091 | 4.9 |
| 418811 | AK001407 | Hs.88663 | hypothetical protein FLJ10545 | 4.9 |
| 436754 | AI061288 | Hs.133437 | ESTs, Moderately similar to gonadotropin indu | 4.8 |
| 437212 | AI765021 | Hs.210775 | ESTs | 4.8 |
| 447312 | AI434345 | Hs.36908 | activating transcription factor 1 | 4.8 |
| 409732 | NM_016122 | Hs.56148 | NY-REN-58 antigen | 4.8 |
| 434690 | AI867679 | Hs.148410 | ESTs | 4.8 |
| 444172 | BE147740 | Hs.104558 | ESTs | 4.8 |
| 424539 | L02911 | Hs.150402 | activin A receptor, type I | 4.8 |
| 418677 | S83308 | Hs.87224 | SRY (sex determining region Y)-box 5 | 4.8 |
| 406076 | AL390179 | Hs.137011 | *Homo sapiens* mRNA; cDNA DKFZp547P134 (from cl | 4.8 |
| 420179 | N74530 | Hs.21168 | ESTs | 4.7 |
| 450375 | AA009647 | Hs.8850 | a disintegrin and metalloproteinase domain 12 | 4.7 |
| 419247 | S65791 | Hs.89764 | fragile X mental retardation 1 | 4.7 |
| 420850 | BE139590 | Hs.122406 | ESTs | 4.7 |
| 425420 | BE536911 | Hs.234545 | ESTs | 4.7 |
| 428664 | AK001666 | Hs.189095 | similar to SALL1 (sal (*Drosophila*)-like | 4.7 |
| 419131 | AA406293 | Hs.301622 | ESTs | 4.7 |
| 422278 | AF072873 | Hs.114218 | ESTs | 4.7 |
| 451684 | AF216751 | Hs.26813 | CDA14 | 4.6 |
| 400296 | AA305627 | Hs.139336 | ATP-binding cassette; sub-family C (CFTR/MRP) | 4.6 |
| 408425 | AW058674 | Hs.44787 | *Homo sapiens* mRNA; cDNA DKFZp434O0227 (from c | 4.6 |
| 417168 | AL133117 | Hs.81376 | *Homo sapiens* mRNA; cDNA DKFZp586L1121 (from c | 4.6 |
| 429486 | AF155827 | Hs.203963 | hypothetical protein FLJ10339 | 4.6 |
| 442917 | AA314907 | Hs.85950 | ESTs | 4.6 |
| 443268 | AI800271 | Hs.129445 | hypothetical protein FLJ12496 | 4.6 |
| 452795 | AW392555 | Hs.18878 | hypothetical protein FLJ21620 | 4.6 |
| 457300 | AW297436 | Hs.158849 | *Homo sapiens* cDNA: FLJ21663 fis, clone COL088 | 4.6 |
| 459551 | AI472808 | | gb: tj70e07.x1 Soares_NSF_F8_9W_OT_PA_P_S1 *Hom* | 4.6 |
| 421977 | W94197 | Hs.110165 | ribosomal protein L26 homolog | 4.6 |
| 429441 | AJ224172 | Hs.204096 | lipophilin B (uteroglobin family member), pro | 4.6 |
| 449722 | BE280074 | Hs.23960 | cyclin B1 | 4.6 |
| 431689 | AA305688 | Hs.267695 | UDP-Gal: betaGlcNAc beta 1,3-galactosyltransfe | 4.5 |
| 425178 | H16097 | Hs.161027 | ESTs | 4.5 |
| 429597 | NM_003816 | Hs.2442 | a disintegrin and metalloproteinase domain 9 | 4.5 |
| 436556 | AI364997 | Hs.7572 | ESTs | 4.5 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 400534 | | | 0 | 4.5 |
| 417845 | AL117461 | Hs.82719 | *Homo sapiens* mRNA; cDNA DKFZp586F1822 (from c | 4.5 |
| 423123 | NM_012247 | Hs.124027 | SELENOPHOSPHATE SYNTHETASE; Human selenium d | 4.5 |
| 448305 | AA625207 | Hs.264915 | *Homo sapiens* cDNA FLJ12908 fis, clone NT2RP20 | 4.5 |
| 441006 | AW605267 | Hs.7627 | CGI-60 protein | 4.5 |
| 414569 | AF109298 | Hs.118258 | Prostate cancer associated protein 1 | 4.5 |
| 447924 | AI817226 | Hs.170337 | ESTs | 4.5 |
| 425506 | NM_003666 | Hs.158205 | basic leucine zipper nuclear factor 1 (JEM-1) | 4.5 |
| 411630 | U42349 | Hs.71119 | Putative prostate cancer tumor suppressor | 4.4 |
| 432842 | AW674093 | Hs.279525 | hypothetical protein PRO2605 | 4.4 |
| 413472 | BE242870 | Hs.75379 | solute carrier family 1 (glial high affinity | 4.4 |
| 414699 | AI815523 | Hs.76930 | synuclein, alpha (non A4 component of amyloid | 4.4 |
| 412733 | AA984472 | Hs.74554 | KIAA0080 protein | 4.4 |
| 419790 | U79250 | Hs.93201 | glycerol-3-phosphate dehydrogenase 2 (mitocho | 4.4 |
| 433377 | AI752713 | Hs.43845 | ESTs | 4.4 |
| 449535 | W15267 | Hs.23672 | low density lipoprotein receptor-related prot | 4.4 |
| 453900 | AW003582 | Hs.226414 | ESTs, Weakly similar to ALU8_HUMAN ALU SUBFAM | 4.4 |
| 443881 | R64512 | Hs.237146 | *Homo sapiens* cDNA FLJ14234 fis, clone NT2RP40 | 4.4 |
| 423025 | AA831267 | Hs.12244 | *Homo sapiens* cDNA: FLJ23581 fis, clone LNG136 | 4.4 |
| 408621 | AI970672 | Hs.46638 | chromosome 11 open reading frame 8; fetal br | 4.3 |
| 416241 | N52639 | Hs.32683 | ESTs | 4.3 |
| 432005 | AA524190 | Hs.120777 | ESTs, Weakly similar to ELL2_HUMAN RNA POLYME | 4.3 |
| 435532 | AW291488 | Hs.117305 | ESTs | 4.3 |
| 451813 | NM_016117 | Hs.27182 | phospholipase A2-activating protein | 4.3 |
| 454193 | BE141183 | | gb: MR0-HT0071-191199-001-b04 HT0071 *Homo sapi* | 4.3 |
| 418478 | U38945 | Hs.1174 | cyclin-dependent kinase inhibitor 2A (melanom | 4.3 |
| 406069 | | | 0 | 4.3 |
| 419465 | AW500239 | Hs.21187 | *Homo sapiens* cDNA: FLJ23068 fis, clone LNG055 | 4.3 |
| 418413 | R95735 | Hs.117753 | ESTs, Weakly similar to antigen of the monocl | 4.3 |
| 452028 | AK001859 | Hs.27595 | hypothetical protein FLJ10997 | 4.3 |
| 418693 | AI750878 | Hs.87409 | thrombospondin 1 | 4.3 |
| 410361 | BE391804 | Hs.62661 | guanylate binding protein 1, interferon-induc | 4.2 |
| 409763 | AL043212 | | gb: DKFZp434H0623_r1 434 (synonym: htes3) *Homo* | 4.2 |
| 455601 | AI368680 | Hs.816 | SRY (sex determining region Y)-box 2, partial | 4.2 |
| 408908 | BE296227 | Hs.48915 | serine/threonine kinase 15 | 4.2 |
| 413582 | AW295647 | Hs.71331 | *Homo sapiens* cDNA: FLJ21971 fis, clone HEP057 | 4.2 |
| 423248 | AA380177 | Hs.125845 | ribulose-5-phosphate-3-epimerase | 4.2 |
| 425024 | R39235 | Hs.12407 | ESTs | 4.2 |
| 447153 | AA805202 | Hs.173912 | eukaryotic translation initiation factor 4A, | 4.2 |
| 447406 | BE618060 | Hs.282882 | ESTs | 4.2 |
| 449347 | AV649748 | Hs.295901 | ESTs | 4.2 |
| 414279 | AW021691 | Hs.3804 | DKFZP564C1940 protein | 4.2 |
| 428856 | AA436735 | Hs.183171 | *Homo sapiens* cDNA: FLJ22002 fis, clone HEP066 | 4.2 |
| 407872 | AB039723 | Hs.40735 | frizzled (*Drosophila*) homolog 3 | 4.2 |
| 421502 | AF111856 | Hs.105039 | solute carrier family 34 (sodium phosphate), | 4.2 |
| 436406 | AW105723 | Hs.125346 | ESTs | 4.2 |
| 438209 | AL120659 | Hs.6111 | KIAA0307 gene product | 4.2 |
| 443653 | AA137043 | Hs.9663 | programmed cell death 6-interacting protein | 4.1 |
| 454556 | AW807073 | | gb: MR4-ST0062-031199-018-d06 ST0062 *Homo sapi* | 4.1 |
| 424834 | AK001432 | Hs.153408 | *Homo sapiens* cDNA FLJ10570 fis, clone NT2RP20 | 4.1 |
| 412593 | Y07558 | Hs.74088 | early growth response 3 | 4.1 |
| 416566 | NM_003914 | Hs.79378 | cyclin A1 | 4.1 |
| 426342 | AF093419 | Hs.169378 | multiple PDZ domain protein | 4.1 |
| 428417 | AK001699 | Hs.184227 | F-box only protein 21 | 4.1 |
| 429317 | AA831552 | Hs.268016 | solute carrier family 5 (inositol transporter | 4.1 |
| 446880 | AI811807 | Hs.108646 | *Homo sapiens* cDNA FLJ12534 fis, clone NT2RM40 | 4.1 |
| 422988 | AW673847 | Hs.97321 | ESTs | 4.0 |
| 434657 | AA641876 | Hs.191840 | ESTs | 4.0 |
| 412494 | AL133900 | Hs.792 | ADP-ribosylation factor domain protein 1, 64k | 4.0 |
| 443271 | BE568568 | Hs.195704 | ESTs | 4.0 |
| 421437 | AW821252 | Hs.104336 | ESTs | 4.0 |
| 401644 | | | 0 | 4.0 |
| 405095 | | | 0 | 4.0 |
| 418417 | R77182 | | gb: yi65e02.r1 Soares placenta Nb2HP *Homo sapi* | 4.0 |
| 420807 | AA280627 | Hs.57846 | ESTs | 4.0 |
| 429529 | AA454190 | Hs.193811 | ESTs, Moderately similar to reduced expressio | 4.0 |
| 457726 | AI217477 | Hs.194591 | ESTs | 4.0 |
| 431130 | NM_006103 | Hs.2719 | epididymis-specific; whey-acidic protein type | 4.0 |
| 453403 | BE466639 | Hs.61779 | *Homo sapiens* cDNA FLJ13591 fis, clone PLACE10 | 4.0 |
| 442768 | AL048534 | Hs.48458 | ESTs, Weakly similar to ALU8_HUMAN ALU SUBFAM | 4.0 |
| 413430 | R22479 | Hs.24650 | *Homo sapiens* cDNA FLJ13047 fis, clone NT2RP30 | 4.0 |
| 424081 | NM_006413 | Hs.139120 | ribonuclease P (30 kD) | 4.0 |
| 425692 | D90041 | Hs.155956 | NAT1; arylamine N-acetyltransferase | 4.0 |
| 407792 | AI077715 | Hs.39384 | putative secreted ligand homologous to fjx1 | 4.0 |
| 408353 | BE439838 | Hs.44298 | hypothetical protein | 4.0 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 421175 | AI879099 | Hs.102397 | GIOT-3 for gonadotropin inducible transcripti | 3.9 |
| 420324 | AF163474 | Hs.96744 | DKFZP586D0823 protein, Prostate androgen-regu | 3.9 |
| 417531 | NM_003157 | Hs.1087 | serine/threonine kinase 2 | 3.9 |
| 458924 | BE242158 | Hs.24427 | DKFZP566O1646 protein | 3.9 |
| 400195 | | | 0 | 3.9 |
| 401480 | | | 0 | 3.9 |
| 410360 | AW663690 | | gb: hj21g03.x1 NCI_CGAP_Li8 Homo sapiens cDNA | 3.9 |
| 410908 | AA121686 | Hs.10592 | ESTs | 3.9 |
| 420159 | AI572490 | Hs.99785 | ESTs | 3.9 |
| 422805 | AA436989 | Hs.121017 | H2A histone family; member A | 3.9 |
| 424639 | AI917494 | Hs.131329 | ESTs | 3.9 |
| 428555 | NM_002214 | Hs.184908 | integrin, beta 8 | 3.9 |
| 431699 | NM_001173 | Hs.267831 | Homo sapiens cDNA FLJ12952 fis, clone NT2RP20 | 3.9 |
| 433703 | AA210863 | Hs.3532 | nemo-like kinase | 3.9 |
| 437144 | AL049466 | Hs.7859 | ESTs | 3.9 |
| 452728 | AI915676 | Hs.239708 | ESTs | 3.9 |
| 430447 | W17064 | Hs.241451 | SWI/SNF related, matrix associated, actin dep | 3.9 |
| 440594 | AW445167 | Hs.126036 | ESTs | 3.9 |
| 408938 | AA059013 | Hs.22607 | ESTs | 3.9 |
| 427051 | BE178110 | Hs.173374 | ESTs | 3.9 |
| 447568 | AF155655 | Hs.18885 | CGI-116 protein | 3.9 |
| 457211 | AW972565 | Hs.32399 | ESTs, Weakly similar to Similar to Ena-VASP I | 3.9 |
| 443475 | AI066470 | Hs.134482 | ESTs | 3.9 |
| 433447 | U29195 | Hs.3281 | neuronal pentraxin II | 3.9 |
| 428093 | AW594506 | Hs.104830 | ESTs | 3.8 |
| 437938 | AI950087 | | ESTs; Weakly similar to Gag-Pol polyprotein [ | 3.8 |
| 408829 | NM_006042 | Hs.48384 | heparan sulfate (glucosamine) 3-O-sulfotransf | 3.8 |
| 429250 | H56585 | Hs.198308 | tryptophan rich basic protein | 3.8 |
| 441859 | AW194364 | Hs.128022 | ESTs, Weakly similar to FIG. 1 MOUSE FIG-1 PROT | 3.8 |
| 437700 | AA766060 | Hs.122848 | ESTs | 3.8 |
| 439560 | BE565647 | Hs.74899 | hypothetical protein FLJ12820 | 3.8 |
| 409564 | AA045857 | Hs.54943 | fracture callus 1 (rat) homolog | 3.8 |
| 429474 | AA453441 | Hs.31511 | ESTs | 3.8 |
| 431965 | BE175190 | | gb: QV2-HT0577-010500-165-g04 HT0577 Homo sapi | 3.8 |
| 454018 | AW016892 | Hs.241652 | ESTs | 3.8 |
| 426320 | W47595 | Hs.169300 | transforming growth factor, beta 2 | 3.8 |
| 439635 | AA477288 | Hs.94891 | Homo sapiens cDNA: FLJ22729 fis, clone HSI156 | 3.8 |
| 417517 | AF001176 | Hs.82238 | POP4 (processing of precursor, S. cerevisiae | 3.8 |
| 446402 | AI681145 | Hs.160724 | ESTs | 3.8 |
| 450236 | AW162998 | Hs.24684 | KIAA1376 protein | 3.8 |
| 410804 | U64820 | Hs.66521 | Machado-Joseph disease (spinocerebellar ataxi | 3.8 |
| 400268 | | | 0 | 3.8 |
| 418217 | AI910647 | Hs.13442 | ESTs | 3.8 |
| 421928 | AF013758 | Hs.109643 | polyadenylate binding protein-interacting pro | 3.8 |
| 417300 | AI765227 | Hs.55610 | solute carrier family 30 (zinc transporter), | 3.8 |
| 414136 | AA812434 | Hs.178227 | ESTs | 3.8 |
| 453945 | NM_005171 | Hs.36908 | activating transcription factor 1 | 3.7 |
| 400240 | | | 0 | 3.7 |
| 407877 | AW016811 | Hs.234478 | Homo sapiens cDNA: FLJ22648 fis, clone HSI073 | 3.7 |
| 450581 | AF081513 | Hs.25195 | endometrial bleeding associated factor (left- | 3.7 |
| 418223 | NM_014733 | Hs.83790 | KIAA0305 gene product | 3.7 |
| 411704 | AI499220 | Hs.71573 | hypothetical protein FLJ10074 | 3.7 |
| 432712 | AB016247 | Hs.288031 | sterol-C5-desaturase (fungal ERG3, delta-5-de | 3.7 |
| 422809 | AK001379 | Hs.121028 | hypothetical protein FLJ10549 | 3.7 |
| 402820 | | | 0 | 3.7 |
| 408090 | BE173621 | Hs.292478 | ESTs | 3.7 |
| 416421 | AA134006 | Hs.79306 | eukaryotic translation initiation factor 4E | 3.7 |
| 418282 | AA215535 | Hs.98133 | ESTs | 3.7 |
| 418454 | AA315308 | | gb: EST187095 Colon carcinoma (HCC) cell line | 3.7 |
| 418668 | AW407987 | Hs.87150 | Human clone A9A2BR11 (CAC)n/(GTG)n repeat-con | 3.7 |
| 422290 | AA495854 | Hs.48827 | hypothetical protein FLJ12085 | 3.7 |
| 432824 | AK001783 | Hs.279012 | hypothetical protein FLJ10921 | 3.7 |
| 439907 | AA853978 | Hs.124577 | ESTs | 3.7 |
| 447479 | AB037834 | Hs.18685 | Homo sapiens mRNA for KIAA1413 protein, parti | 3.7 |
| 451073 | AI758905 | Hs.206063 | ESTs | 3.7 |
| 450377 | AB033091 | Hs.24936 | ESTs | 3.7 |
| 414343 | AL036166 | Hs.75914 | coated vesicle membrane protein | 3.7 |
| 448807 | AI571940 | Hs.7549 | ESTs | 3.7 |
| 442821 | BE391929 | Hs.8752 | Putative type II membrane protein | 3.7 |
| 426300 | U15979 | Hs.169228 | delta-like homolog (Drosophila) | 3.7 |
| 418068 | AW971155 | Hs.293902 | ESTs, Weakly similar to prolyl 4-hydroxylase | 3.7 |
| 411263 | BE297802 | Hs.69360 | kinesin-like 6 (mitotic centromere-associated | 3.7 |
| 443054 | AI745185 | Hs.8939 | yes-associated protein 65 kDa | 3.7 |
| 421154 | AA284333 | Hs.287631 | Homo sapiens cDNA FLJ14269 fis, clone PLACE10 | 3.7 |
| 411402 | BE297855 | Hs.69855 | NRAS-related gene | 3.7 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 450447 | AF212223 | Hs.25010 | hypothetical protein P15-2 | 3.6 |
| 414706 | AW340125 | Hs.76989 | KIAA0097 gene product | 3.6 |
| 434228 | Z42047 | Hs.283978 | ESTs; KIAA0738 gene product | 3.6 |
| 434164 | AW207019 | Hs.148135 | ESTs | 3.6 |
| 409533 | AW969543 | Hs.21291 | mitogen-activated protein kinase kinase kinas | 3.6 |
| 402222 | | | 0 | 3.6 |
| 404915 | | | 0 | 3.6 |
| 404996 | | | 0 | 3.6 |
| 411560 | AW851186 | | gb: IL3-CT0220-150200-071-H05 CT0220 *Homo sapi* | 3.6 |
| 419750 | AL079741 | Hs.183114 | *Homo sapiens* cDNA FLJ14236 fis, clone NT2RP40 | 3.6 |
| 426010 | AA136563 | Hs.1975 | *Homo sapiens* cDNA: FLJ21007 fis, clone CAE038 | 3.6 |
| 427038 | NM_014633 | Hs.173288 | KIAA0155 gene product | 3.6 |
| 439255 | BE164500 | | gb: RC4-HT0469-230300-014-e10 HT0469 *Homo sapi* | 3.6 |
| 458242 | BE299588 | Hs.28465 | *Homo sapiens* cDNA: FLJ21869 fis, clone HEP024 | 3.6 |
| 415115 | AA214228 | Hs.127751 | hypothetical protein | 3.6 |
| 453468 | W00712 | Hs.32990 | DKFZP566F084 protein | 3.6 |
| 441205 | AW137827 | Hs.176904 | ESTs | 3.6 |
| 452693 | T79153 | Hs.48589 | zinc finger protein 228 | 3.6 |
| 417389 | BE260964 | Hs.82045 | Midkine (neurite growth-promoting factor 2) | 3.6 |
| 448105 | AW591433 | Hs.170675 | ESTs, Weakly similar to TMS2_HUMAN TRANSMEMBR | 3.6 |
| 451522 | BE565817 | Hs.26498 | hypothetical protein FLJ21657 | 3.6 |
| 440048 | AA897461 | Hs.158469 | ESTs, Weakly similar to envelope protein [*H. s* | 3.5 |
| 419359 | AL043202 | Hs.90073 | chromosome segregation 1 (yeast homolog)-like | 3.5 |
| 452030 | AL137578 | Hs.27607 | *Homo sapiens* mRNA; cDNA DKFZp564N2464 (from c | 3.5 |
| 400666 | | | 0 | 3.5 |
| 422646 | H87863 | Hs.151380 | ESTs | 3.5 |
| 407846 | AA426202 | Hs.40403 | Cbp/p300-interacting transactivator, with Glu | 3.5 |
| 408730 | AV660717 | Hs.47144 | DKFZP586N0819 protein | 3.5 |
| 401517 | | | 0 | 3.5 |
| 413775 | AW409934 | Hs.75528 | nucleolar GTPase | 3.5 |
| 417177 | NM_004458 | Hs.81452 | fatty-acid-Coenzyme A ligase, long-chain 4 | 3.5 |
| 427943 | AW959075 | | gb: EST371145 MAGE resequences, MAGE *Homo sapi* | 3.5 |
| 439107 | AL046134 | Hs.27895 | ESTs | 3.5 |
| 447268 | AI370413 | Hs.36563 | *Homo sapiens* cDNA: FLJ22418 fis, clone HRC085 | 3.5 |
| 412604 | AW978324 | Hs.47144 | DKF7P586N0819 protein | 3.5 |
| 427134 | AA398409 | Hs.173561 | EST | 3.5 |
| 430273 | AI311127 | Hs.125522 | ESTs | 3.5 |
| 436671 | AW137159 | Hs.146151 | ESTs | 3.5 |
| 433037 | NM_014158 | Hs.279938 | HSPC067 protein | 3.5 |
| 453745 | AA952989 | Hs.63908 | *Homo sapiens* HSPC316 mRNA, partial cds | 3.5 |
| 400531 | AF151064 | Hs.36069 | hypothetical protein | 3.5 |
| 433345 | AI681545 | Hs.152982 | EST cluster (not in UniGene) | 3.4 |
| 406400 | AA343629 | Hs.104570 | kallikrein 8 (neuropsin/ovasin) | 3.4 |
| 407596 | R86913 | | gb: yq30f05.r1 Soares fetal liver spleen 1NFLS | 3.4 |
| 453779 | N35187 | Hs.43388 | ESTs | 3.4 |
| 444858 | AI199738 | Hs.208275 | ESTs, Weakly similar to unnamed protein produ | 3.4 |
| 447688 | N87079 | Hs.19236 | NADH dehydrogenase (ubiquinone) 1 beta subcom | 3.4 |
| 424856 | AA347746 | Hs.9521 | ESTs, Weakly similar to KIAA1015 protein [*H. s* | 3.4 |
| 407864 | AF069291 | Hs.40539 | chromosome 8 open reading frame 1 | 3.4 |
| 404108 | | | 0 | 3.4 |
| 403729 | | | 0 | 3.4 |
| 404232 | | | 0 | 3.4 |
| 423687 | AA329633 | Hs.133011 | ESTs, Highly similar to Z117_HUMAN ZINC FINGE | 3.4 |
| 428372 | AK000684 | Hs.183887 | hypothetical protein FLJ22104 | 3.4 |
| 439741 | BE379646 | Hs.6904 | *Homo sapiens* mRNA full length insert cDNA clo | 3.4 |
| 441447 | AA934077 | Hs.126980 | ESTs | 3.4 |
| 448358 | R44433 | Hs.106614 | Human DNA sequence from clone RP4-534K7 on ch | 3.4 |
| 450926 | AI744361 | Hs.205591 | ESTs, Weakly similar to zinc finger protein P | 3.4 |
| 458477 | NM_000314 | Hs.10712 | phosphatase and tensin homolog (mutated in mu | 3.4 |
| 421379 | Y15221 | Hs.103982 | small inducible cytokine subfamily B (Cys-X-C | 3.4 |
| 452822 | X85689 | Hs.288617 | *Homo sapiens* cDNA: FLJ22621 fis, clone HSI056 | 3.4 |
| 441111 | AI806867 | Hs.126594 | ESTs | 3.4 |
| 447519 | U46258 | Hs.23448 | ESTs | 3.4 |
| 446913 | AA430650 | Hs.16529 | transmembrane 4 superfamily member (tetraspan | 3.4 |
| 449581 | AI989517 | Hs.181605 | ESTs | 3.4 |
| 456132 | BE219771 | Hs.237146 | *Homo sapiens* cDNA FLJ14234 fis, clone NT2RP40 | 3.4 |
| 448186 | AA262105 | Hs.4094 | *Homo sapiens* cDNA FLJ14208 fis, clone NT2RP30 | 3.4 |
| 422611 | AA158177 | Hs.118722 | fucosyltransferase 8 (alpha (1,6) fucosyltran | 3.4 |
| 441433 | AA933809 | Hs.42746 | ESTs | 3.4 |
| 417837 | AL079905 | Hs.1103 | transforming growth factor, beta 1 | 3.4 |
| 450516 | AA902656 | Hs.21943 | NIF3 (Ngg1 interacting factor 3, *S. pombe* homo | 3.4 |
| 407796 | AA195509 | Hs.272239 | lymphocyte activation-associated protein | 3.3 |
| 419200 | AW966405 | Hs.288856 | prefoldin 5 | 3.3 |
| 423161 | AL049227 | Hs.124776 | *Homo sapiens* mRNA; cDNA DKFZp564N1116 (from c | 3.3 |
| 445679 | AI343868 | Hs.58800 | *Homo sapiens* cDNA FLJ12488 fis, clone NT2RM20 | 3.3 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 435014 | BE560898 | Hs.10026 | ribosomal protein L17 isolog | 3.3 |
| 446619 | AU076643 | Hs.313 | secreted phosphoprotein 1 (osteopontin, bone | 3.3 |
| 439170 | AA332365 | Hs.165539 | ESTs | 3.3 |
| 429830 | AI537278 | Hs.225841 | DKFZP434D193 protein | 3.3 |
| 428943 | AW086180 | Hs.37636 | ESTs, Weakly similar to KIAA1392 protein [*H. s* | 3.3 |
| 445817 | NM_003642 | Hs.13340 | histone acetyltransferase 1 | 3.3 |
| 408805 | H69912 | Hs.48269 | vaccinia related kinase 1 | 3.3 |
| 441134 | W29092 | Hs.7678 | cellular retinoic acid-binding protein 1 | 3.3 |
| 408532 | AI453137 | Hs.63176 | ESTs | 3.3 |
| 409517 | X90780 | Hs.54668 | troponin I, cardiac | 3.3 |
| 414304 | AI621276 | Hs.165998 | DKFZP564M2423 protein | 3.3 |
| 436427 | AI344378 | Hs.143399 | ESTs | 3.3 |
| 436662 | AI582393 | Hs.126695 | ESTs | 3.3 |
| 440304 | BE159984 | Hs.125395 | ESTs | 3.3 |
| 447385 | F12863 | | gb: HSC3FE081 normalized infant brain cDNA Hom | 3.3 |
| 451177 | AI969716 | Hs.13034 | ESTs | 3.3 |
| 428949 | AA442153 | Hs.104744 | ESTs, Weakly similar to AF208855 1 BM-013 [*H.* | 3.3 |
| 451743 | AW074266 | Hs.23071 | ESTs | 3.3 |
| 421515 | Y11339 | Hs.105352 | GalNAc alpha-2, 6-sialyltransferase I, long f | 3.3 |
| 446351 | AW444551 | Hs.258532 | ESTs | 3.3 |
| 435102 | AW899053 | Hs.76917 | F-box only protein 8 | 3.3 |
| 418216 | AA662240 | Hs.283099 | AF15q14 protein | 3.3 |
| 401508 | | | 0 | 3.3 |
| 437108 | AA434054 | Hs.80624 | *Homo sapiens* cDNA: FLJ23442 fis, clone HSI009 | 3.3 |
| 416530 | U62801 | Hs.79361 | kallikrein 6 (neurosin, zyme) | 3.3 |
| 443171 | BE281128 | Hs.9030 | TONDU | 3.3 |
| 458627 | AW088642 | Hs.97984 | ESTs; Weakly similar to WASP-family protein [ | 3.3 |
| 412078 | X69699 | Hs.73149 | paired box gene 8 | 3.3 |
| 414080 | AA135257 | Hs.47783 | ESTs, Weakly similar to T12540 hypothetical p | 3.3 |
| 401197 | | | 0 | 3.3 |
| 422134 | AW179019 | Hs.112110 | ESTs | 3.3 |
| 409044 | AI129586 | Hs.33033 | ESTs | 3.3 |
| 416198 | H27332 | Hs.99598 | ESTs | 3.2 |
| 436481 | AA379597 | Hs.5199 | HSPC150 protein similar to ubiquitin-conjugat | 3.2 |
| 436525 | AA721428 | Hs.26145 | *Homo sapiens* cDNA FLJ14127 fis, clone MAMMA10 | 3.2 |
| 409142 | AL136877 | Hs.50758 | chromosome-associated polypeptide C | 3.2 |
| 428819 | AL135623 | Hs.193914 | KIAA0575 gene product | 3.2 |
| 428728 | NM_016625 | Hs.191381 | ESTs; Weakly similar to hypothetical protein | 3.2 |
| 421261 | AA600853 | Hs.98133 | ESTs | 3.2 |
| 446219 | AI287344 | Hs.149827 | ESTs | 3.2 |
| 457574 | H88717 | Hs.27774 | ESTs, Highly similar to AF161349 1 HSPC086 [H | 3.2 |
| 409172 | Z99399 | Hs.118145 | ESTs | 3.2 |
| 419388 | T67012 | Hs.75323 | prohibitin | 3.2 |
| 434187 | AA627098 | Hs.99103 | ESTs, Weakly similar to I38428 T-complex prot | 3.2 |
| 445060 | AA830811 | Hs.88808 | ESTs | 3.2 |
| 448254 | AI829900 | Hs.22929 | ESTs | 3.2 |
| 452943 | BE247449 | Hs.31082 | hypothetical protein FLJ10525 | 3.2 |
| 411393 | AW797437 | Hs.69771 | B-factor, properdin | 3.2 |
| 453775 | NM_002916 | Hs.35120 | replication factor C (activator 1) 4 (37 kD) | 3.2 |
| 408418 | AW963897 | Hs.44743 | KIAA1435 protein | 3.2 |
| 442025 | AW887434 | Hs.11810 | ESTs, Weakly similar to CD4.2 [*C. elegans*] | 3.2 |
| 417006 | AW673606 | Hs.80758 | aspartyl-tRNA synthetase | 3.2 |
| 407881 | AW072003 | Hs.40968 | heparan sulfate (glucosamine) 3-O-sulfotransf | 3.2 |
| 444755 | AA431791 | Hs.183001 | ESTs | 3.2 |
| 402829 | | | 0 | 3.2 |
| 451593 | AF151879 | Hs.26706 | CGI-121 protein | 3.2 |
| 419926 | AW900992 | Hs.93796 | DKFZP586D2223 protein | 3.2 |
| 434551 | BE387162 | Hs.280858 | ESTs, Highly similar to XPB_HUMAN DNA-REPAIR | 3.2 |
| 445929 | AI089660 | Hs.7838 | makorin, ring finger protein, 1 | 3.2 |
| 409365 | AA702376 | Hs.226440 | *Homo sapiens* clone 24881 mRNA sequence | 3.2 |
| 418836 | AI655499 | Hs.161712 | ESTs | 3.2 |
| 441020 | W79283 | Hs.35962 | ESTs | 3.1 |
| 422363 | T55979 | Hs.115474 | replication factor C (activator 1) 3 (38 kD) | 3.1 |
| 413010 | AA393273 | Hs.75133 | transcription factor 6-like 1 (mitochondrial | 3.1 |
| 452092 | BE245374 | Hs.27842 | hypothetical protein FLJ11210 | 3.1 |
| 410486 | AW235094 | Hs.193424 | ESTs, Weakly similar to KIAA1064 protein [*H. s* | 3.1 |
| 434540 | NM_016045 | Hs.5184 | TH1 *drosophila* homolog | 3.1 |
| 409178 | BE393948 | Hs.50915 | kallikrein 5 | 3.1 |
| 439480 | AL038511 | Hs.125316 | ESTs | 3.1 |
| 417848 | AA206581 | Hs.39457 | ESTs | 3.1 |
| 446293 | AI420213 | Hs.149722 | ESTs | 3.1 |
| 408108 | AI580492 | Hs.42743 | hypothetical protein | 3.1 |
| 415947 | U04045 | Hs.78934 | mutS (*E. coli*) homolog 2 (colon cancer, nonpo | 3.1 |
| 410519 | AW612264 | Hs.131705 | ESTs | 3.1 |
| 421987 | AI133161 | Hs.286131 | CGI-101 protein | 3.1 |

TABLE 10A-continued

ABOUT 733 UP-REGULATED GENES, OVARIAN CANCER VERSUS NORMAL ADULT TISSUES

| Pkey | Ex. Accn | UG ID | Title | ratio |
|---|---|---|---|---|
| 440046 | AW402306 | Hs.6877 | hypothetical protein FLJ10483 | 3.1 |
| 453931 | AL121278 | Hs.25144 | ESTs | 3.1 |
| 454423 | AW603985 | Hs.179662 | nucleosome assembly protein 1-like 1 | 3.1 |
| 459089 | F13036 | Hs.27373 | *Homo sapiens* mRNA; cDNA DKFZp564O1763 (from c | 3.1 |
| 418735 | N48769 | Hs.44609 | ESTs | 3.1 |
| 414245 | BE148072 | Hs.75850 | WAS protein family, member 1 | 3.1 |
| 410909 | AW898161 | Hs.53112 | ESTs, Weakly similar to ALU8_HUMAN ALU SUBFAM | 3.1 |
| 434926 | BE543269 | Hs.50252 | *Homo sapiens* HSPC283 mRNA, partial cds | 3.1 |
| 409239 | AA740875 | Hs.44307 | ESTs | 3.1 |
| 429017 | AA463605 | Hs.238995 | ESTs | 3.1 |
| 447072 | D61594 | Hs.17279 | tyrosylprotein sulfotransferase 1 | 3.1 |
| 426514 | BE616633 | Hs.301122 | bone morphogenetic protein 7 (osteogenic prot | 3.1 |
| 448133 | AA723157 | Hs.73769 | folate receptor 1 (adult) | 3.1 |
| 418792 | AB037805 | Hs.88442 | KIAA1384 protein | 3.1 |
| 427528 | AU077143 | Hs.179565 | minichromosome maintenance deficient (*S. cere* | 3.1 |
| 402077 | | | 0 | 3.1 |
| 440671 | AW297920 | Hs.130054 | ESTs | 3.1 |
| 419890 | X17360 | Hs.278255 | homeo box D4 | 3.1 |
| 406687 | M31126 | Hs.272620 | pregnancy specific beta-1-glycoprotein 9 | 3.1 |
| 409151 | AA306105 | Hs.50785 | SEC22, vesicle trafficking protein (*S. cerevi* | 3.1 |
| 431221 | AA449015 | Hs.286145 | SRB7 (suppressor of RNA polymerase B; yeast) | 3.1 |
| 443584 | AI807036 | Hs.101619 | ESTs | 3.1 |
| 445525 | BE149866 | Hs.14831 | ESTs | 3.1 |
| 410441 | BE298210 | | gb: 601118016F1 NIH_MGC_17 *Homo sapiens* cDNA c | 3.1 |
| 422634 | NM_016010 | Hs.118821 | CGI-62 protein | 3.0 |
| 420022 | AA256253 | Hs.120817 | ESTs | 3.0 |
| 453912 | AL121031 | Hs.32556 | KIAA0379 protein | 3.0 |
| 456844 | AI264155 | Hs.152981 | CDP-diacylglycerol synthase (phosphatidate cy | 3.0 |
| 414941 | C14865 | Hs.182159 | ESTs | 3.0 |
| 407807 | AL031427 | Hs.40094 | Human DNA sequence from clone 167A19 on chrom | 3.0 |
| 414725 | AA769791 | Hs.120355 | *Homo sapiens* cDNA FLJ13148 fis, clone NT2RP30 | 3.0 |
| 444420 | AI148157 | Hs.146766 | ESTs | 3.0 |
| 431742 | NM_016652 | Hs.268281 | CGI-201 protein | 3.0 |
| 412519 | AA196241 | Hs.73980 | troponin T1, skeletal, slow | 3.0 |
| 418348 | AI537167 | Hs.96322 | *Homo sapiens* cDNA: FLJ23560 fis, clone LNG098 | 3.0 |
| 444261 | AA298958 | Hs.10724 | MDS023 protein | 3.0 |
| 457465 | AW301344 | Hs.195969 | ESTs | 3.0 |
| 443933 | AI091631 | Hs.135501 | *Homo sapiens* two pore potassium channel KT3.3 | 3.0 |
| 442150 | AI368158 | Hs.128864 | ESTs | 3.0 |
| 414883 | AA926960 | Hs.77550 | CDC28 protein kinase 1 | 3.0 |
| 442879 | AF032922 | Hs.8813 | syntaxin binding protein 3 | 3.0 |
| 437949 | U78519 | Hs.41654 | ESTs | 3.0 |
| 403515 | | | 0 | 3.0 |
| 403864 | | | 0 | 3.0 |
| 407785 | AW207285 | Hs.98279 | ESTs | 3.0 |
| 426199 | AA371865 | Hs.97090 | ESTs | 3.0 |
| 426324 | AW291787 | Hs.200933 | ESTs | 3.0 |
| 427738 | NM_000318 | Hs.180612 | peroxisomal membrane protein 3 (35 kD, Zellweg | 3.0 |
| 427837 | U87309 | Hs.180941 | vacuolar protein sorting 41 (yeast homolog) | 3.0 |
| 439450 | AF124250 | Hs.6564 | breast cancer anti-estrogen resistance 1 | 3.0 |
| 442039 | AW276240 | Hs.128352 | ESTs, Weakly similar to p80 [*R. norvegicus*] | 3.0 |
| 446978 | NM_001938 | Hs.16697 | down-regulator of transcription 1, TBP-bindin | 3.0 |
| 452431 | U88879 | Hs.29499 | toll-like receptor 3 | 3.0 |
| 452841 | T17431 | Hs.65412 | DEAD/H (Asp-Glu-Ala-Asp/His) box polypeptide | 3.0 |
| 432114 | AL036021 | Hs.225597 | ESTs | 3.0 |
| 445640 | AW969626 | Hs.31704 | ESTs, Weakly similar to KIAA0227 [*H. sapiens*] | 3.0 |
| 442607 | AA507576 | Hs.288361 | KIAA0741 gene product | 3.0 |
| 453920 | AI133148 | Hs.36602 | I factor (complement) | 3.0 |
| 430000 | AW205931 | Hs.99598 | ESTs | 3.0 |
| 429164 | AI688663 | Hs.116586 | ESTs | 3.0 |
| 453331 | AI240665 | Hs.8895 | ESTs | 3.0 |
| 448663 | BE614599 | Hs.106823 | *H. sapiens* gene from PAC 426I6, similar to syn | 3.0 |
| 425776 | U25128 | Hs.159499 | parathyroid hormone receptor 2 | 3.0 |
| 401714 | | | 0 | 3.0 |
| 400903 | | | 0 | 3.0 |
| 428428 | AL037544 | Hs.184298 | cyclin-dependent kinase 7 (homolog of *Xenopus* | 3.0 |
| 443761 | AI525743 | Hs.160603 | ESTs | 3.0 |
| 451640 | AA195601 | Hs.26771 | Human DNA sequence from clone 747H23 on chrom | 3.0 |
| 442580 | AI733682 | Hs.130239 | ESTs | 3.0 |

Pkey: Primekey
Ex. Accn: Exemplar Accession
UG ID: UniGene ID
Title: UniGene title
ratio: ratio tumor vs normal tissues Table 13A lists about 1086 genes up-regulated in ovarian cancer compared to normal ovaries. These were selected as for Table 10A, except that the ratio was greater than or equal to 10, and the denominator was the median value for various non-malignant ovary specimens.

TABLE 13A

About 1086 UP-REGULATED GENES, OVARIAN CANCER VERSUS NORMAL OVARY

| Pkey | Ex. Accn | UG ID | Title | ratio |
|---|---|---|---|---|
| 439706 | AW872527 | Hs.59761 | ESTs | 109.2 |
| 446619 | AU076643 | Hs.313 | secreted phosphoprotein 1 (osteopontin, bone | 107.8 |
| 422095 | AI868872 | Hs.288966 | ceruloplasmin (ferroxidase) | 104.4 |
| 447111 | AI017574 | Hs.17409 | cysteine-rich protein 1 (intestinal) | 88.3 |
| 431130 | NM_006103 | Hs.2719 | epididymis-specific; whey-acidic protein type | 82.8 |
| 431369 | BE184455 | Hs.251754 | secretory leukocyte protease inhibitor (antil | 81.9 |
| 413859 | AW992356 | Hs.8364 | ESTs | 73.9 |
| 446291 | BE397753 | Hs.14623 | interferon, gamma-inducible protein 30 | 72.7 |
| 426050 | AF017307 | Hs.166096 | E74-like factor 3 (ets domain transcription f | 68.1 |
| 411469 | T09997 | Hs.70327 | cysteine-rich protein 2 | 66.6 |
| 429504 | X99133 | Hs.204238 | lipocalin 2 (oncogene 24p3) | 65.7 |
| 416971 | R34657 | Hs.80658 | uncoupling protein 2 (mitochondrial, proton c | 64.9 |
| 450273 | AW296454 | Hs.24743 | hypothetical protein FLJ20171 | 62.5 |
| 446441 | AK001782 | Hs.15093 | hypothetical protein | 60.7 |
| 428758 | AA433988 | Hs.98502 | *Homo sapiens* cDNA FLJ14303 fis, clone PLACE20 | 59.7 |
| 441406 | Z45957 | Hs.7837 | *Homo sapiens* cDNA FLJ10457 fis, clone NT2RP10 | 57.8 |
| 441859 | AW194364 | Hs.128022 | ESTs, Weakly similar to FIG. 1 MOUSE FIG-1 PROT | 56.7 |
| 448406 | AW772298 | Hs.21103 | *Homo sapiens* mRNA; cDNA DKFZp564B076 | 55.7 |
| 414602 | AW630088 | Hs.76550 | *Homo sapiens* mRNA; cDNA DKFZp564B1264 | 55.2 |
| 418068 | AW971155 | Hs.293902 | ESTs, Weakly similar to prolyl 4-hydroxylase | 54.8 |
| 428330 | L22524 | Hs.2256 | matrix metalloproteinase 7 (matrilysin, uteri | 53.4 |
| 412636 | NM_004415 | Hs.74316 | desmoplakin (DPI, DPII) | 51.4 |
| 430634 | AI860651 | Hs.26685 | ESTs | 50.7 |
| 439318 | AW837046 | Hs.6527 | G protein-coupled receptor 56 | 50.7 |
| 417259 | AW903838 | Hs.81800 | chondroitin sulfate proteoglycan 2 (versican) | 50.6 |
| 407786 | AA687538 | Hs.38972 | tetraspan 1 | 50.4 |
| 426836 | N41720 | Hs.172684 | vesicle-associated membrane protein 8 (endobr | 49.7 |
| 417308 | H60720 | Hs.81892 | KIAA0101 gene product | 48.9 |
| 436876 | AI124756 | Hs.5337 | isocitrate dehydrogenase 2 (NADP+), mitochond | 48.4 |
| 439180 | AI393742 | Hs.199067 | v-erb-b2 avian erythroblastic leukemia viral | 47.1 |
| 428289 | M26301 | Hs.2253 | complement component 2 | 46.3 |
| 405484 | | | 0 | 46.1 |
| 425371 | D49441 | Hs.155981 | mesothelin | 45.7 |
| 403912 | | | 0 | 45.0 |
| 443021 | AA368546 | Hs.8904 | Ig superfamily protein | 44.6 |
| 427697 | T18997 | Hs.180372 | BCL2-like 1 | 44.3 |
| 428227 | AA321649 | Hs.2248 | INTERFERON-GAMMA INDUCED PROTEIN | 44.0 |
| 404678 | | | 0 | 43.9 |
| 400289 | X07820 | Hs.2258 | Matrix Metalloproteinase 10 (Stromolysin 2) | 43.8 |
| 451035 | AU076785 | Hs.430 | plastin 1 (I isoform) | 43.8 |
| 440848 | BE314650 | Hs.7476 | ATPase, H+ transporting, lysosomal (vacuolar | 42.8 |
| 436278 | BE396290 | Hs.5097 | synaptogyrin 2 | 42.4 |
| 413936 | AF113676 | Hs.75621 | serine (or cysteine) proteinase inhibitor, cl | 42.1 |
| 420859 | AW468397 | Hs.100000 | S100 calcium-binding protein A8 (calgranulin | 42.1 |
| 428411 | AW291464 | Hs.10338 | ESTs | 41.8 |
| 422166 | W72424 | Hs.112405 | S100 calcium-binding protein A9 (calgranulin | 41.5 |
| 412477 | AA150864 | Hs.790 | microsomal glutathione S-transferase 1 | 40.7 |
| 417130 | AW276858 | Hs.81256 | S100 calcium-binding protein A4 (calcium prot | 40.1 |
| 424673 | AA345051 | Hs.294092 | ESTs | 39.8 |
| 416530 | U62801 | Hs.79361 | kallikrein 6 (neurosin, zyme) | 39.7 |
| 443162 | T49951 | Hs.9029 | ESTs; Highly similar to KERATIN; TYPE I CYTO | 39.5 |
| 413719 | BE439580 | Hs.75498 | small inducible cytokine subfamily A (Cys—Cys | 39.3 |
| 424687 | J05070 | Hs.151738 | matrix metalloproteinase 9 (gelatinase B, 92k | 38.9 |
| 413063 | AL035737 | Hs.75184 | chitinase 3-like 1 (cartilage glycoprotein-39 | 38.5 |
| 429441 | AJ224172 | Hs.204096 | lipophilin B (uteroglobin family member), pro | 38.1 |
| 418526 | BE019020 | Hs.85838 | solute carrier family 16 (monocarboxylic acid | 37.9 |
| 415511 | AI732617 | Hs.182362 | ESTs | 37.7 |
| 409453 | AI885516 | Hs.95612 | ESTs | 37.7 |
| 445537 | AJ245671 | Hs.12844 | EGF-like-domain; multiple 6 | 37.3 |
| 442432 | BE093589 | Hs.38178 | *Homo sapiens* cDNA: FLJ23468 fis, clone HSI116 | 37.3 |
| 408243 | Y00787 | Hs.624 | interleukin 8 | 37.3 |
| 419092 | J05581 | Hs.89603 | mucin 1, transmembrane | 36.7 |
| 444172 | BE147740 | Hs.104558 | ESTs | 36.0 |
| 412115 | AK001763 | Hs.73239 | hypothetical protein FLJ10901 | 35.8 |
| 420440 | NM_002407 | Hs.97644 | mammaglobin 2 | 35.7 |
| 414386 | X00442 | Hs.75990 | haptoglobin | 35.3 |
| 423225 | AA852604 | Hs.125359 | Thy-1 cell surface antigen | 35.1 |
| 440596 | H13032 | Hs.103378 | ESTs, Weakly similar to DRR1 [*H. sapiens*] | 35.0 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 413278 | BE563085 | Hs.833 | interferon-stimulated protein, 15 kDa | 34.9 |
| 418506 | AA084248 | Hs.85339 | G protein-coupled receptor 39 | 34.8 |
| 445919 | T53519 | Hs.290357 | ESTs | 34.7 |
| 416854 | H40164 | Hs.80296 | Purkinje cell protein 4 | 34.4 |
| 414186 | U33446 | Hs.75799 | protease, serine, 8 (prostasin) | 34.2 |
| 434371 | AA631362 | | gb: np86b01.s1 NCI_CGAP_Thy1 Homo sapiens cDNA | 33.9 |
| 421937 | AI878857 | Hs.109706 | HN1 protein | 33.9 |
| 449722 | BE280074 | Hs.23960 | cyclin B1 | 33.8 |
| 400965 | | | 0 | 33.7 |
| 452203 | X57522 | Hs.158164 | ATP-binding cassette, sub-family B (MDR/TAP), | 33.5 |
| 411945 | AL033527 | Hs.92137 | v-myc avian myelocytomatosis viral oncogene h | 33.5 |
| 425811 | AL039104 | Hs.159557 | karyopherin alpha 2 (RAG cohort 1, importin a | 33.4 |
| 408901 | AK001330 | Hs.48855 | hypothetical protein FLJ10468 | 33.3 |
| 438461 | AW075485 | Hs.286049 | phosphoserine aminotransferase | 33.3 |
| 422963 | M79141 | Hs.13234 | ESTs | 33.3 |
| 426158 | NM_001982 | Hs.199067 | v-erb-b2 avian erythroblastic leukemia viral | 33.2 |
| 431836 | AF178532 | Hs.271411 | beta-site APP-cleaving enzyme 2 | 32.8 |
| 421502 | AF111856 | Hs.105039 | solute carrier family 34 (sodium phosphate), | 32.5 |
| 431211 | M86849 | Hs.5566 | Homo sapiens connexin 26 (GJB2) mRNA, complet | 32.5 |
| 436552 | NM_014038 | Hs.5216 | HSPC028 protein | 32.5 |
| 442533 | AA161224 | Hs.8372 | ubiquinol-cytochrome c reductase (6.4 kD) subu | 32.5 |
| 406400 | AA343629 | Hs.104570 | kallikrein 8 (neuropsin/ovasin) | 32.4 |
| 450353 | AI244661 | Hs.103296 | ESTs | 32.4 |
| 422158 | L10343 | Hs.112341 | protease inhibitor 3, skin-derived (SKALP) | 32.4 |
| 433412 | AV653729 | Hs.8185 | CGI-44 protein; sulfide dehydrogenase like (y | 32.3 |
| 441020 | W79283 | Hs.35962 | ESTs | 32.2 |
| 432201 | AI538613 | Hs.135657 | TMPRSS3a mRNA for serine protease (ECHOS1) (T | 32.0 |
| 424125 | M31669 | Hs.1735 | inhibin, beta B (activin AB beta polypeptide) | 31.9 |
| 453309 | AI791809 | Hs.32949 | defensin, beta 1 | 31.8 |
| 408380 | AF123050 | Hs.44532 | diubiquitin | 31.7 |
| 419329 | AY007220 | Hs.288998 | S100-type calcium binding protein A14 | 31.6 |
| 409231 | AA446644 | Hs.692 | GA733-2; epithelial glycoprotein (EGP) (KSA) | 31.6 |
| 423961 | D13666 | Hs.136348 | Homo sapiens mRNA for osteoblast specific fac | 31.2 |
| 413840 | AI301558 | Hs.290801 | ESTs | 30.8 |
| 440943 | AW082298 | Hs.146161 | ESTs, Weakly similar to KIAA0859 protein [H. s | 30.8 |
| 419239 | AA468183 | Hs.184598 | Homo sapiens cDNA: FLJ23241 fis, clone COL013 | 30.4 |
| 410132 | NM_003480 | Hs.58882 | Microfibril-associated glycoprotein-2 | 30.2 |
| 418203 | X54942 | Hs.83758 | CDC28 protein kinase 2 | 30.1 |
| 412719 | AW016610 | Hs.129911 | ESTs | 30.0 |
| 407862 | BE548267 | Hs.50724 | Homo sapiens cDNA FLJ10934 fis, clone OVARC10 | 30.0 |
| 431563 | AI027643 | Hs.120912 | ESTs | 29.9 |
| 431743 | AW972642 | Hs.293055 | ESTs | 29.8 |
| 443295 | AI049783 | Hs.241284 | ESTs | 29.7 |
| 413745 | AW247252 | Hs.75514 | nucleoside phosphorylase | 29.7 |
| 441028 | AI333660 | Hs.17558 | ESTs | 29.6 |
| 442315 | AA173992 | Hs.7956 | ESTs | 29.6 |
| 452838 | U65011 | Hs.30743 | Preferentially expressed antigen in melanoma | 29.5 |
| 428479 | Y00272 | Hs.184572 | cell division cycle 2, G1 to S and G2 to M | 29.5 |
| 432280 | BE440142 | Hs.2943 | signal recognition particle 19 kD | 29.4 |
| 420158 | AI791905 | Hs.95549 | hypothetical protein | 29.3 |
| 445033 | AV652402 | Hs.155145 | ESTs | 29.2 |
| 452367 | U71207 | Hs.29279 | eyes absent (Drosophila) homolog 2 | 29.1 |
| 432706 | NM_013230 | Hs.286124 | CD24 | 29.0 |
| 422163 | AF027208 | Hs.297332 | prominin (mouse)-like 1 | 28.7 |
| 447035 | NM_004753 | Hs.17144 | short-chain dehydrogenase/reductase 1 | 28.6 |
| 443958 | BE241880 | Hs.10029 | cathepsin C | 28.2 |
| 422956 | BE545072 | Hs.122579 | ESTs | 28.1 |
| 450377 | AB033091 | Hs.24936 | ESTs | 28.0 |
| 447471 | AF039843 | Hs.18676 | sprouty (Drosophila) homolog 2 | 28.0 |
| 444725 | AW952022 | Hs.234174 | Homo sapiens cDNA FLJ13819 fis, clone THYRO10 | 27.8 |
| 430250 | NM_016929 | Hs.283021 | chloride intracellular channel 5 | 27.7 |
| 416305 | AU076628 | Hs.79187 | coxsackie virus and adenovirus receptor | 27.6 |
| 418174 | L20688 | Hs.83656 | Rho GDP dissociation inhibitor (GDI) beta | 27.5 |
| 417233 | W25005 | Hs.24395 | small inducible cytokine subfamily B (Cys-X-C | 27.4 |
| 417866 | AW067903 | Hs.82772 | collagen, type XI, alpha 1 | 27.3 |
| 427344 | NM_000869 | Hs.2142 | 5-hydroxytryptamine (serotonin) receptor 3A | 27.2 |
| 442993 | BE018682 | Hs.44343 | ESTs | 27.2 |
| 407137 | T97307 | Hs.199067 | v-erb-b2 avian erythroblastic leukemia viral | 27.0 |
| 419356 | AI656166 | Hs.7331 | ESTs | 27.0 |
| 433662 | W07162 | Hs.150826 | CATX-8 protein | 26.7 |
| 422576 | BE548555 | Hs.118554 | CGI-83 protein | 26.4 |
| 423271 | W47225 | Hs.126256 | interleukin 1, beta | 26.3 |
| 443715 | AI583187 | Hs.9700 | cyclin E1 | 26.1 |
| 420186 | NM_015925 | Hs.95697 | liver-specific bHLH-Zip transcription factor | 26.0 |
| 419551 | AW582256 | Hs.91011 | anterior gradient 2 (Xenepus laevis) homolog | 25.9 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 443672 | AA323362 | Hs.9667 | butyrobetaine (gamma), 2-oxoglutarate dioxyge | 25.8 |
| 416889 | AW250318 | Hs.80395 | mal, T-cell differentiation protein | 25.3 |
| 408474 | AA188823 | Hs.83196 | *Homo sapiens* cDNA: FLJ23597 fis, clone LNG152 | 25.3 |
| 411825 | AK000334 | Hs.72289 | hypothetical protein FLJ20327 | 25.3 |
| 400881 | | | 0 | 25.2 |
| 440594 | AW445167 | Hs.126036 | ESTs | 25.1 |
| 414586 | AA306160 | Hs.76506 | lymphocyte cytosolic protein 1 (L-plastin) | 25.1 |
| 411925 | AW014588 | Hs.72925 | chromosome 11 open reading frame 13 | 25.1 |
| 417869 | BE076254 | Hs.82793 | proteasome (prosome, macropain) subunit, beta | 25.0 |
| 433447 | U29195 | Hs.3281 | neuronal pentraxin II | 25.0 |
| 450858 | C18458 | Hs.25597 | elongation of very long chain fatty acids (FE | 24.8 |
| 410619 | BE512730 | Hs.65114 | keratin 18 | 24.8 |
| 434094 | AA305599 | Hs.238205 | hypothetical protein PRO2013 | 24.6 |
| 421924 | BE514514 | Hs.109606 | coronin, actin-binding protein, 1A | 24.6 |
| 446859 | AI494299 | Hs.16297 | COX17 (yeast) homolog, cytochrome c oxidase a | 24.5 |
| 421451 | AA291377 | Hs.50831 | ESTs | 24.3 |
| 433929 | AI375499 | Hs.27379 | ESTs | 24.3 |
| 438930 | AW843633 | Hs.81256 | S100 calcium-binding protein A4 (calcium prot | 24.2 |
| 444212 | AW503976 | Hs.10649 | basement membrane-induced gene | 24.2 |
| 441633 | AW958544 | Hs.112242 | ESTs | 24.2 |
| 441134 | W29092 | Hs.7678 | cellular retinoic acid-binding protein 1 | 24.2 |
| 417715 | AW969587 | Hs.86366 | ESTs | 24.1 |
| 409361 | NM_005982 | Hs.54416 | sine oculis homeobox (*Drosophila*) homolog 1 | 24.1 |
| 416984 | H38765 | Hs.80706 | diaphorase (NADH/NADPH) (cytochrome b-5 reduc | 24.1 |
| 430125 | U46418 | Hs.233950 | serine protease inhibitor, Kunitz type 1 | 23.9 |
| 434078 | AW880709 | Hs.283683 | EST | 23.8 |
| 408669 | AI493591 | Hs.78146 | platelet/endothelial cell adhesion molecule ( | 23.8 |
| 439413 | AI598252 | Hs.37810 | ESTs | 23.7 |
| 449034 | AI624049 | Hs.277523 | gb: ts41a09.x1 NCI_CGAP_Ut1 *Homo sapiens* cDNA | 23.7 |
| 420344 | BE463721 | Hs.97101 | Putative G protein-coupled receptor GPCR150 | 23.6 |
| 431243 | U46455 | Hs.252189 | syndecan 4 (amphiglycan, ryudocan) | 23.6 |
| 417515 | L24203 | Hs.82237 | ataxia-telangiectasia group D-associated prot | 23.5 |
| 451267 | AI033894 | Hs.117865 | solute carrier family 17 (anion/sugar transpo | 23.4 |
| 450101 | AV649989 | Hs.24385 | Human hbc647 mRNA sequence | 23.4 |
| 419693 | AA133749 | Hs.92323 | FXYD domain-containing ion transport regulato | 23.4 |
| 431103 | M57399 | Hs.44 | pleiotrophin (heparin binding growth factor 8 | 23.4 |
| 451110 | AI955040 | Hs.301584 | ESTs | 23.3 |
| 426295 | AW367283 | Hs.75839 | zinc finger protein 6 (CMPX1) | 23.2 |
| 448517 | AA082750 | Hs.42194 | hypothetical protein FLJ22649 similar to sign | 23.1 |
| 424670 | W61215 | Hs.116651 | epithelial V-like antigen 1 | 23.1 |
| 417847 | AI521558 | Hs.288312 | *Homo sapiens* cDNA: FLJ22316 fis, clone HRC052 | 23.1 |
| 449027 | AJ271216 | Hs.22880 | dipeptidylpeptidase III | 23.1 |
| 424969 | AW950928 | Hs.153998 | creatine kinase, mitochondrial 1 (ubiquitous) | 23.1 |
| 433159 | AB035898 | Hs.150587 | kinesin-like protein 2 | 23.0 |
| 411393 | AW797437 | Hs.69771 | B-factor, properdin | 23.0 |
| 434815 | AF155582 | Hs.46744 | core1 UDP-galactose:N-acetylgalactosamine-alp | 22.8 |
| 427585 | D31152 | Hs.179729 | collagen; type X; alpha 1 (Schmid metaphyseal | 22.7 |
| 445721 | H92136 | Hs.13144 | HSPC160 protein | 22.6 |
| 448258 | BE386983 | Hs.85015 | ESTs, Weakly similar to A4P_HUMAN INTESTINAL | 22.6 |
| 456844 | AI264155 | Hs.152981 | CDP-diacylglycerol synthase (phosphatidate cy | 22.6 |
| 452698 | NM_001295 | Hs.301921 | ESTs | 22.5 |
| 418693 | AI750878 | Hs.87409 | thrombospondin 1 | 22.4 |
| 414880 | AW247305 | Hs.119140 | eukaryotic translation initiation factor 5A | 22.4 |
| 401519 | | | 0 | 22.3 |
| 402496 | | | 0 | 22.3 |
| 420324 | AF163474 | Hs.96744 | DKFZP586D0823 protein, Prostate androgen-regu | 22.3 |
| 403022 | | | 0 | 22.2 |
| 434042 | AI589941 | Hs.8254 | hypothetical protein PRO0899 | 22.1 |
| 419080 | AW150835 | Hs.18878 | hypothetical protein FLJ21620 | 22.1 |
| 406545 | AB018249 | Hs.10458 | small inducible cytokine subfamily A (Cys—Cys | 22.1 |
| 447362 | AW176120 | Hs.9061 | ESTs | 22.0 |
| 429547 | AW009166 | Hs.99376 | ESTs | 22.0 |
| 427954 | J03060 | Hs.247551 | metaxin 1 | 22.0 |
| 423161 | AL049227 | Hs.124776 | *Homo sapiens* mRNA; cDNA DKFZp564N1116 (from c | 22.0 |
| 428392 | H10233 | Hs.2265 | secretory granule, neuroendocrine protein 1 ( | 21.9 |
| 444107 | T46839 | Hs.10319 | UDP glycosyltransferase 2 family, polypeptide | 21.7 |
| 414421 | AI521130 | Hs.55567 | ESTs, Weakly similar to LAK-4p [*H. sapiens*] | 21.5 |
| 412589 | R28660 | Hs.24305 | ESTs | 21.5 |
| 446525 | AW967069 | Hs.211556 | *Homo sapiens* cDNA: FLJ23378 fis, clone HEP162 | 21.5 |
| 416847 | L43821 | Hs.80261 | enhancer of filamentation 1 (cas-like docking | 21.5 |
| 436972 | AA284679 | Hs.25640 | claudin 3 | 21.5 |
| 428698 | AA852773 | Hs.297939 | ESTs; Weakly similar to neogenin [*H. sapiens*] | 21.5 |
| 421340 | F07783 | Hs.1369 | decay accelerating factor for complement (CD5 | 21.4 |
| 413966 | AA133935 | Hs.173704 | ESTs | 21.4 |
| 448243 | AW369771 | Hs.77496 | ESTs | 21.3 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 421928 | AF013758 | Hs.109643 | polyadenylate binding protein-interacting pro | 21.3 |
| 403399 | | | 0 | 21.3 |
| 435793 | AB037734 | Hs.4993 | ESTs | 21.3 |
| 432629 | AW860548 | Hs.280658 | ESTs | 21.2 |
| 449057 | AB037784 | Hs.22941 | ESTs | 21.2 |
| 437575 | AW954355 | Hs.36529 | ESTs | 21.2 |
| 401131 | | | 0 | 21.0 |
| 407207 | T03651 | Hs.179661 | tubulin, beta polypeptide | 20.8 |
| 444783 | AK001468 | Hs.62180 | ESTs | 20.8 |
| 426230 | AA367019 | Hs.241395 | protease, serine, 1 (trypsin 1) | 20.8 |
| 447343 | AA256641 | Hs.236894 | ESTs; Highly similar to LOW-DENSITY LIPOPROTE | 20.7 |
| 409041 | AB033025 | Hs.50081 | KIAA1199 protein | 20.6 |
| 421305 | BE397354 | Hs.289721 | diptheria toxin resistance protein required f | 20.6 |
| 411704 | AI499220 | Hs.71573 | hypothetical protein FLJ10074 | 20.5 |
| 417018 | M16038 | Hs.80887 | v-yes-1 Yamaguchi sarcoma viral related oncog | 20.5 |
| 432827 | Z68128 | Hs.3109 | Rho GTPase activating protein 4 | 20.4 |
| 410174 | AA306007 | Hs.59461 | DKFZP434C245 protein | 20.4 |
| 425184 | BE278288 | Hs.155048 | Lutheran blood group (Auberger b antigen incl | 20.4 |
| 452322 | BE566343 | Hs.28988 | glutaredoxin (thioltransferase) | 20.3 |
| 447526 | AL048753 | Hs.340 | small inducible cytokine A2 (monocyte chemota | 20.2 |
| 447335 | BE617695 | Hs.286192 | protein phosphatase 1, regulatory (inhibitor) | 20.2 |
| 424867 | AI024860 | Hs.153591 | Not56 (*D. melanogaster*)-like protein | 20.1 |
| 410275 | U85658 | Hs.61796 | transcription factor AP-2 gamma (activating e | 20.1 |
| 429083 | Y09397 | Hs.227817 | BCL2-related protein A1 | 20.0 |
| 410173 | AA706017 | Hs.119944 | ESTs | 19.8 |
| 433047 | M86135 | Hs.279946 | methionine-tRNA synthetase | 19.8 |
| 419088 | AI538323 | Hs.77496 | ESTs | 19.7 |
| 403381 | | | 0 | 19.6 |
| 409162 | H25530 | Hs.50868 | solute carrier family 22 (organic cation tran | 19.5 |
| 426150 | NM_003658 | Hs.167218 | BarH-like homeobox 2 | 19.4 |
| 449292 | AI990292 | Hs.225457 | ESTs | 19.4 |
| 425207 | AB014551 | Hs.155120 | rho/rac guanine nucleotide exchange factor (G | 19.4 |
| 419950 | AK001645 | Hs.93871 | hypothetical protein FLJ10783 | 19.3 |
| 436481 | AA379597 | Hs.5199 | HSPC150 protein similar to ubiquitin-conjugat | 19.3 |
| 445930 | AF055009 | Hs.13456 | *Homo sapiens* clone 24747 mRNA sequence | 19.2 |
| 446608 | N75217 | Hs.257846 | ESTs | 19.1 |
| 425222 | M85430 | Hs.155191 | villin 2 (ezrin) | 19.1 |
| 428309 | M97815 | Hs.183650 | cellular retinoic acid-binding protein 2 | 19.1 |
| 420005 | AW271106 | Hs.133294 | ESTs | 19.1 |
| 436982 | AB018305 | Hs.5378 | spondin 1, (f-spondin) extracellular matrix p | 19.0 |
| 407142 | AA412535 | Hs.55235 | sphingomyelin phosphodiesterase 2, neutral me | 19.0 |
| 430122 | NM_013342 | Hs.233765 | TCF3 (E2A) fusion partner (in childhood Leuke | 18.9 |
| 446293 | AI420213 | Hs.149722 | ESTs | 18.9 |
| 444825 | AW167613 | Hs.248 | mitogen-activated protein kinase kinase kinas | 18.9 |
| 407634 | AW016569 | Hs.301280 | UDP-GlcNAc:betaGal beta-1,3-N-acetylglucosami | 18.9 |
| 445200 | AA084460 | Hs.12409 | somatostatin | 18.9 |
| 418917 | X02994 | Hs.1217 | adenosine deaminase | 18.8 |
| 435777 | AW419202 | Hs.286192 | protein phosphatase 1, regulatory (inhibitor) | 18.8 |
| 431049 | AA846576 | Hs.103267 | hypothetical protein FLJ22548 similar to gene | 18.7 |
| 426427 | M86699 | Hs.169840 | TTK protein kinase | 18.7 |
| 436281 | AW411194 | Hs.120051 | ESTs | 18.6 |
| 425907 | AA365752 | Hs.155965 | ESTs | 18.6 |
| 459720 | | | ESTs | 18.6 |
| 421242 | AW161386 | Hs.13561 | ESTs, Weakly similar to dJ37E16.5 [*H. sapiens*] | 18.5 |
| 457715 | AA642402 | Hs.59142 | ESTs | 18.5 |
| 451668 | Z43948 | Hs.26789 | ASPIC (acidic secreted protein in cartilage)A | 18.4 |
| 437142 | AI791617 | Hs.145068 | ESTs | 18.4 |
| 418588 | BE387040 | Hs.182476 | ESTs, Weakly similar to similar to alpha/beta | 18.3 |
| 433068 | NM_006456 | Hs.288215 | sialyltransferase | 18.3 |
| 419854 | AW664873 | Hs.87836 | *Homo sapiens* PAC clone RP5-1087M19 from 7q11. | 18.3 |
| 444726 | NM_006147 | Hs.11801 | interferon regulatory factor 6 | 18.3 |
| 423011 | NM_000683 | Hs.299847 | ESTs, Highly similar to A2AD_HUMAN ALPHA-2C-2 | 18.2 |
| 451428 | AW083384 | Hs.11067 | ESTs, Weakly similar to K02E10.2 [*C. elegans*] | 18.2 |
| 424865 | AF011333 | Hs.153563 | lymphocyte antigen 75 | 18.2 |
| 418742 | AW451197 | Hs.113418 | ESTs | 18.1 |
| 446627 | AI973016 | Hs.15725 | ESTs; hypothetical protein SBBI48 | 18.1 |
| 424885 | AI333771 | Hs.82204 | ESTs | 18.1 |
| 402926 | | | 0 | 18.0 |
| 405452 | | | 0 | 18.0 |
| 428641 | AA431367 | Hs.234546 | GMPR2 for guanosine monophosphate reductase i | 18.0 |
| 454390 | AB020713 | Hs.56966 | KIAA0906 protein | 18.0 |
| 441784 | AI522132 | Hs.28700 | ESTs | 18.0 |
| 418758 | AW959311 | Hs.87019 | ESTs | 17.9 |
| 408621 | AI970672 | Hs.46638 | chromosome 11 open reading frame 8; fetal br | 17.9 |
| 426201 | AW182614 | Hs.128499 | ESTs | 17.8 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 410442 | X73424 | Hs.63788 | propionyl Coenzyme A carboxylase, beta polype | 17.8 |
| 456423 | AW748920 | | gb: CM2-BT0306-171199-034-g02 BT0306 *Homo sapi* | 17.8 |
| 422867 | L32137 | Hs.1584 | cartilage oligomeric matrix protein | 17.8 |
| 448110 | AA626937 | Hs.181551 | ESTs | 17.7 |
| 421750 | AK000768 | Hs.107872 | hypothetical protein FLJ20761 | 17.7 |
| 405224 | | | 0 | 17.7 |
| 447630 | AI660149 | Hs.44865 | lymphoid enhancer-binding factor 1 | 17.7 |
| 407663 | NM_016429 | Hs.37482 | COPZ2 for nonclathrin coat protein zeta-COP | 17.7 |
| 427490 | Z95152 | Hs.178695 | mitogen-activated protein kinase 13 | 17.6 |
| 414812 | X72755 | Hs.77367 | monokine induced by gamma interferon | 17.6 |
| 427691 | AW194426 | Hs.20726 | ESTs | 17.6 |
| 420650 | AA455706 | Hs.44581 | heat shock protein hsp70-related protein | 17.5 |
| 439841 | AF038961 | Hs.6710 | mannose-P-dolichol utilization defect 1 | 17.5 |
| 425810 | AI923627 | Hs.31903 | ESTs | 17.5 |
| 425397 | J04088 | Hs.156346 | topoisomerase (DNA) II alpha (170 kD) | 17.5 |
| 456068 | AW747800 | Hs.55016 | hypothetical protein FLJ21935 | 17.4 |
| 428579 | NM_005756 | Hs.184942 | G protein-coupled receptor 64 | 17.4 |
| 410361 | BE391804 | Hs.62661 | guanylate binding protein 1, interferon-induc | 17.4 |
| 442402 | NM_000954 | Hs.8272 | prostaglandin D2 synthase (21 kD, brain) | 17.4 |
| 411734 | AW374954 | Hs.71779 | *Homo sapiens* DNA from chromosome 19, cosmid F | 17.3 |
| 405295 | | | 0 | 17.3 |
| 408340 | AB037762 | Hs.44268 | myelin gene expression factor 2 | 17.3 |
| 456068 | AI677897 | Hs.76640 | RGC32 protein | 17.3 |
| 448571 | AA486794 | Hs.66915 | ESTs, Weakly similar to 16.7 Kd protein [*H. sap* | 17.2 |
| 441829 | AL117482 | Hs.7978 | DKFZP434C131 protein | 17.2 |
| 418004 | U37519 | Hs.87539 | aldehyde dehydrogenase 8 | 17.2 |
| 412078 | X69699 | Hs.73149 | paired box gene 8 | 17.2 |
| 414658 | X58528 | Hs.76781 | ATP-binding cassette, sub-family D (ALD), mem | 17.1 |
| 418478 | U38945 | Hs.1174 | cyclin-dependent kinase inhibitor 2A (melanom | 17.0 |
| 426805 | AB032945 | Hs.172506 | myosin VB | 17.0 |
| 410247 | AF181721 | Hs.61345 | RU2S | 17.0 |
| 434516 | AA807814 | Hs.70582 | ESTs, Moderately similar to AF144056 1 apopto | 16.9 |
| 428153 | AW513143 | Hs.98367 | hypothetical protein FLJ22252 similar to SRY- | 16.9 |
| 417793 | AW405434 | Hs.82575 | small nuclear ribonucleoprotein polypeptide B | 16.9 |
| 454163 | AW175997 | | gb: QV0-BT0078-190899-005-E02 BT0078 *Homo sapi* | 16.9 |
| 415402 | AA164687 | Hs.297889 | ESTs | 16.9 |
| 420309 | AW043637 | Hs.21766 | ESTs | 16.9 |
| 419201 | M22324 | Hs.1239 | alanyl (membrane) aminopeptidase (aminopeptid | 16.9 |
| 444391 | AL137597 | Hs.11114 | hypothetical protein dJ1181N3.1 | 16.9 |
| 457705 | AW974668 | | gb: EST386757 MAGE resequences, MAGM *Homo sapi* | 16.8 |
| 412723 | AA648459 | Hs.179912 | ESTs | 16.8 |
| 435774 | R88066 | Hs.4992 | tumor suppressing subtransferable candidate 1 | 16.8 |
| 408753 | AI337192 | Hs.47438 | SH3 domain binding glutamic acid-rich protein | 16.8 |
| 447783 | AF054178 | Hs.19561 | NADH dehydrogenase (ubiquinone) 1 alpha subco | 16.8 |
| 418085 | R40328 | Hs.258822 | ESTs | 16.7 |
| 452472 | AW957300 | Hs.294142 | ESTs, Weakly similar to SP49_HUMAN SPLICEOSOM | 16.7 |
| 409112 | BE243971 | Hs.50649 | quinone oxidoreductase homolog | 16.7 |
| 410250 | AI082777 | Hs.61384 | KIAA1445 protein | 16.7 |
| 446219 | AI287344 | Hs.149827 | ESTs | 16.6 |
| 428928 | BE409838 | Hs.194657 | cadherin 1, type 1, E-cadherin (epithelial) | 16.6 |
| 425812 | AA364128 | Hs.245633 | ESTs | 16.6 |
| 411742 | AW247593 | Hs.71819 | eukaryotic translation initiation factor 4E b | 16.6 |
| 415076 | NM_000857 | Hs.77890 | guanylate cyclase 1, soluble, beta 3 | 16.6 |
| 416209 | AA236776 | Hs.79078 | MAD2 (mitotic arrest deficient, yeast, homolo | 16.6 |
| 440667 | BE076969 | Hs.7337 | hypothetical protein FLJ10936 | 16.6 |
| 430375 | AW371048 | Hs.93758 | H4 histone family, member H | 16.6 |
| 419607 | R52557 | Hs.91579 | *Homo sapiens* clone 23783 mRNA sequence | 16.6 |
| 410328 | BE080190 | Hs.62275 | CGI-141 protein | 16.5 |
| 405426 | | | 0 | 16.5 |
| 432636 | AA340864 | Hs.278562 | claudin 7 | 16.5 |
| 434725 | AK000796 | Hs.4104 | hypothetical protein | 16.5 |
| 414683 | S78296 | Hs.76888 | internexin neuronal intermediate filament pro | 16.5 |
| 429500 | X78565 | Hs.289114 | hexabrachion (tenascin C, cytotactin) | 16.5 |
| 449944 | AF290512 | Hs.58215 | *Homo sapiens* rhotekin mRNA, partial cds | 16.4 |
| 400666 | | | 0 | 16.4 |
| 421536 | BE250690 | Hs.105509 | CTL2 gene | 16.4 |
| 436032 | AA150797 | Hs.109276 | latexin protein | 16.4 |
| 418196 | AI745649 | Hs.26549 | ESTs, Weakly similar to T00066 hypothetical p | 16.4 |
| 452323 | W44356 | Hs.292812 | ESTs, Weakly similar to C43H8.1 [*C. elegans*] | 16.4 |
| 407699 | AA825974 | Hs.32646 | *Homo sapiens* cDNA: FLJ21901 fis, clone HEP034 | 16.4 |
| 414617 | AI339520 | Hs.20524 | ESTs, Moderately similar to hexokinase I [*H. s* | 16.3 |
| 408204 | AA454501 | Hs.43666 | protein tyrosine phosphatase type IVA, member | 16.3 |
| 452650 | AW270150 | Hs.254516 | ESTs | 16.3 |
| 432906 | BE265489 | Hs.3123 | lethal giant larvae (*Drosophila*) homolog 2 | 16.3 |
| 402408 | | | 0 | 16.3 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 408805 | H69912 | Hs.48269 | vaccinia related kinase 1 | 16.3 |
| 447155 | AA100605 | Hs.121557 | ESTs, Weakly similar to AF251041 1 SGC32445 p | 16.3 |
| 405699 | | | 0 | 16.2 |
| 406893 | M22406 | | gb: Human intestinal mucin mRNA, partial cds, | 16.2 |
| 418629 | BE247550 | Hs.86859 | growth factor receptor-bound protein 7 (GRB7) | 16.2 |
| 424905 | NM_002497 | Hs.153704 | NIMA (never in mitosis gene a)-related kinase | 16.2 |
| 424243 | AI949359 | Hs.301837 | ESTs, Highly similar to cis Golgi-localized c | 16.2 |
| 418462 | BE001596 | Hs.85266 | integrin, beta 4 | 16.1 |
| 457205 | AI905780 | Hs.198272 | NADH dehydrogenase (ubiquinone) 1 beta subcom | 16.1 |
| 428188 | M98447 | Hs.22 | transglutaminase 1 (K polypeptide epidermal t | 16.1 |
| 449845 | AW971183 | Hs.60054 | ESTs | 16.1 |
| 406429 | | | 0 | 16.1 |
| 407375 | AA091354 | | gb: II0815.seq.F Human fetal heart, Lambda ZAP | 16.1 |
| 448377 | AI494514 | Hs.171380 | ESTs | 16.1 |
| 431156 | NM_002220 | Hs.2722 | inositol 1,4,5-trisphosphate 3-kinase A | 16.0 |
| 450043 | AA885699 | Hs.24332 | CGI-26 protein | 16.0 |
| 403121 | | | 0 | 16.0 |
| 400214 | | | 0 | 15.9 |
| 453252 | R02436 | Hs.215725 | ESTs | 15.9 |
| 451734 | NM_006176 | Hs.26944 | neurogranin (protein kinase C substrate, RC3) | 15.9 |
| 416855 | AA188763 | Hs.36793 | *Homo sapiens* cDNA: FLJ23188 fis, clone LNG120 | 15.9 |
| 424474 | AA308883 | Hs.148680 | calcyon; D1 dopamine receptor-interacting pro | 15.9 |
| 423685 | BE350494 | Hs.49753 | *Homo sapiens* mRNA for KIAA1561 protein, parti | 15.9 |
| 428187 | AI687303 | Hs.285529 | ESTs | 15.9 |
| 438817 | AI023799 | Hs.163242 | ESTs | 15.9 |
| 425692 | D90041 | Hs.155956 | NAT1; arylamine N-acetyltransferase | 15.9 |
| 421674 | T10707 | Hs.296355 | neuronal PAS domain protein 2 | 15.9 |
| 439999 | AA115811 | Hs.6838 | ras homolog gene family, member E | 15.9 |
| 411351 | W02919 | Hs.283476 | peroxisomal acyl-CoA thioesterase | 15.9 |
| 413027 | NM_002885 | Hs.75151 | RAP1, GTPase activating protein 1 | 15.9 |
| 453884 | AA355925 | Hs.36232 | KIAA0186 gene product | 15.8 |
| 407894 | AJ278313 | Hs.41143 | phosphoinositide-specific phospholipase C-bet | 15.8 |
| 422748 | AA316266 | Hs.129349 | ESTs | 15.8 |
| 414591 | AI888490 | Hs.55902 | ESTs | 15.8 |
| 421877 | AW250380 | Hs.109059 | mitochondrial ribosomal protein L12 | 15.8 |
| 404780 | | | 0 | 15.8 |
| 401192 | | | 0 | 15.8 |
| 447519 | U46258 | Hs.23448 | ESTs | 15.8 |
| 434262 | AF121858 | Hs.12169 | sorting nexin 8 | 15.7 |
| 451253 | H48299 | Hs.26126 | claudin 10 | 15.7 |
| 435499 | R89344 | Hs.14148 | ESTs | 15.7 |
| 422424 | AI186431 | Hs.116577 | prostate differentiation factor; placental bo | 15.7 |
| 424834 | AK001432 | Hs.153408 | *Homo sapiens* cDNA FLJ10570 fis, clone NT2RP20 | 15.7 |
| 424562 | AI420859 | Hs.150557 | basic transcription element binding protein 1 | 15.7 |
| 443247 | BE614387 | Hs.47378 | ESTs | 15.7 |
| 430696 | AA531276 | Hs.59509 | ESTs | 15.6 |
| 437044 | AL035864 | Hs.69517 | ESTs, highly similar to differentially expres | 15.6 |
| 428237 | AF175206 | Hs.183125 | killer cell lectin-like receptor F1 | 15.6 |
| 440048 | AA897461 | Hs.158469 | ESTs, Weakly similar to envelope protein [*H. s* | 15.6 |
| 414922 | D00723 | Hs.77631 | glycine cleavage system protein H (aminomethy | 15.6 |
| 422030 | X51416 | Hs.110849 | estrogen-related receptor alpha | 15.6 |
| 408716 | AI567839 | Hs.151714 | ESTs | 15.5 |
| 410258 | X52638 | Hs.739 | 6-phosphofructo-2-kinase/fructose-2,6-biphosp | 15.5 |
| 410530 | M25809 | Hs.64173 | ESTs, Highly similar to VAB1_HUMAN VACUOLAR A | 15.5 |
| 447072 | D61594 | Hs.17279 | tyrosylprotein sulfotransferase 1 | 15.5 |
| 409015 | BE389387 | Hs.49767 | NADH dehydrogenase (ubiquinone) Fe—S protein | 15.5 |
| 447549 | AI871120 | Hs.231265 | ESTs | 15.5 |
| 449704 | AK000733 | Hs.23900 | GTPase activating protein | 15.4 |
| 427337 | Z46223 | Hs.176663 | Fc fragment of IgG, low affinity IIIb, recept | 15.4 |
| 421630 | NM_001956 | Hs.1407 | endothelin 2 | 15.4 |
| 433018 | AI669760 | Hs.188881 | ESTs | 15.4 |
| 422938 | NM_001809 | Hs.1594 | centromere protein A (17 kD) | 15.3 |
| 407014 | U38268 | | gb: Human cytochrome b pseudogene, partical cds | 15.2 |
| 429311 | AF080157 | Hs.198998 | conserved helix-loop-helix ubiquitous kinase | 15.2 |
| 431842 | NM_005764 | Hs.271473 | epithelial protein up-regulated in carcinoma, | 15.2 |
| 406907 | Z25427 | | gb: *H. sapiens* protein-serine/threonine kinase | 15.2 |
| 458495 | AI202029 | Hs.148593 | ESTs | 15.2 |
| 420551 | AL137692 | Hs.98790 | *Homo sapiens* mRNA; cDNA DKFZp434P182 (from cl | 15.1 |
| 448443 | AW167128 | Hs.231934 | ESTs | 15.1 |
| 443646 | AI085198 | Hs.298699 | ESTs | 15.1 |
| 431538 | AL137547 | Hs.259619 | *Homo sapiens* mRNA; cDNA DKFZp434B1120 (from c | 15.1 |
| 436687 | AA868643 | Hs.120461 | ESTs | 15.1 |
| 420917 | AW135716 | Hs.117330 | ESTs | 15.0 |
| 428575 | M19684 | Hs.184929 | serine (or cysteine) proteinase inhibitor, cl | 15.0 |
| 403482 | | | 0 | 15.0 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 421499 | AI271438 | Hs.105022 | *Homo sapiens* PAC clone RP4-701O16 from 7q33-q | 15.0 |
| 401047 | | | 0 | 14.9 |
| 417749 | U09196 | Hs.82520 | polymerase (DNA-directed), delta 4 | 14.9 |
| 416693 | AI373204 | Hs.79531 | *Homo sapiens* TTF-I interacting peptide 20 mRN | 14.9 |
| 428474 | AB023182 | Hs.184523 | KIAA0965 protein | 14.9 |
| 428862 | NM_000346 | Hs.2316 | SRY (sex-determining region Y)-box 9 (campome | 14.9 |
| 430271 | T06199 | Hs.237506 | heat shock cognate 40 | 14.9 |
| 414328 | Z21666 | Hs.75900 | aconitase 2, mitochondrial | 14.9 |
| 415314 | N88802 | Hs.5422 | glycoprotein M6B | 14.8 |
| 453735 | AI066629 | Hs.125073 | ESTs | 14.8 |
| 424345 | AK001380 | Hs.145479 | *Homo sapiens* cDNA FLJ10518 fis, clone NT2RP20 | 14.8 |
| 423575 | C18863 | Hs.163443 | ESTs | 14.8 |
| 438081 | H49546 | Hs.298964 | ESTs | 14.8 |
| 403485 | | | 0 | 14.8 |
| 452114 | N22687 | Hs.8236 | ESTs | 14.8 |
| 426559 | AB001914 | Hs.170414 | paired basic amino acid cleaving system 4 | 14.8 |
| 412869 | AA290712 | Hs.82407 | *Homo sapiens* HSPC296 mRNA, partial cds | 14.8 |
| 452101 | T60298 | | gb: yb87f12.r1 Stratagene liver (937224) *Homo* | 14.7 |
| 420505 | AW967984 | Hs.291612 | ESTs | 14.7 |
| 426125 | X87241 | Hs.166994 | FAT tumor suppressor (*Drosophila*) homolog | 14.7 |
| 433336 | AF017986 | Hs.31386 | ESTs; Highly similar to FRIZZLED PROTEIN PRE | 14.7 |
| 428977 | AK001404 | Hs.194698 | cyclin B2 | 14.7 |
| 429785 | H82114 | Hs.301769 | ESTs | 14.7 |
| 402424 | | | 0 | 14.7 |
| 424971 | AA479005 | Hs.154036 | tumor suppressing subtransferable candidate 3 | 14.7 |
| 433037 | NM_014158 | Hs.279938 | HSPC067 protein | 14.6 |
| 421670 | BE207318 | Hs.106674 | BRCA1 associated protein-1 (ubiquitin carboxy | 14.6 |
| 438598 | AI805943 | Hs.5723 | *Homo sapiens* cDNA: FLJ23439 fis, clone HSI001 | 14.6 |
| 453370 | AI470523 | Hs.182356 | ESTs, Moderately similar to translation initi | 14.6 |
| 410561 | BE540255 | Hs.6994 | *Homo sapiens* cDNA: FLJ22044 fis, clone HEP091 | 14.6 |
| 402287 | | | 0 | 14.6 |
| 419741 | NM_007019 | Hs.93002 | ubiquitin carrier protein E2-C | 14.6 |
| 442047 | AA974598 | Hs.150324 | ESTs | 14.5 |
| 428582 | BE336699 | Hs.185055 | BENE protein | 14.5 |
| 440006 | AK000517 | Hs.6844 | hypothetical protein FLJ20510 | 14.5 |
| 406851 | AA609784 | Hs.180255 | major histocompatibility complex, class II, D | 14.5 |
| 457316 | AI123657 | Hs.127264 | ESTs | 14.5 |
| 420453 | AL157500 | Hs.97840 | *Homo sapiens* mRNA; cDNA DKFZp434G015 (from cl | 14.5 |
| 436406 | AW105723 | Hs.125346 | ESTs | 14.5 |
| 420736 | AI263022 | Hs.82204 | ESTs | 14.5 |
| 419743 | AW408762 | Hs.127478 | ESTs | 14.5 |
| 429113 | D28235 | Hs.196384 | Prostaglandin-endoperoxide synthase 2 (COX-2) | 14.5 |
| 450256 | AA286887 | Hs.24724 | MFH-amplified sequences with leucine-rich tan | 14.5 |
| 424906 | AI566086 | Hs.153716 | *Homo sapiens* mRNA for Hmob33 protein, 3' untr | 14.5 |
| 427414 | F11750 | Hs.6647 | *Homo sapiens* cDNA FLJ13088 fis, clone NT2RP30 | 14.4 |
| 419839 | U24577 | Hs.93304 | phospholipase A2, group VII (platelet-activat | 14.4 |
| 418738 | AW388633 | Hs.6682 | solute carrier family 7, member 11 | 14.3 |
| 429414 | AI783656 | Hs.202095 | empty spiracles (*Drosophila*) homolog 2 | 14.3 |
| 424669 | AA417181 | Hs.120858 | *Homo sapiens* cDNA FLJ13945 fis, clone Y79AA10 | 14.3 |
| 408989 | AW361666 | Hs.49500 | KIAA0746 protein | 14.3 |
| 406788 | AI911841 | Hs.5184 | TH1 *drosophila* homolog | 14.3 |
| 417861 | AA334551 | Hs.82767 | sperm specific antigen 2 | 14.3 |
| 402104 | | | 0 | 14.3 |
| 416368 | R88849 | | gb: ym96a06.r1 Soares adult brain N2b4HB55Y *Ho* | 14.2 |
| 405802 | | | 0 | 14.2 |
| 448357 | N20169 | Hs.108923 | ESTs | 14.2 |
| 444261 | AA298958 | Hs.10724 | MDS023 protein | 14.2 |
| 407846 | AA426202 | Hs.40403 | Cbp/p300-interacting transactivator, with Glu | 14.2 |
| 425163 | D10040 | Hs.154890 | fatty-acid-Coenzyme A ligase, long-chain 2 | 14.1 |
| 402520 | | | 0 | 14.1 |
| 429597 | NM_003816 | Hs.2442 | a disintegrin and metalloproteinase domain 9 | 14.1 |
| 430044 | AA464510 | Hs.152812 | EST cluster (not in UniGene) | 14.1 |
| 429663 | M68874 | Hs.211587 | Human phosphatidylcholine 2-acylhydrolase (cP | 14.1 |
| 427036 | AA397625 | Hs.163913 | ESTs | 14.1 |
| 444381 | BE387335 | Hs.283713 | ESTs | 14.1 |
| 432090 | AW972855 | Hs.292853 | ESTs | 14.0 |
| 406778 | H06273 | Hs.101651 | *Homo sapiens* mRNA; cDNA DKFZp434C107 (from cl | 14.0 |
| 404961 | AW972195 | Hs.284236 | aldo-keto reductase family 7, member A3 (afla | 14.0 |
| 452313 | Y00486 | Hs.28914 | adenine phosphoribosyltransferase | 14.0 |
| 452355 | N54926 | Hs.29202 | G protein-coupled receptor 34 | 14.0 |
| 429942 | AI338993 | Hs.134535 | ESTs | 14.0 |
| 403165 | | | 0 | 13.9 |
| 442150 | AI368158 | Hs.128864 | ESTs | 13.9 |
| 439709 | AW401433 | Hs.6649 | hypothetical protein FLJ20128 | 13.9 |
| 456799 | AC004923 | Hs.135187 | *Homo sapiens* clone CDABP0025 mRNA sequence | 13.9 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 427356 | AW023482 | Hs.97849 | ESTs | 13.9 |
| 448982 | AI638164 | Hs.225520 | ESTs | 13.9 |
| 432025 | BE407132 | Hs.111286 | hypothetical protein FLJ22512 | 13.8 |
| 427505 | AA361562 | Hs.178761 | 26S proteasome-associated pad1 homolog | 13.8 |
| 402965 | | | 0 | 13.8 |
| 418601 | AA279490 | Hs.86368 | calmegin | 13.8 |
| 436954 | AA740151 | Hs.130425 | ESTs | 13.8 |
| 405024 | | | 0 | 13.8 |
| 453976 | BE463830 | Hs.163714 | ESTs | 13.8 |
| 431921 | N46466 | Hs.58879 | ESTs | 13.8 |
| 401735 | | | 0 | 13.8 |
| 445496 | AB007860 | Hs.12802 | development and differentiation enhancing fac | 13.8 |
| 425007 | AA456483 | Hs.172081 | phosphodiesterase 4D, cAMP-specific (dunce (D | 13.7 |
| 409463 | AI458165 | Hs.17296 | ESTs | 13.7 |
| 430193 | AI826653 | Hs.102928 | *Homo sapiens* cDNA FLJ13479 fis, clone PLACE10 | 13.7 |
| 458869 | AI637934 | Hs.224978 | ESTs | 13.7 |
| 426769 | AA075596 | Hs.172153 | glutathione peroxidase 3 (plasma) | 13.7 |
| 416661 | AA634543 | Hs.79440 | IGF-II mRNA-binding protein 3 | 13.7 |
| 439901 | N73885 | Hs.124169 | ESTs | 13.7 |
| 431374 | BE258532 | Hs.251871 | CTP synthase | 13.7 |
| 432861 | AA339526 | Hs.279593 | HSPC171 protein | 13.7 |
| 441172 | AI279652 | Hs.132879 | ESTs | 13.7 |
| 410001 | AB041036 | Hs.57771 | kallikrein 11; serine protease (TLSP) | 13.7 |
| 430315 | NM_004293 | Hs.239147 | guanine deaminase | 13.6 |
| 422769 | AA938905 | Hs.289112 | CGI-43 protein | 13.6 |
| 402389 | | | 0 | 13.6 |
| 448977 | X91809 | Hs.22698 | regulator of G-protein signalling 19 | 13.6 |
| 459648 | | | gb: IL3-CT0220-150200-070-B02 CT0220 *Homo sapi* | 13.6 |
| 452972 | M31732 | Hs.31210 | B-cell CLL/lymphoma 3 | 13.6 |
| 431441 | U81961 | Hs.2794 | sodium channel, nonvoltage-gated 1 alpha | 13.6 |
| 448585 | AB020676 | Hs.21543 | KIAA0869 protein | 13.6 |
| 428385 | AF112213 | Hs.184062 | putative Rab5-interacting protein | 13.6 |
| 434699 | AA643687 | Hs.149425 | *Homo sapiens* cDNA FLJ11980 fis, clone HEMBB10 | 13.6 |
| 447238 | AW451676 | Hs.158564 | ESTs | 13.6 |
| 437108 | AA434054 | Hs.80624 | *Homo sapiens* cDNA: FLJ23442 fis, clone HSI009 | 13.6 |
| 425749 | AW328587 | Hs.159448 | surfeit 2 | 13.5 |
| 425154 | NM_001851 | Hs.154850 | collagen, type IX, alpha 1 | 13.5 |
| 413753 | U17760 | Hs.301103 | Laminin, beta 3 (nicein (125 kD), kalinin (140 | 13.5 |
| 419034 | NM_002110 | Hs.89555 | hemopoietic cell kinase | 13.5 |
| 448361 | H82028 | Hs.238707 | *Homo sapiens* cDNA: FLJ22457 fis, clone HRC099 | 13.5 |
| 412754 | AW160375 | Hs.74565 | amyloid beta (A4) precursor-like protein 1 | 13.5 |
| 419081 | AI798863 | Hs.87191 | ESTs | 13.5 |
| 407732 | AW138839 | Hs.24210 | ESTs | 13.5 |
| 423329 | AF054910 | Hs.127111 | tektin 2 (testicular) | 13.5 |
| 422627 | BE336857 | Hs.118787 | transforming growth factor, beta-induced, 68k | 13.4 |
| 439636 | AF086467 | | gb: *Homo sapiens* full length insert cDNA clone | 13.4 |
| 417605 | AF006609 | Hs.82294 | regulator of G-protein signalling 3 | 13.4 |
| 445861 | BE293423 | Hs.11809 | single Ig IL-1R-related molecule | 13.4 |
| 447350 | AI375572 | Hs.172634 | ESTs; HER4 (c-erb-B4) | 13.4 |
| 451807 | W52854 | Hs.27099 | DKFZP564J0863 protein | 13.4 |
| 421515 | Y11339 | Hs.105352 | GalNAc alpha-2, 6-sialyltransferase I, long f | 13.4 |
| 422443 | NM_014707 | Hs.116753 | histone deacetylase 7B | 13.4 |
| 412504 | Z44496 | Hs.26039 | *Homo sapiens* cDNA FLJ13937 fis, clone Y79AA10 | 13.4 |
| 453344 | BE349075 | Hs.44571 | ESTs | 13.4 |
| 402885 | | | 0 | 13.4 |
| 438712 | AW978161 | Hs.169877 | ESTs | 13.4 |
| 421774 | AL050374 | Hs.108169 | DKFZP586C1619 protein | 13.3 |
| 425638 | NM_012337 | Hs.158450 | nasopharyngeal epithelium specific protein 1 | 13.3 |
| 401897 | | | 0 | 13.3 |
| 425601 | AW629485 | Hs.293352 | ESTs | 13.3 |
| 450779 | AW204145 | Hs.156044 | ESTs | 13.3 |
| 444858 | AI199738 | Hs.208275 | ESTs, Weakly similar to unnamed protein produ | 13.3 |
| 442619 | AA447492 | Hs.20183 | ESTs, Weakly similar to AF164793 1 protein x | 13.3 |
| 434263 | N34895 | Hs.44648 | ESTs | 13.3 |
| 426059 | BE292842 | Hs.166120 | interferon regulatory factor 7 | 13.3 |
| 407467 | D55638 | | gb: Human B-cell PABL (pseudoautosomal boundar | 13.3 |
| 412560 | R24601 | Hs.108300 | CCR4-NOT transcription complex, subunit 3 | 13.2 |
| 442986 | AI025990 | Hs.285520 | ESTs | 13.2 |
| 420317 | AB006628 | Hs.96485 | KIAA0290 protein | 13.2 |
| 443211 | AI128388 | Hs.143655 | ESTs | 13.2 |
| 434361 | AF129755 | Hs.117772 | ESTs | 13.2 |
| 423493 | AI815965 | Hs.129683 | ubiquitin-conjugating enzyme E2D 1 (homologou | 13.2 |
| 414183 | AW957446 | Hs.301711 | ESTs | 13.2 |
| 447778 | BE620592 | Hs.71190 | ESTs | 13.2 |
| 435106 | AA100847 | Hs.193380 | ESTs, Highly similar to AF174600 1 F-box prot | 13.1 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 439490 | AW249197 | Hs.100043 | ESTs, Weakly similar to PSF_HUMAN PTB-ASSOCIA | 13.1 |
| 409606 | AW444594 | Hs.2387 | transglutaminase 4 (prostate) | 13.1 |
| 421308 | AA687322 | Hs.192843 | ESTs | 13.1 |
| 414950 | C15407 | | gb: C15407 Clontech human aorta polyA+ mRNA (6 | 13.1 |
| 416783 | AA206186 | Hs.79889 | monocyte to macrophage differentiation-associ | 13.1 |
| 415927 | AL120168 | Hs.78919 | Kell blood group precursor (McLeod phenotype) | 13.1 |
| 422605 | H16646 | Hs.118666 | Human clone 23759 mRNA, partial cds | 13.0 |
| 430427 | AA296701 | Hs.241413 | opticin | 13.0 |
| 424620 | AA101043 | Hs.151254 | kallikrein 7 (chymotryptic; stratum corneum) | 13.0 |
| 421693 | X71490 | Hs.106876 | ATPase, H+ transporting, lysosomal (vacuolar | 13.0 |
| 407727 | AW411148 | Hs.38044 | DKFZP564M082 protein | 13.0 |
| 427706 | AW971225 | Hs.293800 | ESTs,Weakly similar to ALU1_HUMAN ALU SUBFAM | 13.0 |
| 406709 | AI355761 | Hs.242463 | keratin 8 | 13.0 |
| 405353 | | | 0 | 13.0 |
| 453060 | AW294092 | Hs.21594 | ESTs | 13.0 |
| 459299 | BE094291 | Hs.155651 | hepatocyte nuclear factor 3, beta | 13.0 |
| 447843 | AW337186 | Hs.224891 | ESTs | 13.0 |
| 446576 | AI659477 | Hs.51820 | ESTs, Moderately similar to ALU7_HUMAN ALU SU | 13.0 |
| 449700 | L02867 | Hs.78358 | ESTs | 13.0 |
| 436476 | AA326108 | Hs.53631 | ESTs | 13.0 |
| 432532 | AW058459 | Hs.162246 | ESTs | 13.0 |
| 408405 | AK001332 | Hs.44672 | hypothetical protein FLJ10470 | 13.0 |
| 432673 | AB028859 | Hs.278605 | ER-associated DNAJ; ER-associated Hsp40 co-ch | 12.9 |
| 414684 | AW630023 | Hs.76893 | 3-hydroxybutyrate dehydrogenase (heart, mitoc | 12.9 |
| 447210 | AF035269 | Hs.17752 | phosphatidylserine-specific phospholipase A1a | 12.9 |
| 427923 | AW274357 | Hs.268384 | Fzr1 protein | 12.9 |
| 437395 | AL365408 | Hs.10632 | hypothetical protein DKFZp762M136 | 12.9 |
| 441627 | AA947552 | Hs.58086 | ESTs | 12.9 |
| 419084 | AA496539 | Hs.179902 | transporter-like protein | 12.9 |
| 423067 | AA321355 | Hs.285401 | ESTs | 12.9 |
| 423070 | R55677 | Hs.155569 | ESTs | 12.8 |
| 441344 | BE250144 | Hs.41514 | ESTs | 12.8 |
| 423527 | AI206965 | Hs.105861 | *Homo sapiens* cDNA FLJ13824 fis, clone THYRO10 | 12.8 |
| 417006 | AW673606 | Hs.80758 | aspartyl-tRNA synthetase | 12.8 |
| 453552 | AL041941 | Hs.154729 | 3-phosphoinositide dependent protein kinase-1 | 12.8 |
| 453657 | W23237 | Hs.296162 | ESTs | 12.8 |
| 434414 | AI798376 | | gb: tr34b07.x1 NCI_CGAP_Ov23 *Homo sapiens* cDNA | 12.7 |
| 456051 | T85626 | Hs.76239 | hypothetical protein FLJ20608 | 12.7 |
| 451659 | BE379761 | Hs.14248 | ESTs, Weakly similar to ALU8_HUMAN ALU SUBFAM | 12.7 |
| 418216 | AA662240 | Hs.283099 | AF15q14 protein | 12.7 |
| 423281 | AJ271684 | Hs.126355 | C-type (calcium dependent, carbohydrate-recog | 12.7 |
| 424275 | AW673173 | Hs.144505 | DKFZP566F0546 protein | 12.7 |
| 440062 | AI350518 | Hs.129692 | ESTs | 12.7 |
| 444371 | BE540274 | Hs.239 | Forkhead box M1 | 12.7 |
| 412520 | AA442324 | Hs.795 | H2A histone family, member O | 12.7 |
| 413349 | BE086692 | | gb: QV1-BT0678-130400-156-g07 BT0678 *Homo sapi* | 12.7 |
| 414500 | W24087 | Hs.76285 | DKFZP564B167 protein | 12.6 |
| 429261 | AW176254 | Hs.143475 | ESTs | 12.6 |
| 402238 | | | 0 | 12.6 |
| 400280 | | | 0 | 12.6 |
| 421246 | AW582962 | Hs.300961 | ESTs, Highly similar to AF151805 1 CGI-47 pro | 12.6 |
| 442029 | AW956698 | Hs.14456 | neural precursor cell expressed, developmenta | 12.6 |
| 435502 | L13266 | Hs.105 | glutamate receptor, ionotropic, N-methyl D-as | 12.6 |
| 409964 | AW368226 | Hs.67928 | ESTs | 12.6 |
| 418793 | AW382987 | Hs.88474 | prostaglandin-endoperoxide synthase 1 (prosta | 12.5 |
| 452117 | AI421760 | Hs.77870 | *Homo sapiens* cDNA FLJ12750 fis, clone NT2RP20 | 12.5 |
| 448074 | BE621355 | Hs.27160 | ESTs | 12.5 |
| 442655 | AW027457 | Hs.30323 | ESTs | 12.5 |
| 409928 | AL137163 | Hs.57549 | hypothetical protein dJ473B4 | 12.5 |
| 400240 | | | 0 | 12.5 |
| 413048 | M93221 | Hs.75182 | mannose receptor, C type 1 | 12.5 |
| 426215 | AW963419 | Hs.155223 | ESTs | 12.5 |
| 430024 | AI808780 | Hs.227730 | integrin, alpha 6 | 12.5 |
| 445655 | AA873830 | Hs.167746 | B cell linker protein | 12.5 |
| 419941 | X98654 | Hs.93837 | phosphatidylinositol transfer protein, membra | 12.5 |
| 425280 | U31519 | Hs.1872 | phosphoenolpyruvate carboxykinase 1 (soluble) | 12.5 |
| 427767 | AI879283 | Hs.180714 | cytochrome c oxidase subunit VIa polypeptide | 12.4 |
| 450243 | AW119084 | Hs.201037 | ESTs | 12.4 |
| 408930 | AA146721 | Hs.49005 | hypothetical protein | 12.4 |
| 418783 | T41368 | | gb: ph1d1_19/1TV Outward Alu-primed hncDNA lib | 12.4 |
| 452096 | BE394901 | Hs.226785 | ESTs | 12.4 |
| 424513 | BE385864 | Hs.149894 | mitochondrial translational initiation factor | 12.4 |
| 422306 | BE044325 | Hs.227280 | *Homo sapiens* mRNA for Lsm5 protein | 12.4 |
| 409031 | AA376836 | Hs.76728 | ESTs | 12.4 |
| 435515 | N40080 | Hs.6879 | DC13 protein | 12.4 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 429583 | NM_006412 | Hs.209119 | 1-acylglycerol-3-phosphate O-acyltransferase | 12.3 |
| 449643 | R05989 | Hs.19603 | ESTs | 12.3 |
| 440313 | AL050060 | Hs.7158 | DKFZP566H073 protein | 12.3 |
| 425593 | AA278921 | Hs.1908 | proteoglycan 1, secretory granule | 12.3 |
| 447357 | AI375922 | Hs.159367 | ESTs | 12.3 |
| 405089 | | | 0 | 12.3 |
| 414972 | BE263782 | Hs.77695 | KIAA0008 gene product | 12.3 |
| 435039 | AW043921 | Hs.130526 | ESTs | 12.3 |
| 447033 | AI357412 | Hs.157601 | EST - not in UniGene | 12.3 |
| 427521 | AW973352 | Hs.299056 | ESTs | 12.3 |
| 409377 | AA300274 | Hs.115659 | *Homo sapiens* cDNA: FLJ23461 fis, clone HSI077 | 12.3 |
| 400116 | | | 0 | 12.3 |
| 445806 | AL137516 | Hs.13323 | hypothetical protein FLJ22059 | 12.2 |
| 457817 | AA247751 | Hs.79572 | cathepsin D (lysosomal aspartyl protease) | 12.2 |
| 442410 | AW996503 | Hs.197680 | ESTs | 12.2 |
| 445404 | AI261687 | Hs.145541 | ESTs, Weakly similar to JC4974 sodium iodide | 12.2 |
| 403372 | AW249152 | Hs.44017 | SIR2 (silent mating type information regulati | 12.2 |
| 427082 | AB037858 | Hs.173484 | hypothetical protein FLJ10337 | 12.2 |
| 433764 | AW753676 | Hs.39982 | ESTs | 12.2 |
| 400268 | | | 0 | 12.2 |
| 433190 | M26901 | Hs.3210 | renin | 12.2 |
| 444863 | AW384082 | Hs.301323 | ESTs | 12.2 |
| 434779 | AF153815 | Hs.50151 | potassium inwardly-rectifying channel, subfam | 12.2 |
| 451346 | NM_006338 | Hs.26312 | glioma amplified on chromosome 1 protein (leu | 12.2 |
| 430262 | AA218780 | Hs.237323 | N-acetylglucosamine-phosphate mutase | 12.2 |
| 421071 | AI311238 | Hs.104476 | ESTs | 12.2 |
| 426773 | NM_015556 | Hs.172180 | KIAA0440 protein | 12.1 |
| 409178 | BE393948 | Hs.50915 | kallikrein 5 | 12.1 |
| 400250 | | | 0 | 12.1 |
| 428450 | NM_014791 | Hs.184339 | KIAA0175 gene product | 12.1 |
| 414531 | T69387 | Hs.76364 | allograft inflammatory factor 1 | 12.1 |
| 448210 | AW247775 | Hs.7393 | hypothetical protein from EUROIMAGE 1987170 | 12.1 |
| 440081 | AA863389 | Hs.135643 | ESTs | 12.1 |
| 413179 | N99692 | Hs.75227 | NADH dehydrogenase (ubiquinone) 1 alpha subco | 12.1 |
| 447551 | BE066634 | Hs.929 | myosin, heavy polypeptide 7, cardiac muscle, | 12.1 |
| 400517 | AF242388 | Hs.149585 | lengsin | 12.1 |
| 401610 | | | 0 | 12.0 |
| 454381 | AI935093 | Hs.193428 | ESTs | 12.0 |
| 443997 | AW081465 | Hs.299644 | ESTs | 12.0 |
| 402944 | | | 0 | 12.0 |
| 430637 | BE160081 | Hs.256290 | S100 calcium-binding protein A11 (calgizzarin | 12.0 |
| 415099 | AI492170 | Hs.77917 | ubiquitin carboxyl-terminal esterase L3 (ubiq | 12.0 |
| 445422 | AV653731 | Hs.282829 | ESTs | 12.0 |
| 416667 | AK000526 | Hs.79457 | hypothetical protein FLJ20519 | 12.0 |
| 442611 | BE077155 | Hs.177537 | ESTs | 12.0 |
| 443271 | BE568568 | Hs.195704 | ESTs | 12.0 |
| 415120 | N64464 | Hs.34950 | ESTs | 12.0 |
| 439574 | AI469788 | Hs.165190 | ESTs | 12.0 |
| 405804 | | | 0 | 12.0 |
| 412519 | AA196241 | Hs.73980 | troponin T1, skeletal, slow | 12.0 |
| 414135 | NM_004419 | Hs.2128 | dual specificity phosphatase 5 | 12.0 |
| 447075 | AV662037 | Hs.124740 | ESTs | 12.0 |
| 416841 | N33878 | Hs.249495 | heterogeneous nuclear ribonucleoprotein A1 | 12.0 |
| 402943 | | | 0 | 11.9 |
| 416933 | BE561850 | Hs.80506 | small nuclear ribonucleoprotein polypeptide A | 11.9 |
| 439744 | AL389994 | Hs.301272 | ESTs, Weakly similar to homologue of *Drosphil* | 11.9 |
| 405762 | | | 0 | 11.9 |
| 408983 | NM_000492 | Hs.663 | cystic fibrosis transmembrane conductance reg | 11.9 |
| 455102 | BE005496 | | gb: CM1-BN0117-110400-183-b09 BN0117 *Homo sapi* | 11.9 |
| 402840 | | | 0 | 11.9 |
| 449183 | AW445022 | Hs.196985 | *Homo sapiens* cDNA: FLJ21135 fis, clone CAS072 | 11.9 |
| 439273 | AW139099 | Hs.269701 | ESTs | 11.9 |
| 450484 | BE220675 | | gb: ht98f11.x1 NCI_CGAP_Lu24 *Homo sapiens* cDNA | 11.9 |
| 445431 | AF137386 | Hs.12701 | plasmolipin | 11.9 |
| 401888 | | | 0 | 11.9 |
| 426037 | AW160780 | Hs.166071 | cyclin-dependent kinase 5 | 11.9 |
| 416742 | R38644 | Hs.248420 | ESTs | 11.9 |
| 418324 | AW246273 | Hs.84131 | threonyl-tRNA synthetase | 11.8 |
| 412870 | N22788 | Hs.82407 | *Homo sapiens* HSPC296 mRNA, partial cds | 11.8 |
| 432680 | T47364 | Hs.278613 | interferon, alpha-inducible protein 27 | 11.8 |
| 421478 | AI683243 | Hs.97258 | ESTs | 11.8 |
| 426635 | BE395109 | Hs.129327 | ESTs | 11.8 |
| 420523 | AA262999 | Hs.42788 | ESTs | 11.8 |
| 426227 | U67058 | Hs.168102 | Human proteinase activated receptor-2 mRNA; 3 | 11.8 |
| 416658 | U03272 | Hs.79432 | fibrillin 2 (congenital contractural arachnod | 11.8 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 441816 | AI401807 | Hs.149997 | ESTs | 11.8 |
| 424596 | AB020639 | Hs.151017 | estrogen-related receptor gamma | 11.8 |
| 400640 | | | 0 | 11.8 |
| 448133 | AA723157 | Hs.73769 | folate receptor 1 (adult) | 11.8 |
| 401532 | | | 0 | 11.8 |
| 400161 | | | 0 | 11.8 |
| 442556 | AL137761 | Hs.8379 | *Homo sapiens* mRNA; cDNA DKFZp586L2424 (from c | 11.7 |
| 451002 | AA013299 | Hs.8018 | ESTs, Weakly similar to ALU3_HUMAN ALU SUBFAM | 11.7 |
| 401879 | | | 0 | 11.7 |
| 415989 | AI267700 | Hs.111128 | ESTs | 11.7 |
| 416434 | AW163045 | Hs.79334 | nuclear factor, interleukin 3 regulated | 11.7 |
| 410616 | AW873401 | Hs.273599 | ESTs | 11.7 |
| 449239 | T24653 | Hs.23360 | likely ortholog of yeast ARV1 | 11.7 |
| 447669 | AL049985 | Hs.19180 | *Homo sapiens* mRNA; cDNA DKFZp564E122 (from cl | 11.7 |
| 436877 | AA931484 | Hs.121255 | ESTs, Weakly similar to cDNA EST EMBL: D67419 | 11.7 |
| 434560 | R13052 | Hs.3964 | *Homo sapiens* clone 24877 mRNA sequence | 11.7 |
| 448105 | AW591433 | Hs.170675 | ESTs, Weakly similar to TMS2_HUMAN TRANSMEMBR | 11.7 |
| 400279 | | | 0 | 11.6 |
| 440497 | AA887266 | Hs.144979 | ESTs | 11.6 |
| 451260 | AW750773 | | gb: CM0-CN0044-260100-164-h03 CN0044 *Homo sapi* | 11.6 |
| 429175 | AI953040 | Hs.127714 | ESTs, Moderately similar to SOX30 protein [*H*. | 11.6 |
| 408209 | NM_004454 | Hs.43697 | ets variant gene 5 (ets-related molecule) | 11.6 |
| 428856 | AA436735 | Hs.183171 | *Homo sapiens* cDNA: FLJ22002 fis, clone HEP066 | 11.6 |
| 420153 | N22120 | Hs.75277 | hypothetical protein FLJ13910 | 11.6 |
| 428760 | AI351459 | Hs.192398 | ESTs | 11.6 |
| 421401 | AW410478 | Hs.104019 | transforming, acidic coiled-coil containing p | 11.6 |
| 404502 | | | 0 | 11.6 |
| 430423 | AI190548 | Hs.143479 | ESTs, Weakly similar to hypothetical protein | 11.6 |
| 405192 | | | 0 | 11.6 |
| 439092 | AA830149 | | gb: oc44f08.s1 NCI_CGAP_GCB1 *Homo sapiens* cDNA | 11.6 |
| 401714 | | | 0 | 11.5 |
| 439335 | AA742697 | Hs.62492 | ESTs, Weakly similar to S59856 collagen alpha | 11.5 |
| 406082 | S47833 | Hs.82927 | adenosine monophosphate deaminase 2 (isoform | 11.5 |
| 401010 | | | 0 | 11.5 |
| 412140 | AA219691 | Hs.73625 | RAB6 interacting, kinesin-like (rabkinesin6) | 11.5 |
| 409339 | AB020686 | Hs.54037 | ectonucleotide pyrophosphatase/phosphodiester | 11.5 |
| 459684 | | | gb: ao86a08.x1 Schiller meningioma *Homo sapien* | 11.5 |
| 451051 | BE254309 | Hs.125262 | DKFZP586G1624 protein | 11.5 |
| 415323 | BE269352 | Hs.949 | neutrophil cytosolic factor 2 (65 kD, chronic | 11.5 |
| 412153 | R87934 | | gb: yo47b10.r1 Soares adult brain N2b4HB55Y Ho | 11.5 |
| 427256 | AL042436 | Hs.97723 | ESTs | 11.5 |
| 406708 | AI282759 | Hs.242463 | keratin 8 | 11.4 |
| 457644 | AA770080 | Hs.144962 | ESTs, Moderately similar to I59365 ubiquitin | 11.4 |
| 422848 | Z25884 | Hs.121483 | chloride channel 1, skeletal muscle (Thomsen | 11.4 |
| 424134 | AF070637 | Hs.140950 | hypothetical protein | 11.4 |
| 451931 | AK000208 | Hs.27267 | *Homo sapiens* cDNA FLJ20201 fis, clone COLF121 | 11.4 |
| 400438 | AF185611 | Hs.115352 | growth hormone 1 | 11.4 |
| 412994 | D32257 | Hs.75113 | general transcription factor IIIA | 11.4 |
| 408124 | U89337 | Hs.42853 | cAMP responsive element binding protein-like | 11.4 |
| 452249 | BE394412 | Hs.61252 | ESTs | 11.4 |
| 424627 | AA344555 | | gb: EST50715 Gall bladder I *Homo sapiens* cDNA | 11.4 |
| 405626 | | | 0 | 11.4 |
| 436690 | AA373970 | Hs.183096 | ESTs | 11.4 |
| 415862 | R51034 | Hs.144513 | ESTs | 11.4 |
| 406755 | N80129 | Hs.94360 | metallothionein 1L | 11.4 |
| 433657 | AI244368 | Hs.8124 | PH domain containing protein in retina 1 | 11.4 |
| 429612 | AF062649 | Hs.252587 | pituitary tumor-transforming 1 | 11.4 |
| 423384 | AK000906 | Hs.127273 | hypothetical protein FLJ10044 | 11.4 |
| 433053 | BE301909 | Hs.279952 | glutathione S-transferase subunit 13 homolog | 11.4 |
| 428423 | AU076517 | Hs.184276 | solute carrier family 9 (sodium/hydrogen exch | 11.3 |
| 442353 | BE379594 | Hs.49136 | ESTs | 11.3 |
| 447700 | AI420183 | Hs.171077 | ESTs, Weakly similar to similar to serine/thr | 11.3 |
| 402077 | | | 0 | 11.3 |
| 409203 | AA780473 | Hs.687 | cytochrome P450, subfamily IVB, polypeptide 1 | 11.3 |
| 405145 | | | 0 | 11.3 |
| 428248 | AI126772 | Hs.40479 | ESTs | 11.3 |
| 425508 | AA991551 | Hs.97013 | ESTs | 11.3 |
| 428340 | AF261088 | Hs.154721 | aconitase 1, soluble | 11.3 |
| 431452 | AI073641 | Hs.152372 | ESTs | 11.3 |
| 446651 | AA393907 | Hs.97179 | ESTs | 11.3 |
| 443755 | C18397 | Hs.9730 | tachykinin 3 (neuromedin K, neurokinin beta) | 11.3 |
| 436209 | AW850417 | Hs.254020 | ESTs, Moderately similar to unnamed protein p | 11.3 |
| 401020 | | | 0 | 11.3 |
| 456724 | AW247388 | Hs.301423 | calcium binding protein 1 (calbrain) | 11.2 |
| 407227 | H94949 | Hs.171955 | trophinin associated protein (tastin) | 11.2 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 402066 | | | 0 | 11.2 |
| 442721 | AI015892 | Hs.101282 | Homo sapiens mRNA; cDNA DKFZp434B102 (from cl | 11.2 |
| 401025 | | | 0 | 11.2 |
| 452423 | AA991724 | Hs.180535 | Homo sapiens cDNA: FLJ22711 fis, clone HSI133 | 11.2 |
| 431685 | AW296135 | Hs.267659 | vav 3 oncogene | 11.2 |
| 425176 | AW015644 | Hs.301430 | ESTs, Moderately similar to TEF1_HUMAN TRANSC | 11.2 |
| 435496 | AW840171 | Hs.265398 | ESTs, Weakly similar to transformation-relate | 11.2 |
| 409079 | W87707 | Hs.82065 | interleukin 6 signal transducer (gp130; oncos | 11.2 |
| 456995 | T89832 | Hs.170278 | ESTs | 11.2 |
| 419223 | X60111 | Hs.1244 | CD9 antigen (p24) | 11.2 |
| 407788 | BE514982 | Hs.38991 | S100 calcium-binding protein A2 | 11.2 |
| 407604 | AW191962 | Hs.288061 | actin, beta | 11.2 |
| 437929 | T09353 | Hs.106642 | ESTs, Weakly similar to hypothetical protein | 11.1 |
| 415789 | H01581 | | gb: yj33f08.r1 Soares placenta Nb2HP Homo sapi | 11.1 |
| 424447 | AL137376 | Hs.147368 | Homo sapiens mRNA; cDNA DKFZp434J0226 (from c | 11.1 |
| 436034 | AF282693 | Hs.150185 | inflammation-related G protein-coupled recept | 11.1 |
| 404931 | | | 0 | 11.1 |
| 445979 | AI695047 | Hs.202395 | ESTs | 11.1 |
| 446733 | AA863360 | Hs.26040 | ESTs; Highly similar to CYTOCHROME P45 IVA2 | 11.1 |
| 433133 | AB027249 | Hs.104741 | PDZ-binding kinase; T-cell originated protein | 11.1 |
| 445258 | AI635931 | Hs.147613 | ESTs | 11.1 |
| 417251 | AW015242 | Hs.99488 | ESTs; Weakly similar to ORF YKR074w [S. cerevi | 11.1 |
| 421041 | N36914 | Hs.14691 | ESTs | 11.1 |
| 425537 | AB007913 | Hs.158291 | KIAA0444 protein | 11.1 |
| 435763 | AI243929 | Hs.190419 | ESTs | 11.1 |
| 444790 | AB030506 | Hs.11955 | B9 protein | 11.1 |
| 453857 | AL080235 | Hs.35861 | DKFZP586E1621 protein | 11.1 |
| 433882 | U90441 | Hs.3622 | procollagen-proline, 2-oxoglutarate 4-dioxyge | 11.1 |
| 405358 | | | 0 | 11.1 |
| 435814 | AW615179 | Hs.152870 | ESTs | 11.0 |
| 422809 | AK001379 | Hs.121028 | hypothetical protein FLJ10549 | 11.0 |
| 446772 | AW294404 | Hs.144515 | Homo sapiens cDNA FLJ11672 fis, clone HEMBA10 | 11.0 |
| 456694 | AW016382 | Hs.105642 | Homo sapiens cDNA: FLJ23271 fis, clone HEP001 | 11.0 |
| 441128 | AA570256 | Hs.54628 | ESTs | 11.0 |
| 432677 | NM_004482 | Hs.278611 | UDP-N-acetyl-alpha-D-galactosamine: polypeptid | 11.0 |
| 412576 | AA447718 | Hs.107057 | ESTs | 11.0 |
| 411122 | F00809 | Hs.143696 | coactivator-associated arginine methyltransfe | 11.0 |
| 427225 | AA432391 | Hs.258903 | Homo sapiens mRNA for KIAA1640 protein, parti | 11.0 |
| 426260 | NM_002541 | Hs.168669 | oxoglutarate dehydrogenase (lipoamide) | 11.0 |
| 444652 | BE513613 | Hs.11538 | actin related protein 2/3 complex, subunit 1A | 11.0 |
| 431947 | AL359613 | Hs.49933 | hypothetical protein DKFZp762D1011 | 11.0 |
| 414432 | BE378174 | Hs.26506 | Homo sapiens clone CDABP0005 mRNA sequence | 11.0 |
| 458627 | AW088642 | Hs.97984 | ESTs; Weakly similar to WASP-family protein [ | 10.9 |
| 409142 | AL136877 | Hs.50758 | chromosome-associated polypeptide C | 10.9 |
| 447627 | AF090922 | Hs.285902 | CGI-113 protein | 10.9 |
| 447656 | NM_003726 | Hs.19126 | src kinase-associated phosphoprotein of 55 kD | 10.9 |
| 454227 | AW963897 | Hs.44743 | KIAA1435 protein | 10.9 |
| 402927 | | | 0 | 10.9 |
| 422380 | AA309881 | Hs.136246 | ESTs | 10.9 |
| 455986 | BE177736 | | gb: RC1-HT0598-140300-021-g06 HT0598 Homo sapi | 10.9 |
| 410962 | BE273749 | Hs.752 | FK506-binding protein 1A (12 kD) | 10.9 |
| 450361 | BE327108 | Hs.202512 | ESTs | 10.9 |
| 457484 | H57645 | | gb: yr21e01.r1 Soares fetal liver spleen 1NFLS | 10.9 |
| 407903 | AI287341 | Hs.154029 | bHLH factor Hes4 | 10.9 |
| 403398 | | | 0 | 10.9 |
| 401405 | | | 0 | 10.9 |
| 405570 | | | 0 | 10.9 |
| 421240 | R72730 | Hs.29283 | ESTs, Weakly similar to PLK_HUMAN PROTEOGLYCA | 10.9 |
| 403649 | | | 0 | 10.9 |
| 447824 | BE620800 | | gb: 601483379T1 NIH_MGC_69 Homo sapiens cDNA c | 10.9 |
| 450935 | BE514743 | Hs.25664 | tumor suppressor deleted in oral cancer-relat | 10.9 |
| 439853 | AL119566 | Hs.6721 | lysophospholipase-like | 10.9 |
| 451852 | R51928 | | gb: yj71c05.r1 Soares breast 2NbHBst Homo sapi | 10.9 |
| 431218 | NM_002145 | Hs.2733 | homeo box B2 | 10.9 |
| 457794 | AA689292 | Hs.246850 | ESTs | 10.9 |
| 444374 | AA009841 | Hs.11039 | Homo sapiens cDNA FLJ12798 fis, clone NT2RP20 | 10.9 |
| 456566 | AW235317 | Hs.259214 | ESTs | 10.8 |
| 405552 | | | 0 | 10.8 |
| 439436 | BE140845 | Hs.57868 | ESTs | 10.8 |
| 435310 | AA705075 | Hs.169536 | Rhesus blood group-associated glycoprotein | 10.8 |
| 411125 | AA151647 | Hs.68877 | cytochrome b-245, alpha polypeptide | 10.8 |
| 415807 | H03139 | Hs.24683 | ESTs | 10.8 |
| 409430 | R21945 | Hs.166975 | splicing factor, arginine/serine-rich 5 | 10.8 |
| 417033 | H83784 | Hs.40532 | ESTs, Weakly similar to PEBP MOUSE PHOSPHATID | 10.8 |
| 418464 | R87580 | | gb: ym89h07.r1 Soares adult brain N2b4HB55Y Ho | 10.8 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 404567 | | | 0 | 10.8 |
| 418384 | AW149266 | Hs.25130 | ESTs | 10.8 |
| 421971 | U63127 | Hs.110121 | SEC7 homolog | 10.8 |
| 428769 | AW207175 | Hs.106771 | ESTs | 10.8 |
| 459104 | R19238 | Hs.282057 | ESTs | 10.8 |
| 410896 | AW809637 | | gb: MR4-ST0124-261099-015-b07 ST0124 *Homo sapi* | 10.8 |
| 416969 | AI815443 | Hs.283404 | organic cation transporter | 10.8 |
| 408796 | AA688292 | Hs.118553 | ESTs | 10.8 |
| 426298 | AW965058 | Hs.111583 | ESTs | 10.8 |
| 421595 | AB014520 | Hs.105958 | *Homo sapiens* cDNA: FLJ22735 fis, clone HUV001 | 10.8 |
| 408007 | AW135965 | Hs.246783 | ESTs | 10.8 |
| 400167 | | | 0 | 10.7 |
| 445243 | AI217439 | Hs.109854 | ESTs, Weakly similar to ALU1_HUMAN ALU SUBFAM | 10.7 |
| 421733 | AL119671 | Hs.1420 | fibroblast growth factor receptor 3 (achondro | 10.7 |
| 412241 | AW948343 | | gb: RC0-MT0015-130400-031-c01 MT0015 *Homo sapi* | 10.7 |
| 425827 | W28316 | | gb: 45b6 Human retina cDNA randomly primed sub | 10.7 |
| 420255 | NM_007289 | Hs.1298 | membrane metallo-endopeptidase (neutral endop | 10.7 |
| 430891 | U22492 | Hs.248118 | G protein-coupled receptor 8 | 10.7 |
| 402883 | | | 0 | 10.7 |
| 423811 | AW299598 | Hs.50895 | homeo box C4 | 10.7 |
| 447078 | AW885727 | Hs.301570 | ESTs | 10.7 |
| 414343 | AL036166 | Hs.75914 | coated vesicle membrane protein | 10.7 |
| 446913 | AA430650 | Hs.16529 | transmembrane 4 superfamily member (tetraspan | 10.7 |
| 452279 | AA286844 | Hs.61260 | hypothetical protein FLJ13164 | 10.7 |
| 401220 | | | 0 | 10.7 |
| 459259 | AJ003294 | | gb: AJ003294 Selected chromosome 21 cDNA libra | 10.7 |
| 414171 | AA360328 | Hs.865 | RAP1A, member of RAS oncogene family | 10.7 |
| 448449 | BE314567 | Hs.211440 | ESTs | 10.7 |
| 429670 | L01087 | Hs.211593 | protein kinase C, theta | 10.7 |
| 446759 | R61463 | Hs.16165 | expressed in activated T/LAK lymphocytes | 10.7 |
| 400776 | | | 0 | 10.7 |
| 428093 | AW594506 | Hs.104830 | ESTs | 10.7 |
| 412801 | AA121055 | | gb: zm22b01.r1 Stratagene pancreas (937208) *Ho* | 10.6 |
| 440545 | AW183201 | Hs.190559 | ESTs | 10.6 |
| 434540 | NM_016045 | Hs.5184 | TH1 *drosophila* homolog | 10.6 |
| 414273 | BE269057 | | gb: 601184231F1 NIH_MGC_8 *Homo sapiens* cDNA cl | 10.6 |
| 401817 | | | 0 | 10.6 |
| 410423 | AW402432 | Hs.63489 | protein tyrosine phosphatase, non-receptor ty | 10.6 |
| 430590 | AW383947 | Hs.246381 | CD68 antigen | 10.6 |
| 426680 | AA320160 | Hs.171811 | adenylate kinase 2 | 10.6 |
| 445413 | AA151342 | Hs.12677 | CGI-147 protein | 10.6 |
| 402947 | | | 0 | 10.6 |
| 457426 | AW971119 | | gb: EST383206 MAGE resequences, MAGL *Homo sapi* | 10.6 |
| 424148 | BE242274 | Hs.1741 | integrin, beta 7 | 10.6 |
| 404944 | | | 0 | 10.6 |
| 405421 | | | 0 | 10.6 |
| 416772 | AI733872 | Hs.79769 | protocadherin 1 (cadherin-like 1) | 10.6 |
| 414191 | AW250089 | Hs.75807 | PDZ and LIM domain 1 (elfin) | 10.6 |
| 457588 | AI571225 | Hs.284171 | KIAA1535 protein | 10.6 |
| 406038 | Y14443 | Hs.88219 | zinc finger protein 200 | 10.6 |
| 404790 | | | 0 | 10.6 |
| 418922 | AW956580 | Hs.42699 | Thrombospondin-1 (Hs.87409) | 10.6 |
| 425940 | AB023184 | Hs.163990 | KIAA0967 protein | 10.6 |
| 448749 | AW859679 | Hs.21902 | *Homo sapiens* clone 25237 mRNA sequence | 10.6 |
| 418870 | AF147204 | Hs.89414 | CXCR4; chemokine CXC receptor 4 (fusin) | 10.5 |
| 417933 | X02308 | Hs.82962 | thymidylate synthetase | 10.5 |
| 450538 | AW297396 | Hs.227052 | ESTs | 10.5 |
| 427928 | AA417662 | Hs.119217 | ESTs | 10.5 |
| 432721 | AL121478 | Hs.3132 | steroidogenic acute regulatory protein | 10.5 |
| 429267 | AA299290 | Hs.246857 | ESTs, Highly similar to S71100 protein kinase | 10.5 |
| 439190 | AW978693 | Hs.293811 | ESTs | 10.5 |
| 408975 | AW958693 | Hs.49391 | hypothetical protein LOC54149 | 10.5 |
| 415130 | W85893 | Hs.249867 | ESTs | 10.5 |
| 425738 | H29630 | Hs.159408 | *Homo sapiens* clone 24420 mRNA sequence | 10.5 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 440232 | AI766925 | Hs.112554 | ESTs | 10.5 |
| 425065 | AA371906 | Hs.294151 | ESTs, Moderately similar to KIAA0544 protein | 10.5 |
| 420829 | AW665612 | Hs.221969 | ESTs | 10.5 |
| 430466 | AF052573 | Hs.241517 | polymerase (DNA directed), theta | 10.5 |
| 407771 | AL138272 | Hs.62713 | ESTs | 10.5 |
| 444611 | AK002180 | Hs.11449 | DKFZP564O123 protein | 10.5 |
| 444665 | BE613126 | Hs.47783 | ESTs, Weakly similar to T12540 hypothetical p | 10.5 |
| 448030 | N30714 | Hs.20161 | HDCME31P protein | 10.5 |
| 438982 | AW979101 | Hs.291980 | ESTs | 10.5 |
| 446224 | AW450551 | Hs.13308 | ESTs | 10.5 |
| 405108 | | | 0 | 10.5 |
| 438233 | W52448 | Hs.56147 | ESTs | 10.5 |
| 401799 | | | 0 | 10.5 |
| 454038 | X06374 | Hs.37040 | platelet-derived growth factor alpha polypept | 10.5 |
| 414222 | AL135173 | Hs.878 | sorbitol dehydrogenase | 10.5 |
| 421828 | AW891965 | Hs.289109 | dimethylarginine dimethylaminohydrolase 1 | 10.5 |
| 422626 | AA344932 | Hs.118786 | metallothionein 2A | 10.5 |
| 449261 | AI637592 | Hs.224958 | ESTs | 10.4 |
| 416218 | R21499 | Hs.23213 | ESTs | 10.4 |
| 457848 | W26524 | Hs.125682 | ESTs; Weakly similar to D2092.2 [*C. elegans*] | 10.4 |
| 442577 | AA292998 | Hs.163900 | ESTs | 10.4 |
| 406505 | AF016272 | Hs.115418 | cadherin 16, KSP-cadherin | 10.4 |
| 412258 | AA376768 | Hs.288977 | *Homo sapiens* cDNA: FLJ22622 fis, clone HSI056 | 10.4 |
| 429224 | AI905780 | Hs.198272 | NADH dehydrogenase (ubiquinone) 1 beta subcom | 10.4 |
| 447774 | BE018118 | Hs.19554 | chromosome 1 open reading frame 2 | 10.4 |
| 403914 | | | 0 | 10.4 |
| 406329 | | | 0 | 10.4 |
| 402423 | | | 0 | 10.4 |
| 431986 | AA536130 | Hs.149018 | ESTs | 10.4 |
| 423145 | BE264548 | Hs.222190 | ESTs, Weakly similar to secretory carrier mem | 10.4 |
| 414402 | BE294186 | | gb: 601172959F1 NIH_MGC_17 *Homo sapiens* cDNA c | 10.4 |
| 417079 | U65590 | Hs.81134 | interleukin 1 receptor antagonist | 10.4 |
| 426095 | AI278023 | Hs.89986 | ESTs | 10.4 |
| 434577 | R37316 | Hs.179769 | *Homo sapiens* cDNA: FLJ22487 fis, clone HRC109 | 10.4 |
| 442415 | AI005101 | Hs.129550 | ESTs | 10.3 |
| 421506 | BE302796 | Hs.105097 | thymidine kinase 1, soluble | 10.3 |
| 435084 | D17516 | Hs.301607 | adenylate cyclase activating polypeptide 1 (p | 10.3 |
| 431724 | AA514535 | Hs.283704 | ESTs | 10.3 |
| 456798 | AJ006422 | Hs.135183 | centaurin-alpha | 10.3 |
| 417370 | T28651 | Hs.82030 | tryptophanyl-tRNA synthetase | 10.3 |
| 422596 | AF063611 | Hs.118633 | 2'-5'oligoadenylate synthetase-like | 10.3 |
| 435226 | AI248938 | Hs.270106 | ESTs | 10.3 |
| 433192 | AB040880 | Hs.225594 | ESTs, Moderately similar to KIAA1447 protein | 10.3 |
| 419879 | Z17805 | Hs.93564 | Homer, neuronal immediate early gene, 2 | 10.3 |
| 416228 | AW505190 | Hs.79089 | sema domain, immunoglobulin domain (Ig), tran | 10.3 |
| 453403 | BE466639 | Hs.61779 | *Homo sapiens* cDNA FLJ13591 fis, clone PLACE10 | 10.3 |
| 447906 | AL050062 | Hs.19999 | DKFZP566K023 protein | 10.3 |
| 401782 | NM_012434 | Hs.117865 | solute carrier family 17 (anion/sugar transpo | 10.3 |
| 453927 | AA082465 | Hs.301751 | ESTs, Weakly similar to /prediction | 10.3 |
| 450737 | AW007152 | Hs.203330 | ESTs | 10.3 |
| 421633 | AF121860 | Hs.106260 | sorting nexin 10 | 10.3 |
| 409881 | AF139799 | Hs.202830 | ESTs | 10.3 |
| 432883 | U48936 | Hs.3112 | sodium channel, nonvoltage-gated 1, gamma | 10.3 |
| 440099 | AL080058 | Hs.6909 | DKFZP564G202 protein | 10.3 |
| 419024 | X56411 | Hs.1219 | alcohol dehydrogenase 4 (class II), pi polype | 10.3 |
| 401835 | | | 0 | 10.3 |
| 408896 | AI610447 | Hs.48778 | niban protein | 10.3 |
| 443120 | AW402677 | Hs.290801 | ESTs | 10.3 |
| 400208 | | | 0 | 10.2 |
| 416908 | AA333990 | Hs.80424 | coagulation factor XIII, A1 polypeptide | 10.2 |
| 400166 | | | 0 | 10.2 |
| 434642 | W25739 | Hs.135287 | ESTs | 10.2 |
| 424837 | BE276113 | Hs.153436 | N-acetyltransferase, homolog of *S. cerevisiae* | 10.2 |
| 435075 | R51094 | Hs.12400 | ESTs | 10.2 |
| 425912 | AL137629 | Hs.162189 | serine/threonine kinase with Dbl- and pleckst | 10.2 |
| 435080 | AI831760 | Hs.155111 | ESTs | 10.2 |
| 414998 | NM_002543 | Hs.77729 | oxidised low density lipoprotein (lectin-like | 10.2 |
| 410020 | T86315 | Hs.728 | ribonuclease, RNase A family, 2 (liver, eosin | 10.2 |
| 411410 | R20693 | Hs.69954 | laminin, gamma 3 | 10.2 |
| 450294 | H42587 | Hs.238730 | ESTs | 10.2 |
| 421154 | AA284333 | Hs.287631 | *Homo sapiens* cDNA FLJ14269 fis, clone PLACE10 | 10.2 |
| 414271 | AK000275 | Hs.75871 | protein kinase C binding protein 1 | 10.2 |
| 400812 | | | 0 | 10.2 |
| 425843 | BE313280 | Hs.159627 | death associated protein 3 | 10.2 |
| 449392 | Z41698 | Hs.26039 | *Homo sapiens* cDNA FLJ13937 fis, clone Y79AA10 | 10.2 |

TABLE 13A-continued

About 1086 UP-REGULATED GENES, OVARIAN CANCER VERSUS NORMAL OVARY

| Pkey | Ex. Accn | UG ID | Title | ratio |
|---|---|---|---|---|
| 409089 | NM_014781 | Hs.50421 | KIAA0203 gene product | 10.2 |
| 401383 | | | 0 | 10.2 |
| 456855 | AF035528 | Hs.153863 | MAD (mothers against decapentaplegic, Drosoph | 10.2 |
| 442912 | AI088060 | Hs.131450 | ESTs | 10.2 |
| 400954 | D25969 | Hs.76325 | Homo sapiens cDNA: FLJ23125 fis, clone LNG082 | 10.2 |
| 401029 | BE382701 | Hs.25960 | v-myc avian myelocytomatosis viral related on | 10.2 |
| 416602 | NM_006159 | Hs.79389 | nel (chicken)-like 2 | 10.2 |
| 421905 | AI660247 | Hs.32699 | ESTs, Weakly similar to LIV-1 protein [H. sapi | 10.2 |
| 405094 | | | 0 | 10.2 |
| 450832 | AW970602 | Hs.105421 | ESTs | 10.2 |
| 440076 | R32052 | Hs.178617 | ESTs, Weakly similar to AF151840 1 CGI-82 pro | 10.2 |
| 447563 | BE536115 | Hs.160983 | ESTs | 10.2 |
| 421238 | AB033101 | Hs.102796 | KIAA1275 protein | 10.2 |
| 400882 | | | 0 | 10.2 |
| 415738 | BE539367 | Hs.295953 | ESTs, Weakly similar to AF220049 1 uncharacte | 10.1 |
| 445464 | AW172389 | Hs.249999 | ESTs | 10.1 |
| 459042 | AW272058 | Hs.210338 | ESTs | 10.1 |
| 414469 | R51952 | Hs.32587 | steriod receptor RNA activator 1 (complexes w | 10.1 |
| 434732 | AI078443 | | gb: oz05g05.x1 Soares_fetal_liver_spleen_1NFLS | 10.1 |
| 441030 | AW204139 | Hs.174424 | ESTs, Weakly similar to p140mDia [M. musculus] | 10.1 |
| 446855 | BE616767 | Hs.16269 | B-cell CLL/lymphoma 7B | 10.1 |
| 456785 | AF151074 | Hs.132744 | hypothetical protein | 10.1 |
| 404182 | | | 0 | 10.1 |
| 410358 | AW975168 | Hs.13337 | ESTs, Weakly similar to unnamed protein produ | 10.1 |
| 430355 | NM_006219 | Hs.239818 | phosphoinositide-3-kinase, catalytic, beta po | 10.1 |
| 442152 | R39246 | Hs.239666 | Homo sapiens cDNA FLJ13495 fis, clone PLACE10 | 10.1 |
| 436354 | AI879252 | Hs.5151 | Homo sapiens mRNA; cDNA DKFZp564C2163 (from c | 10.1 |
| 426711 | AA383471 | Hs.180669 | conserved gene amplified in osteosarcoma | 10.1 |
| 450599 | AA460865 | Hs.48516 | ESTs | 10.1 |
| 454393 | BE153288 | | gb: PM0-HT0335-180400-008-c08 HT0335 Homo sapi | 10.1 |
| 403383 | | | 0 | 10.1 |
| 415947 | U04045 | Hs.78934 | mutS (E. coli) homolog 2 (colon cancer, nonpo | 10.1 |
| 411773 | NM_006799 | Hs.72026 | protease, serine, 21 (testisin) | 10.1 |
| 412116 | AW402166 | Hs.784 | Epstein-Barr virus induced gene 2 (lymphocyte | 10.1 |
| 413808 | J00287 | Hs.182183 | caldesmon 1 | 10.0 |
| 458572 | AI223423 | Hs.292794 | ESTs | 10.0 |
| 403295 | | | 0 | 10.0 |
| 403910 | | | 0 | 10.0 |
| 453400 | AI991901 | Hs.82590 | ESTs, Moderately similar to ALU7_HUMAN ALU SU | 10.0 |
| 406502 | | | 0 | 10.0 |
| 404743 | | | 0 | 10.0 |
| 412517 | BE271584 | | gb: 601141065F1 NIH_MGC_9 Homo sapiens cDNA cl | 10.0 |
| 402679 | | | 0 | 10.0 |
| 455864 | BE148970 | | gb: CM0-HT0245-031199-085-h05 HT0245 Homo sapi | 10.0 |
| 425734 | AF056209 | Hs.159396 | peptidylglycine alpha-amidating monooxygenase | 10.0 |
| 419280 | W07506 | Hs.283725 | Homo sapiens cDNA FLJ12627 fis, clone NT2RM40 | 10.0 |
| 443503 | AV645438 | Hs.282927 | ESTs | 10.0 |
| 423165 | AI937547 | Hs.124915 | Human DNA sequence from clone 380A1 on chromo | 10.0 |
| 450206 | AI796450 | Hs.201600 | ESTs | 10.0 |
| 459052 | AA298812 | Hs.98539 | ESTs | 10.0 |
| 456248 | AL035786 | Hs.82425 | actin related protein 2/3 complex, subunit 5 | 10.0 |
| 428438 | NM_001955 | Hs.2271 | Endothelin 1 | 10.0 |
| 456525 | AW468397 | Hs.100000 | S100 calcium-binding protein A8 (calgranulin | 10.0 |
| 426127 | L36983 | Hs.167013 | dynamin 2 | 10.0 |

Pkey: Primekey
Ex. Accn: Exemplay Accession
UG ID: UniGene ID
Title: UniGene title
ratio: ration tumor vs. normal ovary Table 19A provides UnigeneID, UnigeneTitle, Pkey, and Exemplar Accession for sequences in Table 20. Information in Table 19A is linked by SEQ ID NO: to Table 20.

TABLE 19A

| Pkey | ExAccn | UG ID | Title | SEQ ID NO: |
|---|---|---|---|---|
| 428187 | AI687303 | Hs.285529 | G protein-coupled receptor 49 | 1 and 2 |

Pkey: Unique Eos probeset identifier number
ExAccn: Exemplar Accession number, Genbank accession number
UG ID: UniGene number
Title: UniGene gene title
SEQ ID NO: Sequence Identification number for sequences in Table 20

TABLE 20

```
SEQ ID NO: 1
DNA sequence
Nucleic Acid Accession #: NM_003667.1
Coding sequence: 1..2651

1          11         21         31         41         51
|          |          |          |          |          |
ATGGACACCT CCCGGCTCGG TGTGCTCCTG TCCTTGCCTG TGCTGCTGCA GCTGGCGACC    60

GGGGGCAGCT CTCCCAGGTC TGGTGTGTTG CTGAGGGGCT GCCCCACACA CTGTCATTGC   120

GAGCCCGACG GCAGGATGTT GCTCAGGGTG GACTGCTCCG ACCTGGGGCT CTCGGAGCTG   180

CCTTCCAACC TCAGCGTCTT CACCTCCTAC CTAGACCTCA GTATGAACAA CATCAGTCAG   240

CTGCTCCCGA ATCCCCTGCC CAGTCTCCGC TTCCTGGAGG AGTTACGTCT TGCGGGAAAC   300

GCTCTGACAT ACATTCCCAA GGGAGCATTC ACTGGCCTTT ACAGTCTTAA AGTTCTTATG   360

CTGCAGAATA ATCAGCTAAG ACACGTACCC ACAGAAGCTC TGCAGAATTT GCGAAGCCTT   420

CAATCCCTGC GTCTGGATGC TAACCACATC AGCTATGTGC CCCCAAGCTG TTTCAGTGGC   480

CTGCATTCCC TGAGGCACCT GTGGCTGGAT GACAATGCGT TAACAGAAAT CCCCGTCCAG   540

GCTTTTAGAA GTTTATCGGC ATTGCAAGCC ATGACCTTGG CCCTGAACAA AATACACCAC   600

ATACCAGACT ATGCCTTTGG AAACCTCTCC AGCTTGGTAG TTCTACATCT CCATAACAAT   660

AGAATCCACT CCCTGGGAAA GAAATGCTTT GATGGGCTCC ACAGCCTAGA GACTTTAGAT   720

TTAAATTACA ATAACCTTGA TGAATTCCCC ACTGCAATTA GGACACTCTC CAACCTTAAA   780

GAACTACATT TCTATGACAA TCCCATCCAA TTTGTTGGGA GATCTGCTTT TCAACATTTA   840

CCTGAACTAA GAACACTGAC TCTGAATGGT GCCTCACAAA TAACTGAATT TCCTGATTTA   900

ACTGGAACTG CAAACCTGGA GAGTCTGACT TTAACTGGAG CACAGATCTC ATCTCTTCCT   960

CAAACCGTCT GCAATCAGTT ACCTAATCTC CAAGTGCTAG ATCTGTCTTA CAACCTATTA  1020

GAAGATTTAC CCAGTTTTTC AGTCTGCCAA AAGCTTCAGA AAATTGACCT AAGACATAAT  1080

GAAATCTACG AAATTAAAGT TGACACTTTC CAGCAGTTGC TTAGCCTCCG ATCGCTGAAT  1140

TTGGCTTGGA ACAAAATTGC TATTATTCAC CCCAATGCAT TTTCCACTTT GCCATCCCTA  1200

ATAAAGCTGG ACCTATCGTC CAACCTCCTG TCGTCTTTTC CTATAACTGG GTTACATGGT  1260

TTAACTCACT TAAAATTAAC AGGAAATCAT GCCTTACAGA GCTTGATATC ATCTGAAAAC  1320

TTTCCAGAAC TCAAGGTTAT AGAAATGCCT TATGCTTACC AGTGCTGTGC ATTTGGAGTG  1380

TGTGAGAATG CCTATAAGAT TTCTAATCAA TGGAATAAAG GTGACAACAG CAGTATGGAC  1440

GACCTTCATA AGAAAGATGC TGGAATGTTT CAGGCTCAAG ATGAACGTGA CCTTGAAGAT  1500

TTCCTGCTTG ACTTTGAGGA AGACCTGAAA GCCCTTCATT CAGTGCAGTG TTCACCTTCC  1560
```

TABLE 20-continued

```
CCAGGCCCCT TCAAACCCTG TGAACACCTG CTTGATGGCT GGCTGATCAG AATTGGAGTG   1620

TGGACCATAG CAGTTCTGGC ACTTACTTGT AATGCTTTGG TGACTTCAAC AGTTTTCAGA   1680

TCCCCTCTGT ACATTTCCCC CATTAAACTG TTAATTGGGG TCATCGCAGC AGTGAACATG   1740

CTCACGGGAG TCTCCAGTGC CGTGCTGGCT GGTGTGGATG CGTTCACTTT TGGCAGCTTT   1800

GCACGACATG GTGCCTGGTG GGAGAATGGG GTTGGTTGCC ATGTCATTGG TTTTTTGTCC   1860

ATTTTTGCTT CAGAATCATC TGTTTTCCTG CTTACTCTGG CAGCCCTGGA GCGTGGGTTC   1920

TCTGTGAAAT ATTCTGCAAA ATTTGAAACG AAAGCTCCAT TTTCTAGCCT GAAAGTAATC   1980

ATTTTGCTCT GTGCCCTGCT GGCCTTGACC ATGGCCGCAG TTCCCCTGCT GGGTGGCAGC   2040

AAGTATGGCG CCTCCCCTCT CTGCCTGCCT TTGCCTTTTG GGGAGCCCAG CACCATGGGC   2100

TACATGGTCG CTCTCATCTT GCTCAATTCC CTTTGCTTCC TCATGATGAC CATTGCCTAC   2160

ACCAAGCTCT ACTGCAATTT GGACAAGGGA GACCTGGAGA ATATTTGGGA CTGCTCTATG   2220

GTAAAACACA TGGCCCTGTT GCTCTTCACC AACTGCATCC TAAACTGCCC TGTGGCTTTC   2280

TTGTCCTTCT CCTCTTTAAT AAACCTTACA TTTATCAGTC CTGAAGTAAT TAAGTTTATC   2340

CTTCTGGTGG TAGTCCCACT TCCTGCATGT CTCAATCCCC TTCTCTACAT CTTGTTCAAT   2400

CCTCACTTTA AGGAGGATCT GGTGAGCCTG AGAAAGCAAA CCTACGTCTG GACAAGATCA   2460

AAACACCCAA GCTTGATGTC AATTAACTCT GATGATGTCG AAAAACAGTC CTGTGACTCA   2520

ACTCAAGCCT TGGTAACCTT TACCAGCTCC AGCATCACTT ATGACCTGCC TCCCAGTTCC   2580

GTGCCATCAC CAGCTTATCC AGTGACTGAG AGCTGCCATC TTCCCTCTGT GGCATTTGTC   2640

CCATGTCTTA A
```

SEQ ID NO: 2
Protein sequence:
Protein Accession #: NP_003658.1

```
1          11         21         31         41         51
|          |          |          |          |          |
MDTSRLGVLL SLPVLLQLAT GGSSPRSGVL LRGCPTHCHC EPDGRMLLRV DCSDLGLSEL    60

PSNLSVFTSY LDLSMNNISQ LLPNPLPSLR FLEELRLAGN ALTYIPKGAF TGLYSLKVLM   120

LQNNQLRHVP TEALQNLRSL QSLRLDANHI SYVPPSCFSG LHSLRHLWLD DNALTEIPVQ   180

AFRSLSALQA MTLALNKIHH IPDYAFGNLS SLVVLHLHNN RIHSLGKKCF DGLHSLETLD   240

LNYNNLDEFP TAIRTLSNLK ELHFYDNPIQ FVGRSAFQHL PELRTLTLNG ASQITEFPDL   300

TGTANLESLT LTGAQISSLP QTVCNQLPNL QVLDLSYNLL EDLPSFSVCQ KLQKIDLRHN   360

EIYEIKVDTF QQLLSLRSLN LAWNKIAIIH PNAFSTLPSL IKLDLSSNLL SSFPITGLHG   420

LTHLKLTGNH ALQSLISSEN FPELKVIEMP YAYQCCAFGV CENAYKISNQ WNKGDNSSMD   480

DLHKKDAGMF QAQDERDLED FLLDFEEDLK ALHSVQCSPS PGPFKPCEHL LDGWLIRIGV   540

WTIAVLALTC NALVTSTVFR SPLYISPIKL LIGVIAAVNM LTGVSSAVLA GVDAFTFGSF   600

ARHGAWWENG VGCHVIGFLS IFASESSVFL LTLAALERGF SVKYSAKFET KAPFSSLKVI   660

ILLCALLALT MAAVPLLGGS KYGASPLCLP LPFGEPSTMG YMVALILLNS LCFLMMTIAY   720

TKLYCNLDKG DLENIWDCSM VKHIALLLFT NCILNCPVAF LSFSSLINLT FISPEVIKFI   780

LLVVVPLPAC LNPLLYILFN PHFKEDLVSL RKQTYVWTRS KHPSLMSINS DDVEKQSCDS   840

TQALVTFTSS SITYDLPPSS VPSPAYPVTE SCHLSSVAFV PCL
```

It is understood that the examples described above in no way serve to limit the true scope of this invention, but rather are presented for illustrative purposes. All publications, sequences of accession numbers, and patent applications cited in this specification are herein incorporated by reference as if each individual publication or patent application were specifically and individually indicated to be incorporated by reference.

What is claimed is:

1. A method of detecting ovarian cancer in a patient, the method comprising:
   (i) detecting a nucleic acid in a first sample from the patient, wherein the nucleic acid sequence is at least 95% identical to SEQ ID NO:1, and wherein the nucleic acid encodes a G protein.coupled receptor 49; and
   (ii) comparing the expression level of the nucleic acid in the-first sample to the expression level in a normal sample;
   wherein an increase in the level of the nucleic acid relative to the normal sample is indicative of ovarian cancer.

2. The method of claim 1, wherein the first sample comprises isolated nucleic acids.

3. The method of claim 2, wherein the nucleic acids are mRNA.

4. The method of claim 2, wherein the method further comprises the step of amplifying nucleic acids before the step of detecting the nucleic acid.

5. The method of claim 1, wherein the nucleic acid comprises SEQ ID NO:1.

6. The method of claim 1, wherein the detecting step is carried out by using a nucleic acid probe that hybridizes under stringent conditions to a nucleic acid comprising SEQ ID NO:1.

7. The method of claim 6, wherein the probe is immobilized on a solid surface.

8. The method of claim 1, wherein the patient is suspected of having ovarian cancer.

9. The method of claim 1, wherein the patient is suspected of having ovarian cancer.

10. An isolated nucleic acid molecule, wherein the nucleic acid molecule comprises a sequence at least 99% identical to SEQ ID NO:1.

11. The nucleic acid molecule of claim 10, wherein the nucleic acid molecule is labeled.

12. An expression vector comprising the nucleic acid of claim 10.

13. A host cell comprising the expression vector of claim 12.

14. A method of monitoring ovarian cancer in a human patient, the method comprising:

(i) detecting a nucleic acid in a first sample from the patient, wherein the nucleic acid sequence is at least 95% identical to SEQ ID NO:1, and wherein the nucleic acid encodes a G protein-coupled receptor 49;

(ii) comparing the expression level of the nucleic acid in the first sample to the expression level in a normal sample.

15. The method of claim 14, wherein the sample comprises blood from the patient.

16. The method of claim 14, wherein the nucleic acid sequence comprises SEQ ID NO:1.

17. The method of claim 14, wherein the detecting step is carried out by using a nucleic acid probe that hybridizes under stringent conditions to a sequence comprising SEQ ID NO:1.

18. The method of claim 17, wherein the probe is immobilized on a solid surface.

* * * * *

SEQUENCE LISTING

<160> NUMBER OF SEQ ID NOS: 2

<210> SEQ ID NO 1
<211> LENGTH: 2651
<212> TYPE: DNA
<213> ORGANISM: Homo Sapiens

<400> SEQUENCE: 1

```
atggacacct cccggctcgg tgtgctcctg tccttgcctg tgctgctgca gctggcgacc      60
gggggcagct ctcccaggtc tggtgtgttg ctgaggggct gccccacaca ctgtcattgc     120
gagcccgacg gcaggatgtt gctcaggtg gactgctccg acctggggct ctcggagctg     180
ccttccaacc tcagcgtctt cacctcctac ctagacctca gtatgaacaa catcagtcag     240
ctgctcccga atccctgcc cagtctccgc ttcctggagg agttacgtct tgcgggaaac     300
gctctgacat acattcccaa gggagcattc actggccttt acagtcttaa agttcttatg     360
ctgcagaata atcagctaag acacgtaccc acagaagctc tgcagaattt gcgaagcctt     420
caatccctgc gtctggatgc taaccacatc agctatgtgc ccccaagctg tttcagtggc     480
ctgcattccc tgaggcacct gtggctggat gacaatgcgt taacagaaat ccccgtccag     540
gcttttagaa gtttatcggc attgcaagcc atgaccttgg ccctgaacaa aatacaccac     600
ataccagact atgcctttgg aaacctctcc agcttggtag ttctacatct ccataacaat     660
agaatccact ccctgggaaa gaaatgcttt gatgggctcc acagcctaga gactttagat     720
ttaaattaca ataaccttga tgaattcccc actgcaatta ggacactctc caaccttaaa     780
gaactacatt tctatgacaa tcccatccaa tttgttggga gatctgcttt tcaacattta     840
cctgaactaa gaacactgac tctgaatggt gcctcacaaa taactgaatt tcctgattta     900
actggaactg caaacctgga gagtctgact ttaactggag cacagatctc atctcttcct     960
caaaccgtct gcaatcagtt acctaatctc caagtgctag atctgtctta caacctatta    1020
gaagatttac ccagtttttc agtctgccaa aagcttcaga aaattgacct aagacataat    1080
gaaatctacg aaattaaagt tgacactttc agcagttgc ttagcctccg atcgctgaat    1140
ttggcttgga acaaaattgc tattattcac cccaatgcat tttccacttt gccatcccta    1200
ataaagctgg acctatcgtc caacctcctg tcgtcttttc ctataactgg gttacatggt    1260
ttaactcact taaaattaac aggaaatcat gccttacaga gcttgatatc atctgaaaac    1320
tttccagaac tcaaggttat agaaatgcct tatgcttacc agtgctgtgc atttggagtg    1380
tgtgagaatg cctataagat ttctaatcaa tggaataaag gtgacaacag cagtatggac    1440
gaccttcata agaaagatgc tggaatgttt caggctcaag atgaacgtga cctttgaagat    1500 ttcctgcttg actttgagga agacctgaaa gcccttcatt cagtgcagtg ttcaccttcc    1560
ccaggcccct tcaaaccctg tgaacacctg cttgatggct ggctgatcag aattggagtg    1620
tggaccatag cagttctggc acttacttgt aatgctttgg tgacttcaac agttttcaga    1680
tcccctctgt acatttcccc cattaaactg ttaattgggg tcatcgcagc agtgaacatg    1740
ctcacgggag tctccagtgc cgtgctggct ggtgtggatc gttcacttt tggcagcttt    1800 gcacgacatg gtgcctggtg ggagaatggg gttggttgcc atgtcattgg ttttttgtcc    1860
```

```
attttttgctt cagaatcatc tgttttcctg cttactctgg cagccctgga gcgtgggttc    1920
tctgtgaaat attctgcaaa atttgaaacg aaagctccat tttctagcct gaaagtaatc    1980
attttgctct gtgccctgct ggccttgacc atggccgcag ttcccctgct gggtggcagc    2040
aagtatggcg cctcccctct ctgcctgcct ttgccttttg gggagcccag caccatgggc    2100
tacatggtcg ctctcatctt gctcaattcc ctttgcttcc tcatgatgac cattgcctac    2160
accaagctct actgcaattt ggacaaggga gacctggaga atatttggga ctgctctatg    2220
gtaaaacaca ttcccctgtt gctcttcacc aactgcatcc taaactgccc tgtggctttc    2280
ttgtccttct cctctttaat aaaccttaca tttatcagtc ctgaagtaat taagtttatc    2340
cttctggtgg tagtcccact tcctgcatgt ctcaatcccc ttctctacat cttgttcaat    2400
cctcacttta aggaggatct ggtgagcctg agaaagcaaa cctacgtctg gacaagatca    2460
aaacacccaa gcttgatgtc aattaactct gatgatgtcg aaaaacagtc ctgtgactca    2520
actcaagcct tggtaacctt taccagctcc agcatcactt atgacctgcc tcccagttcc    2580
gtgccatcac cagcttatcc agtgactgag agctgccatc tttcctctgt ggcatttgtc    2640
ccatgtctta a                                                         2651
```

<210> SEQ ID NO 2
<211> LENGTH: 883
<212> TYPE: PRT
<213> ORGANISM: Homo Sapiens

<400> SEQUENCE: 2

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220
```

-continued

```
Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
            245                 250                 255

Ser Asn Leu Lys Glu Leu His Phe Tyr Asp Asn Pro Ile Gln Phe Val
        260                 265                 270

Gly Arg Ser Ala Phe Gln His Leu Pro Glu Leu Arg Thr Leu Thr Leu
    275                 280                 285

Asn Gly Ala Ser Gln Ile Thr Glu Phe Pro Asp Leu Thr Gly Thr Ala
290                 295                 300

Asn Leu Glu Ser Leu Thr Leu Thr Gly Ala Gln Ile Ser Ser Leu Pro
305                 310                 315                 320

Gln Thr Val Cys Asn Gln Leu Pro Asn Leu Gln Val Leu Asp Leu Ser
            325                 330                 335

Tyr Asn Leu Leu Glu Asp Leu Pro Ser Phe Ser Val Cys Gln Lys Leu
        340                 345                 350

Gln Lys Ile Asp Leu Arg His Asn Glu Ile Tyr Glu Ile Lys Val Asp
    355                 360                 365

Thr Phe Gln Gln Leu Leu Ser Leu Arg Ser Leu Asn Leu Ala Trp Asn
370                 375                 380

Lys Ile Ala Ile Ile His Pro Asn Ala Phe Ser Thr Leu Pro Ser Leu
385                 390                 395                 400

Ile Lys Leu Asp Leu Ser Ser Asn Leu Leu Ser Ser Phe Pro Ile Thr
            405                 410                 415

Gly Leu His Gly Leu Thr His Leu Lys Leu Thr Gly Asn His Ala Leu
        420                 425                 430

Gln Ser Leu Ile Ser Ser Glu Asn Phe Pro Glu Leu Lys Val Ile Glu
    435                 440                 445

Met Pro Tyr Ala Tyr Gln Cys Cys Ala Phe Gly Val Cys Glu Asn Ala
450                 455                 460

Tyr Lys Ile Ser Asn Gln Trp Asn Lys Gly Asp Asn Ser Ser Met Asp
465                 470                 475                 480

Asp Leu His Lys Lys Asp Ala Gly Met Phe Gln Ala Gln Asp Glu Arg
            485                 490                 495

Asp Leu Glu Asp Phe Leu Leu Asp Phe Glu Glu Asp Leu Lys Ala Leu
        500                 505                 510

His Ser Val Gln Cys Ser Pro Ser Pro Gly Pro Phe Lys Pro Cys Glu
    515                 520                 525

His Leu Leu Asp Gly Trp Leu Ile Arg Ile Gly Val Trp Thr Ile Ala
530                 535                 540

Val Leu Ala Leu Thr Cys Asn Ala Leu Val Thr Ser Thr Val Phe Arg
545                 550                 555                 560

Ser Pro Leu Tyr Ile Ser Pro Ile Lys Leu Leu Ile Gly Val Ile Ala
            565                 570                 575

Ala Val Asn Met Leu Thr Gly Val Ser Ser Ala Val Leu Ala Gly Val
        580                 585                 590

Asp Ala Phe Thr Phe Gly Ser Phe Ala Arg His Gly Ala Trp Trp Glu
    595                 600                 605

Asn Gly Val Gly Cys His Val Ile Gly Phe Leu Ser Ile Phe Ala Ser
610                 615                 620

Glu Ser Ser Val Phe Leu Leu Thr Leu Ala Ala Leu Glu Arg Gly Phe
625                 630                 635                 640

Ser Val Lys Tyr Ser Ala Lys Phe Glu Thr Lys Ala Pro Phe Ser Ser
```

-continued

```
                    645                 650                 655
Leu Lys Val Ile Ile Leu Leu Cys Ala Leu Leu Ala Leu Thr Met Ala
                660                 665                 670
Ala Val Pro Leu Leu Gly Gly Ser Lys Tyr Gly Ala Ser Pro Leu Cys
                675                 680                 685
Leu Pro Leu Pro Phe Gly Glu Pro Ser Thr Met Gly Tyr Met Val Ala
                690                 695                 700
Leu Ile Leu Leu Asn Ser Leu Cys Phe Leu Met Met Thr Ile Ala Tyr
705                 710                 715                 720
Thr Lys Leu Tyr Cys Asn Leu Asp Lys Gly Asp Leu Glu Asn Ile Trp
                725                 730                 735
Asp Cys Ser Met Val Lys His Ile Ala Leu Leu Leu Phe Thr Asn Cys
                740                 745                 750
Ile Leu Asn Cys Pro Val Ala Phe Leu Ser Phe Ser Ser Leu Ile Asn
                755                 760                 765
Leu Thr Phe Ile Ser Pro Glu Val Ile Lys Phe Ile Leu Leu Val Val
770                 775                 780
Val Pro Leu Pro Ala Cys Leu Asn Pro Leu Leu Tyr Ile Leu Phe Asn
785                 790                 795                 800
Pro His Phe Lys Glu Asp Leu Val Ser Leu Arg Lys Gln Thr Tyr Val
                805                 810                 815
Trp Thr Arg Ser Lys His Pro Ser Leu Met Ser Ile Asn Ser Asp Asp
                820                 825                 830
Val Glu Lys Gln Ser Cys Asp Ser Thr Gln Ala Leu Val Thr Phe Thr
                835                 840                 845
Ser Ser Ser Ile Thr Tyr Asp Leu Pro Pro Ser Ser Val Pro Ser Pro
850                 855                 860
Ala Tyr Pro Val Thr Glu Ser Cys His Leu Ser Ser Val Ala Phe Val
865                 870                 875                 880
Pro Cys Leu
```